(12) United States Patent
van de Ven et al.

(10) Patent No.: US 12,564,728 B2
(45) Date of Patent: Mar. 3, 2026

(54) TREATMENT OF CENTRAL NERVOUS SYSTEM DISORDERS

(71) Applicant: KNOW Bio, LLC, Durham, NC (US)

(72) Inventors: Antony van de Ven, Nong Kae (TH); Nathan Stasko, Chapel Hill, NC (US); F. Neal Hunter, Durham, NC (US); David Emerson, Durham, NC (US); Cui Cui Bao, Nong Kae (TH)

(73) Assignee: KNOW Bio, LLC, Morrisville, NC (US)

( * ) Notice: Subject to any disclaimer, the term of this patent is extended or adjusted under 35 U.S.C. 154(b) by 586 days.

(21) Appl. No.: 17/632,688

(22) PCT Filed: Aug. 5, 2020

(86) PCT No.: PCT/US2020/044986
§ 371 (c)(1),
(2) Date: Feb. 3, 2022

(87) PCT Pub. No.: WO2021/026218
PCT Pub. Date: Feb. 11, 2021

(65) Prior Publication Data
US 2022/0280807 A1     Sep. 8, 2022

Related U.S. Application Data

(60) Provisional application No. 62/882,632, filed on Aug. 5, 2019.

(51) Int. Cl.
*A61N 5/06*     (2006.01)
*A61N 2/00*     (2006.01)
*A61N 2/02*     (2006.01)

(52) U.S. Cl.
CPC ........... *A61N 5/0603* (2013.01); *A61N 2/006* (2013.01); *A61N 2/02* (2013.01); *A61N 5/0618* (2013.01);
(Continued)

(58) Field of Classification Search
CPC ........ A61N 5/0603; A61N 2/006; A61N 2/02; A61N 5/0618; A61N 5/0622;
(Continued)

(56) References Cited

U.S. PATENT DOCUMENTS 7,303,578 B2 *  12/2007  De Taboada ......... A61N 5/0622
                                                              128/898
7,678,140 B2 *   3/2010  Brainard .............. A61B 5/4848
                                                               607/91
(Continued)

FOREIGN PATENT DOCUMENTS

CN           1935289 A      3/2007
CN         206167649 U      5/2017
(Continued)

OTHER PUBLICATIONS

Boldrini, et al., "Hippocampal Angiogenesis and Progenitor Cell Proliferation are Increased with Antidepressant Use in Major Depression," Biological Psychiatry, vol. 72, Issue 7, Oct. 2012, 21 pages.
(Continued)

*Primary Examiner* — Ahmed M Farah
(74) *Attorney, Agent, or Firm* — Withrow & Terranova, P.L.L.C.

(57)          ABSTRACT
Devices and methods for treating central nervous system disorders by administering light to a user are disclosed. In some embodiments, the devices are positioned away from the user, and in other embodiments, the devices are attached to the user. In some embodiments, the light is applied through the users skin, and in other embodiments, through an implanted or percutaneous device. Representative central nervous system disorders include cognitive, motor, and behavioral disorders. Where these disorders include an inflammatory component, light is administered at wavelengths which decrease inflammation in the brain. Where these disorders are caused by poor vascularization, light is
(Continued)

administered at wavelengths which improve vascularization in the brain. The methods also include repairing damage to the blood brain barrier, and can be used to more effectively administer drugs, such as anticancer drugs, to the brain.

29 Claims, 11 Drawing Sheets

(52) U.S. Cl.
  CPC .... *A61N 5/0622* (2013.01); *A61N 2005/0605* (2013.01); *A61N 2005/0607* (2013.01); *A61N 2005/0608* (2013.01); *A61N 2005/0611* (2013.01); *A61N 2005/0648* (2013.01)

(58) Field of Classification Search
  CPC .... A61N 2005/0605; A61N 2005/0607; A61N 2005/0608; A61N 2005/0611; A61N 2005/0648; A61N 5/062; A61N 5/0624; A61N 2/002; A61N 2005/0602; A61N 2005/0606; A61N 2005/061; A61N 2005/0612; A61N 2005/0626; A61N 2005/0637; A61N 2005/0647; A61N 2005/0642; A61N 2005/0645; A61N 2005/0659; A61N 2005/0661; A61N 2005/0663; A61N 5/06
  USPC ......................................................... 607/88
  See application file for complete search history.

(56) References Cited

U.S. PATENT DOCUMENTS

| 8,821,559 | B2 | 9/2014 | DiMauro et al. | |
| 9,403,030 | B2 | 8/2016 | Oron et al. | |
| 9,919,162 | B2 | 3/2018 | Knight | |
| 9,950,189 | B1 | 4/2018 | Morries et al. | |
| 10,188,872 | B2 | 1/2019 | De Taboada et al. | |
| 10,471,276 | B2 | 11/2019 | Beckner et al. | |
| 10,525,275 | B2 | 1/2020 | Stasko et al. | |
| 11,123,366 | B1 * | 9/2021 | Taraman | A61K 41/0057 |
| 2008/0033412 | A1 | 2/2008 | Whelan et al. | |
| 2009/0204185 | A1 | 8/2009 | De Kok et al. | |
| 2009/0319008 | A1 | 12/2009 | Mayer | |
| 2010/0121420 | A1 | 5/2010 | Fiset et al. | |
| 2010/0160904 | A1 * | 6/2010 | McMillan | A61B 18/24 |
| | | | | 606/18 |
| 2010/0179469 | A1 | 7/2010 | Hammond et al. | |
| 2010/0204762 | A1 | 8/2010 | De Taboada et al. | |
| 2011/0144723 | A1 * | 6/2011 | Streeter | A61N 5/0618 |
| | | | | 607/88 |
| 2011/0242453 | A1 | 10/2011 | Van De Ven et al. | |
| 2012/0046716 | A1 | 2/2012 | Dougal | |
| 2012/0065709 | A1 * | 3/2012 | Dunning | A61N 5/06 |
| | | | | 607/88 |
| 2013/0131762 | A1 * | 5/2013 | Oversluizen | A61N 5/0616 |
| | | | | 607/90 |
| 2014/0088668 | A1 | 3/2014 | Kim et al. | |
| 2015/0112411 | A1 | 4/2015 | Beckman et al. | |
| 2015/0209597 | A1 * | 7/2015 | Haarlander | A61H 23/02 |
| | | | | 607/90 |
| 2015/0360049 | A1 | 12/2015 | Kaplitt et al. | |
| 2016/0129279 | A1 | 5/2016 | Ferolito | |
| 2016/0235983 | A1 | 8/2016 | Berman et al. | |
| 2017/0028216 | A1 | 2/2017 | Medendorp, Jr. et al. | |
| 2017/0239489 | A1 | 8/2017 | Bourke, Jr. et al. | |
| 2018/0169434 | A1 | 6/2018 | Shanks | |
| 2018/0214708 | A1 * | 8/2018 | Laty | A61N 5/0618 |
| 2019/0070431 | A1 * | 3/2019 | Zivin | A42B 1/242 |
| 2019/0143138 | A1 | 5/2019 | Segal et al. | |
| 2019/0232083 | A1 | 8/2019 | Deligianni et al. | |

FOREIGN PATENT DOCUMENTS

| CN | 107049254 | A | 8/2017 |
| JP | 2006288965 | A | 10/2006 |
| JP | 2010233920 | A | 10/2010 |
| KR | 101092670 | B | 12/2011 |
| KR | 1020150143456 | A | 12/2015 |
| KR | 1020170058958 | A | 5/2017 |
| TW | 1287462 | B | 10/2007 |
| WO | 2010078581 | A1 | 7/2010 |
| WO | 2012020361 | A1 | 2/2012 |
| WO | 2012024243 | A1 | 2/2012 |
| WO | WO 2012024243 | * | 2/2012 |
| WO | 2012164393 | A1 | 12/2012 |
| WO | 2016007798 | A2 | 1/2016 |
| WO | 2016040534 | A1 | 3/2016 |
| WO | WO 2016040534 | * | 3/2016 |
| WO | 2018022775 | A1 | 2/2018 |
| WO | 2019053625 | A1 | 3/2019 |
| WO | 2019165302 | A1 | 8/2019 |

OTHER PUBLICATIONS

Chung, et al., "Alteration in cerebral perfusion in posttraumatic stress disorder patients without re-exposure to accident-related stimuli," Clinical Neurophysiology, vol. 117, Issue 3, 2006, Elsevier Ireland Ltd., pp. 637-642.

Figueiro, et al., "The Effects of Red and Blue Lights on Circadian Variations in Cortisol, Alpha Amylase, and Melatonin," International Journal of Endocrinology, vol. 2010, Article 829351, Hindawi Publishing Corporation, 10 pages.

Gal, et al., "Anxiety and depression—the role of blood-brain barrier integrity," Official Journal of the Hungarian Association of Psychopharmacology, vol. 21, Issue 1, pp. 19-25 (english abstract).

Gao, et al., "Novel anti-inflammatory therapy for Parkinson's disease," Trends in Pharmacological Sciences, vol. 24, Issue 8, Aug. 2003, Elsevier Ltd., pp. 395-401.

Greenberg, et al., "A proposed metabolic strategy for monitoring disease progression in Alzheimer's disease," Electrophoresis, vol. 30, 2009, pp. 1235-1239.

Groveman, et al., "Rapid and ultra-sensitive quantitation of disease-associated a-synuclein seeds in brain and cerebrospinal fluid by aSyn RT-QuIC," Acta Neuropathologica Communications, vol. 6, Issue 7, 2018, 10 pages.

Henderson, "The diagnosis and evaluation of dementia and mild cognitive impairment with emphasis on SPECT perfusion neuroimaging," CNS Spectrums, vol. 17, Issue 4, 2012, 31 pages.

Ivey, et al., "AIDS and the blood-brain barrier," Journal of Neurovirology, vol. 15, Issue 2, 2009, 19 pages.

Kaye, et al., "Neurobiology of Anorexia and Bulimia Nervosa Purdue Ingestive Behavior Research Center Symposium Influences on Eating and Body Weight over the Lifespan: Children and Adolescents," Physiology and Behavior, vol. 94, Issue 1, Apr. 22, 2008, 30 pages.

Kuhl, et al., "Patterns of Local Cerebral Glucose Utilization Determined in Parkinson's disease by the F18-Fluorodeoxyglucose Method," Annals of Neurology, vol. 15, 1984, pp. 419-424.

Lucas, et al., "The role of inflammation in CNS injury and disease," British Journal of Pharmacology, vol. 147, Suppl 1, 2006, pp. S232-S240.

Markus, et al., "HMPAO SPECT in Parkinson's disease before and after levodopa: correlation with dopaminergic responsiveness," Journal of Neurology, Neurosurgery, and Psychiatry, vol. 57, 1994, pp. 180-185.

Miguel-Puga, et al., "Therapeutic Interventions for Vascular Parkinsonism: A Systematic Review and Meta-analysis," Frontiers in Neurology, vol. 8, Article 481, Sep. 2017, 12 pages.

Morries, et al., "Treatments for traumatic brain injury with emphasis on transcranial near-infrared laser phototherapy," Neuropsychiatric Disease and Treatment, Aug. 2015, 17 pages.

Palmqvist, et al., "Discriminative Accuracy of Plasma Phospho-tau217 for Alzheimer Disease vs. Other Neurodegenerative Disorders," JAMA, vol. 324, Issue 8, Aug. 25, 2020, American Medical Association, pp. 772-781.

(56) References Cited

OTHER PUBLICATIONS

Perdiz, et al., "Distribution and Repair of Bipyrimidine Photoproducts in Solar UV-irradiated Mammalian Cells," Journal of Biological Chemistry, vol. 275, Issue 35, 2000, pp. 26732-26742.

Raivich, et al., "Brain microglia and blood-derived macrophages: molecular profiles and functional roles in multiple sclerosis and animal models of autoimmune demyelinating disease," Brain Research Reviews, vol. 46, Nov. 2004, Elsevier B.V., pp. 261-281.

Raji, et al., "Clinical Utility of SPECT Neuroimaging in the Diagnosis and Treatment of Traumatic Brain Injury: A Systematic Review," PLoS One, vol. 9, Issue 3, Mar. 2014, 10 pages.

Ravanant, et al., "Direct and indirect effects of UV radiation on DNA and its components," Journal of Photochemistry and Photobiology, vol. 63, 2001, pp. 88-102.

Sachinvala, et al., "Increased Regional Cerebral Perfusion by 99mTc Hexamethyl Propylene Amine Oxime Single Photon Emission Computed Tomogrpahy in Post-Traumatic Stress Disorder," Military Medicine vol. 165, Issue 6, Jun. 2000, pp. 473-479.

Saura, et al., "An Antiviral Mechanism of Nitric Oxide: Inhibition of a Viral Protease," Immunity, vol. 10, Jan. 1999, Cell Press, 8 pages.

Tehranian, "Improved Recovery and Delayed Cytokine Induction after Closed Head Injury in Mice with Central Overexpression of the Secreted Isoform of the Interleukin-1 Receptor Antagonist," Journal of Neurotrama, vol. 19, Issue 8, 2002, Mary Ann Liebert, Inc., 13 pages.

Everbroeck, et al., "The role of cytokines, astrocytes, microglia and apoptosis in Creutzfeldt-Jakob disease," Neurobiology of Aging, vol. 23, 2002, pp. 59-64.

Van De Haar, et al., "Blood-Brain Barrier Leakage in Patients with Early Alzheimer Disease," Radiology, vol. 282, Issue 2, Feb. 2016, 9 pages.

Waubant, "Biomarkers indicative of blood-brain barrier disruption in multiple sclerosis," Disease Markers, vol. 22, Issue 4, 2006, IOS Press, pp. 235-244.

Yoshihara, et al., "Differential expression of inflammation- and apoptosis-related genes in spinal cords of a mutant BOD1 transgenic mousemodel of familial amyotrophic lateral sclerosis," Journal of Neurochemistry, 2002, vol. 80, Issue 1, pp. 158-167.

International Search Report and Written Opinion for International Patent Application No. PCT/US2020/044986, mailed Feb. 22, 2021, 15 pages.

Extended European Search Report for European Patent Application No. 20849367.6, mailed Feb. 28, 2023, 10 pages.

First Office Action for Chinese Patent Application No. 202080055874. 0, mailed Jun. 28, 2024, 17 pages.

Notice of Preliminary Rejection for Korean Patent Application No. 10-2022-7007048, mailed May 31, 2024, 16 pages.

Examination Report No. 2 for Australian Patent Application No. 2020325024, mailed Oct. 23, 2023, 3 pages.

Notice of Acceptance for Australian Patent Application No. 2020325024, mailed Mar. 15, 2024, 3 pages.

Examination Report No. 1 for Australian Patent Application No. 2020325024, mailed Mar. 9, 2023, 3 pages.

Johnstone, et al., "Turning on Lights to Stop Neurodegeneration: The Potential of Near Infrared Light Therapy in Alzheimer's and Parkinson's Disease," Frontiers in Neuroscience, vol. 9, Article 500, Jan. 11, 2016, 15 pages.

Salgado, et al., "The effects of transcranial LED therapy (TCLT) on cerebral blood flow in the elderly women," Lasers in Surgery and Medicine, Draft, Oct. 2014, John Wiley & Sons, Inc., 13 pages.

Examination Report No. 3 for Australian Patent Application No. 2020325024, mailed Jan. 23, 2024, 7 pages.

Examination Report No. 4 for Australian Patent Application No. 2020325024, mailed Feb. 28, 2024, 4 pages.

Notice of Reasons for Refusal for Japanese Patent Application No. 2022-507425, mailed Feb. 28, 2024, 16 pages.

Second Office Action for Chinese Patent Application No. 202080055874. 0, mailed Oct. 26, 2024, 16 pages.

Notice of Final Rejection for Korean Patent Application No. 10-2022-7007048, mailed Feb. 26, 2025, 5 pages.

Examination Report for European Patent Application No. 20849367. 6, mailed Mar. 14, 2025, 4 pages.

Reconsideration Report for Japanese Patent Application No. 2022-507425, mailed Mar. 21, 2025, 4 pages.

Decision of Refusal for Japanese Patent Application No. 2022-507425, mailed Aug. 9, 2024, 12 pages.

Examination Report No. 1 for Australian Patent Application No. 2024204469, mailed Aug. 22, 2025, 3 pages.

Notice of Acceptance for Australian Patent Application No. 2024204469, mailed Sep. 9, 2025, 3 pages.

Search Report and Written Opinion for Brazilian Patent Application No. 112022002237-9, mailed Oct. 22, 2025, 8 pages.

Written Decision on Registration for Korean Patent Application No. 10-2022-7007048, mailed Nov. 6, 2025, 12 pages.

* cited by examiner

Surface Directed at Head

TREATMENT OF CENTRAL NERVOUS SYSTEM DISORDERS

This application is a 35 U.S.C. § 371 national phase filing of International Application No. PCT/US2020/044986, filed Aug. 5, 2020, which claims the benefit of U.S. provisional patent application Ser. No. 62/882,632, filed Aug. 5, 2019, the disclosures of which are incorporated herein by reference in their entireties.

FIELD OF THE INVENTION

Treatments for central nervous system disorders, and devices for administering such treatments are disclosed. The treatments involve administering electromagnetic radiation to users at specific wavelengths, and the devices are capable of administering these treatments. The treatments can, in various embodiments, increase vascularization in the brain, decrease inflammation in the brain, and/or increase passage of drugs through the blood-brain barrier, and thus treat a variety of central nervous system disorders.

BACKGROUND

Inflammation and poor vascularization each play a role in central nervous system disorders.

The CNS exhibits features of inflammation. In response to injury, infection or disease, resident CNS cells generate inflammatory mediators, including proinflammatory cytokines, prostaglandins, free radicals and complement, which in turn induce chemokines and adhesion molecules, recruit immune cells, and activate glial cells. Inflammation and inflammatory mediators contribute to acute, chronic and psychiatric CNS disorders (see, for example, Lucas, Sian-Marie et al. "The role of inflammation in CNS injury and disease." *British journal of pharmacology* vol. 147 Suppl 1, (2006): S232-40. doi:10.1038/sj.bjp.0706400).

Some of the key features of CNS inflammation include glial activation, edema, MHC expression, systemic acute phase response with general inflammation and acute phase protein synthesis, complement activation—e.g. anaphylatoxins, and membrane attack complex, the synthesis of inflammatory mediators—e.g. cytokines, free radicals, and prostaglandins, the expression of adhesion molecules, and the invasion of immune cells. Neurons, astrocytes, microglia and oligodendrocytes can produce inflammatory mediators, and cytokine receptors are expressed constitutively throughout the CNS.

Interleukin (IL)-1 is an inflammatory mediator present when a patient suffers a stroke or traumatic brain injury. Acute administration of the naturally occurring antagonist IL-1ra can inhibit inflammation and treat stroke and traumatic brain injury (Tehranian et al., J. Neurotrauma, 2002; 19:939-951). However, chronic administration might not be advisable, because Interleukin (IL)-1 incudes growth factors, reduces glutamate release, enhances GABA effects, modulates neuronal responses to NMDA and glycine, and increases activation of inducible nitric oxide synthase (iNOS), which can help with healing, particularly where the increased activation of iNOS can increase vascularization in the CNS. Tumor necrosis factor-α (TNFα) is one of the central mediators of tissue inflammation and has also been implicated in the pathogenesis of many neurological conditions.

The mechanisms that control expression of different cytokines are often related; TNFα stimulates expression of IL-1 and IL-6, and IL-1 can induce both IL-6 and TNFα. Thus, following an insult to the brain, initial upregulation of cytokines leads to infiltration of other inflammatory mediators to the site of injury, initiating secondary cytokine signaling.

CNS inflammation has been associated with acute brain injury, stroke, epilepsy, multiple sclerosis (MS), motor neuron disease, movement disorders, Alzheimer's disease, and psychiatric disorders such as depression, anxiety and schizophrenia.

Anti-inflammatory agents can reduce the probability of developing AD, or slow its progression. Many inflammatory mediators are upregulated in MS and associated with the demyelinating lesions (Raivich et al., Brain Res. Brain Res. Rev. 2004; 46:261-281). Parkinson's disease (PD) is characterized by loss of dopaminergic neurons in the substantia nigra, and motor symptoms of tremor, muscle rigidity and bradykinesia. The role of inflammation has been strongly implicated (Gao et al., Trends Pharmacol Sci. 2003 August; 24(8):395-401). Inflammation is also believed to contribute to other chronic CNS disorders, such as amyotrophic lateral sclerosis (ALS) (Yoshihara et al., J Neurochem. 2002 January; 80(1):158-67), and Creutzfeldt-Jakob disease (CJD) (Van et al., 2002). Serum levels of many cytokines, including IL-1β and IL-6, are increased in patients with schizophrenia and depression. Epilepsy is associated with increased levels of IL-1 and TNFα.

Inadequate blood flow can damage and eventually kill cells, and the brain is especially vulnerable. It is estimated that 15% to 20% of dementia cases in older adults are due to vascular dementia. A decline in cognitive ability can occur suddenly after a stroke, which blocks major blood vessels in the brain. Microvascular ischemic brain disease, also known as small vessel disease, is the narrowing of the blood vessels, causing a significant reduction of the blood supply to the brain tissues. It is associated with memory loss and caused by poor vascularization.

Vascular disease contributes to geriatric depression, cognitive impairment and poor antidepressant response, which lends support to the proposition that vascularization plays a crucial role in depressive symptomatology. At least some antidepressants increase human hippocampal neural progenitor cells (NPCs) and angiogenesis selectively in the anterior and mid dentate gyrus (DG). (Boldrini, Maura et al. "Hippocampal angiogenesis and progenitor cell proliferation are increased with antidepressant use in major depression." Biological psychiatry vol. 72,7 (2012): 562-71. doi: 10.1016/j.biopsych.2012.04.024).

In vascular Parkinsonism, small strokes in brain areas that control movement cause Parkinson's-like symptoms (Miguel-Puga, Adan et al. "Therapeutic Interventions for Vascular Parkinsonism: A Systematic Review and Meta-analysis." Frontiers in neurology vol. 8 481. 22 Sep. 2017, doi:10.3389/fneur.2017.00481). This indicates a causal link between poor vascularization in the brain and certain motor disorders.

Cerebrovascular disease, which includes a variety of medical conditions that affect the blood vessels of the brain and the cerebral circulation, is associated with motor and cognitive disorders, including stroke, migraines, seizures, epilepsy, and cognitive decline.

Accordingly, there is a role of both vascularization and inflammation in a number of central nervous system disorders.

Impairment of the blood-brain barrier (BBB) can also lead to a variety of CNS disorders. Disorders associated with an impaired blood brain barrier include Alzheimer's disease (van de Haar H J, et al., "Blood-Brain Barrier Leakage in Patients with Early Alzheimer Disease". Radiology. 282 (2): 615 (February 2017)), anxiety and depression (Gal Z, Huse R J, Gonda X, Kumar S, Juhasz G, Bagdy G, Petschner P (March 2019). "[Anxiety and depression—the role of blood-brain barrier integrity]". Neuropsychopharmacologia Hungarica. 21 (1): 19-25), brain abscesses (caused by inflammation and collection of lymphatic cells and infected material originating from a local or remote infection), De Vivo disease (also known as GLUT1 deficiency syndrome, resulting from inadequate transportation of the sugar glucose across the blood-brain barrier, typically caused by genetic defects in glucose transporter type 1 (GLUT1), HIV encephalitis (Ivey N S, MacLean A G, Lackner A A (April 2009). "Acquired immunodeficiency syndrome and the blood-brain barrier". Journal of Neurovirology. 15 (2): 111-22), Meningitis (associated with inflammation of the membranes that surround the brain and spinal cord, i.e., meninges), multiple sclerosis (Waubant E (2006). "Biomarkers indicative of blood-brain barrier disruption in multiple sclerosis". Disease Markers. 22 (4): 235-44), and neuromyelitis optica, also known as Devic's disease, which is similar to multiple sclerosis.

Although pharmaceutical agents are available to treat many of these disorders, it would be advantageous to provide adjunct therapy to minimize inflammation in the brain, increase vascularization, and/or repair the blood brain barrier. The present invention provides such adjunct therapy.

SUMMARY

A variety of specific treatments for central nervous system disorders, which treatments involve administering electromagnetic radiation at specific wavelengths, are disclosed, along with devices that can deliver these treatments.

In some embodiments, the treatments are designed to simplify delivery of electromagnetic radiation to users, and/or that can enhance compliance in users having such treatments administered, in some embodiments with little or no effort required by the user receiving the treatment.

Central nervous system disorders that can be treated using the treatments and devices described herein include cognitive disorders, movement disorders, and behavioral disorders. In some embodiments, the treatments decrease inflammation in the brain, and therefore can be used to treat central nervous system disorders associated with inflammation. In other embodiments, the treatments increase vascularization in the brain, and therefore can be used to treat central nervous system disorders associated with decreased vascularization in the brain. In still other embodiments, the treatments repair defects in the blood brain barrier, and/or increase the flow of drugs and other agents through the blood brain barrier, and therefore can be used to treat disorders associated with a defective blood brain barrier, and/or to increase the ability of drugs to cross the blood brain barrier and treat disorders of the brain, such as brain cancers.

Combinations of these approaches can be used, for example, by administering light at more than one wavelength, where the combinations of wavelengths are effective at one or more of increasing vascularization, decreasing inflammation, and increasing the passage of agents through the blood brain barrier. The light can also be used to inhibit microbial infection in the brain, when administered at antimicrobial wavelengths.

The light can be delivered to various parts of the body. When administered to the head, the light can be applied at an extra-cranial position, for example, via the external auditory canal, and also trans-cranially through one or more of the followings cranial bones: the temporal bone, squama temporalis of the temporal bone, mastoid portion of the temporal bone, petrous portion of the temporal bone, tympanic part of the temporal bone, the zygomatic bone, the sphenoid bone, the frontal bone, the parietal bone.

The treatments, and devices which administer them, can use one or more light sources, such as LED, OLED, laser light sources, and combinations thereof.

The devices used to administer these treatments typically include a housing, one or more light sources (which can be LED, OLED, SLD, laser, and combinations thereof), which emit light at desired wavelengths, and, optionally, a driver, optionally one or more sensors, and, optionally a command module.

The light can be administered in any way that allows the light to pass through the skin and into the brain. Examples include intra-cranial administration, delivery through the scalp, such as by using a therapeutic helmet or cap, delivery to the eyes, such as by using eyeglasses that shine light through the eyelids, or by shining light from a screen, intranasal delivery, such as by light sources inserted in the nostrils, delivery to the ears, delivery to sites remote from the brain, such as through skin overlying a bone, delivery to a user sitting inside an enclosure, delivery to a panel, which can be flat or curved, which shines light on the user's body, delivery to the blood, delivery to the skin, delivery to a body cavity, such as the throat, a "wearable" device for irradiating the skin, a probe designed to penetrate the skin and deliver light underneath the skin, a biocompatible implant that is implanted underneath the scalp, a transcutaneous irradiation module, and combinations thereof.

Representative disorders that can be treated include Picks disease, Alzheimer's dementia, Lewy body dementia, primary progressive aphasia, Huntington's chorea, Parkinson's disease, multiple sclerosis, multi-infarct dementia, brain injury due to trauma, brain injury due to hypoxia, cerebrovascular accident, central nervous pathology due to heavy metal poisoning, trisomy 21, viral encephalitis, viral meningitis, attention deficit hyperactivity disorder (ADHD), learning disability, autism and schizophrenia and depression.

In some embodiments, an illumination device comprising a light source, such as one or more LEDs and/or lasers, timers, sensors and control means, is designed to be mounted or positioned near a user's head such that while the user sits, rests or sleeps, the device will automatically illuminate the head with near infrared light (NIR) and/or other colored light to reduce or delay the onset of the symptoms of cognitive disorders, such as Alzheimer's disease or dementia, movement disorders, such as Parkinson's disease, and behavioral/mood disorders, such as depression and schizophrenia. In some embodiments, a device can additionally include visible light illumination for time-appropriate general lighting. In some embodiments, the device is configured to be positioned such that when a person is likely to be, or scheduled to be, or detected to be, lying in bed (or sitting in a chair) the device will turn on and shine the NIR and/or visible light on the user's head or the region of the bed or chair where the user's head would normally be positioned for a selected period of time. The NIR/light is of sufficient strength to penetrate the user's head and illuminate the user's brain and, in the case of invisible NIR, not distract or awaken the user by the illumination.

NIR directed through the skull into the brain can delay or improve the symptoms of AD (Alzheimer's disease), other cognitive disorders, and various behavioral/mood disorders and motor disorders.

Photobiomodulation therapy is defined as a form of light therapy that utilizes non-ionizing light sources, including lasers, light emitting diodes, and/or broadband light, in the visible (400-700 nm) and near-infrared (700-1100 nm) electromagnetic spectrum. Photobiomodulation may be used on the whole body or on one or more selected portions, e.g., on the head alone.

In some embodiments, head-mount products are used, though AD patients may find head-mounted devices cumbersome and difficult to use, and may have difficulty complying unaided with such AD therapy regimes. Some aspects of the present inventive subject matter provide a non-contact device to allow people or their loved ones to automatically illuminate their brains with NIR while they sleep with no hassle, hands-free convenience and automatic compliance.

In certain embodiments, described herein, the devices can include any of the other features described herein, as well as additional features described below.

In some embodiments, the devices are configured to be activated automatically when a user is present (or likely to be present) and for a preset period of time so that user receives only the prescribed amount of modulated illumination per day. In some embodiments, the devices include one or more proximity sensors such that the device activates or is remotely activated when a user is detected as present.

In some embodiments, the devices include one or more sensors. Such sensors (if included) can be any desired sensor or combination of sensors, e.g., one or more of the following: one or more proximity detectors to control when the device operates and for how long (e.g., sensor(s) configured to control light emission characteristics, by detecting if a person is present and/or detecting movement); one or more cameras configured to provide facial recognition to confirm compliance and/or remote monitoring; sensor(s) to detect biomarkers (pulse, respiration, brain wave, activity); sensor(s) to detect activity or to monitor restlessness; sensor(s) to monitor environmental conditions such as ambient temperature, ambient humidity, ambient light level, ambient noise, music, etc., with components such as microphones, cameras, temperature sensors, light detectors, ultrasonic transducers; sleep monitor(s); GPS sensor(s) so that the device knows its location, etc. Devices can be configured such that such detection (by one or more sensors) can be used to automatically change illumination characteristics of the device and/or such detection be relayed to a remote carer who might then adjust illumination characteristics. A sensor (or sensors)(if provided) may be integral to the device (such as an inbuilt microphone or inbuilt camera for face recognition or recording compliance) or may be remote (e.g., a chest-mounted pulse sensor, or wrist-mounted pulse monitor).

In some embodiments, the devices include one or more timers such that the device illuminates the head of the user or area near the head of the user for an "on time" and after such on time elapses, the illumination is turned off and remains off until a new user is detected and/or an appropriate "off time" has elapsed so that a user does not overuse the therapy.

In some embodiments, the devices comprise one or more timers. A timer may be configured such that it can be set to turn on at a specific time of day, turn off at a specific time of day, stay on for a specific time length, etc. A timer may also be configured such that it can be set to cause the device to automatically operate at a preset time of day or night. In addition to a timer to control the duration and repeat schedule of the therapeutic illumination, a device may use the real time clock and actual time of day/night and calendar such that the device can control the illumination schedule. For example a schedule of twice per day, 5 days a week for 20 days could be used. Additionally, such a clock could also control the color of a secondary visible light such that the visible light's amplitude and spectral makeup is adjusted based on the time of the night. For example, the device can be configured such that if the device is turned on at midnight, the light level would be low and the CCT would be warm such that the user's melanopsin level remains appropriate for sleep; inversely, if the device is turned on in the morning, it may illuminate at a high lux level with a higher CCT to provide alertness and wakefulness.

In some embodiments, the devices are configured to be mounted on a bed or near the end of a bed (or a chair) and the device is configured to shine light in the area of the position of the head (and/or other body parts). The device can be mounted, for example, using suction cups, Velcro®, clamps, screws, bolts, straps, adhesive, attachment to a stand, etc. A device may be positioned under a pillow, under a mattress, within a pillow or within a mattress. A device can be made an integral part of a bed or a chair, e.g., it can be built into a bed or a chair.

For example, a representative specific embodiment of a device is a device that is configured to "know" the time and emit any specific electromagnetic radiation (or combination of electromagnetic radiation) for a specific period (or periods) of time at a time of day (or night) based on selections set on the device tailored for the user. For example, the device could be configured to turn on for 20 min at 2:00 am every second day.

In some embodiments, the devices comprise one or more control features. Such control features can be any suitable control, which can be activated in any suitable way, e.g., by voice, by gesture, by remote control IR, bluetooth, smart phone apps), by touch (such as manipulable switches or control buttons that can be triggered by touching, such as control buttons at any suitable location on a device, e.g., on the device's illuminating part or on the device's control unit), etc. Such control features (if included) can be for any desired control, e.g., cutoff (on/off), a light switch to turn on a visible light for reading, a control to turn on a night light, etc.

In some embodiments, the devices comprise one or more audio components. Such audio components (if included) can be, e.g., circuits that detect voice and respond to voice commands, audio speakers or transducers to provide audio responses or instruction to the user. Such audio components (if included) may be configured such that they can be used by a remote carer to speak with the user.

In some embodiments, the devices include a means for transmitting and receiving data, e.g., using IR, bluetooth or WIFI.

In some embodiments, the devices include one or more batteries, and/or in which the device is configured to be connected to an external power source directly or through a power convertor to a wall plug.

In some embodiments, the devices include electromagnetic radiation emitters (e.g., lasers or LEDs (light emitting diodes)) mounted on different surfaces of the device, e.g., including NIR LEDs on one or more surfaces of the device that faces the user; a combination of NIR and visible light LEDs on one or more surfaces of the device that face the user; NIR and/or visible on one or more surfaces of the device that face the user and other visible LEDs on one or more surfaces of the device that face away from the user (e.g., to illuminate the surrounding area or ceiling etc.).

In some embodiments, the devices are configured to have desired radiation emission patterns, e.g., in which a device is configured to have (1) a narrow radiation emission pattern such that some radiation is directed in a narrow beam to a selected area (e.g., NIR is projected in a narrow beam on the user's head), and (2) light emitted by one or more red, amber or white emitters are directed in a wide angle and projected toward the ceiling to provide ambient illumination.

In some embodiments, the devices are configured to modulate emission of electromagnetic radiation. For example, such modulation (if included) can include multiple modulation methods superimposed, and which may be synchronized in real time to a biomarker such as brain waves, respiration, pulse, external audio sounds. Such modulation (if included) can be provided in any suitable way, e.g., by using (PWM) pulse width modulation for 0 to 100% pulse width at frequencies from 1 Hz to 10 Khz (typically 5 Hz to 100 hz), and/or by using amplitude modulation from 0 to 100% and frequencies from 0.000001 Hz (weekly) to 10 Khz. Different colors or types or locations of LEDs in the device can be modulated differently at the same time, for example, NIR LEDs directed at the head may have a 30 Hz modulation at 100% amplitude, while visible lights directed at the ceiling may have 100% pulse width (non-pulse) at a low slow amplitude synchronized to the user's respiration to create a visually relaxing ambient effect.

In some embodiments, the devices comprise one or more additional lighting functions. Such additional lighting functions (if included) can comprise the device being configured to emit a mixture or combination of NIR and visible light (in some cases, synchronized to brain waves using bio-feedback, to improve sleep patterns by providing ambient light modulation and/or synchronized photomodulation during sleep cycles). Such additional lighting functions (if included) can also comprise the device being configured to emit other wavelengths, e.g., which can be used when the user is not sleeping, for example to provide bright blue rich white light in the morning for waking up alert, and/or doses of colored light to improve skin tone—red for circulation, yellow and green for collagen and blue for bacteria reduction.

Further additional functions include, for example, embodiments in which the device comprises a room light, a night light, a toilet light, a reading light, a wake-up light, a noise generator (e.g., white noise to assist in sleeping, calming noise for relaxation), or in which the device is configured to carry out data logging (e.g., the device can include data storage to record the times it is in use (and the emissions provided during each such use), data storage to save pictures of the user, data storage of a user's (or users') activity and life signs, etc.).

Devices and methods in accordance with the present inventive subject matter can provide myriad benefits to any persons, and in some instances, particularly significant benefits are provided to patients with AD and/or dementia, elderly persons, students, persons with busy lifestyles (e.g., use of NIR for sleep improvement), gamers (e.g., use of NIR for performance enhancement).

In some embodiments, for example, using the techniques disclosed in U.S. Pat. No. 9,403,030, visible or infrared light, for example, at wavelengths between around 630 and around 910 nm, is also delivered to bone marrow to subjects having or developing Alzheimer's disease. The radiation is delivered to sites remote from the brain at a dose sufficient to cause stimulated mesenchymal stem cells to appear in the brain and degrade β-amyloid plaques. The administered light can be coherent or incoherent, and can be administered via transcutaneous application or direct application (on the bone), at both IR and other wavelengths. The bone can be a tibia, pelvic girdle, upper extremity, upper limb girdle, a rib, vertebra and/or sternum.

In other embodiments, for example, using the techniques disclosed in U.S. Pat. No. 9,950,189, the light therapy described herein is provided in combination with ketamine, which upregulates neurotrophins and improves mitochondrial function. In one aspect of this embodiment, the dosage of ketamine is a sub-anesthetic dose of 0.01-5 mg/kg body weight.

In other embodiments, rather than or in addition to administering light directly to the scalp, so as to penetrate the scalp and provide light to the brain, one can administer light below the skin, into a body cavity or to the blood. The mouth, ears, and nose constitute suitable body cavities for administering light to the brain.

In some embodiments, in addition to the administration of light, additional treatments can include traditional Chinese medicine/color-puncture, stimulation of acupuncture/trigger points (1-40 mm), Bonghan channel hyaluronic acid/stem cell treatments, behavioral healthcare/psychiatric treatments (cognitive-behavioral, biofeedback, EMDR, deep relaxation, etc.).

In another embodiment, in addition to the treatments described herein, chronic visual stimuli having a frequency of about 30 Hz to about 50 Hz, and more specifically about 40 Hz, are non-invasively delivered to the subject to entrain gamma oscillations in multiple brain regions of the subject, including the prefrontal cortex (PFC) and the hippocampus. The entrained gamma oscillations modulate neuronal activity across multiple brain regions (e.g., facilitate functional binding of neural networks at low gamma frequencies) to induce various neuroprotective effects (e.g., amelioration of amyloid plaques and tau hyper-phosphorylation) and reduce neurodegeneration. Neuronal activity mediated by the chronic visual stimuli reduces an immune response in microglia and ameliorates aberrantly modified genes and proteins involved in membrane trafficking, intracellular transport, synaptic function, neuroinflammation and DNA damage response. Behavior modification including enhanced learning and memory is observed.

Magnetic treatments, such as PEMF, can also be administered in addition to the light treatments described herein.

The treatments can be combined with pharmaceutical treatments. Representative pharmaceutical treatments include anticancer agents, anti-amyloid drugs (e.g., β-secretase inhibitors), anti-inflammatory drugs (e.g., nonsteroidal, anti-inflammatory agents, anti-complement agent (e.g., Properidin, C3, MASP-2, C5 inhibitors), anti-psychotics/antidepressants, compounds used to treat motor disorders, such as levodopa, and the like.

There are a number of ways to evaluate the effectiveness of the methods described herein. Treatment can be followed, for example, by following changes in blood pressure, blood flow, pulse, heart rate variability, blood oxygen saturation, electromyocardiographic response, respiration rate, respiration pattern, galvanic skin response, pupil dilation, trabecular-ciliary process distance, magnetic resonance imaging, brain waves, physical movements, muscle tension, self reporting, and combinations thereof. The progression of many cognitive disorders are correlated with blood, CSF, or plasma protein, enzyme, or metabolite concentrations, which can be used to evaluate the effectiveness of treatments.

When used to treat cognitive disorders, a subject can be evaluated for changes in cognition, using standard tests, for example, testing memory, problem solving skills, and the like. When used to treat behavioral disorders, standard psychological evaluations can be used to measure progress. When used to treat motor disorders, a physician can evaluate changes in the severity of the motor disorder.

In addition, one can performing imaging techniques on the patient's brain, ideally before and after treatment, to monitor the effectiveness of the treatment and/or the progression of the disorder. For example, one can perform a first PET or SPECT neuroimaging scan on the patient, and identify areas of the patient's brain to be treated. Ideally, this information can be used to help target the application of light to the area so identified. After treatment, whether immediately after, or some period of time after, a second PET or SPECT scan can be performed, and the results of the two scans compared so as to changes in the patient's brain in response to treatment.

As disclosed in U.S. Publication No. 20080033412, one can use feedback from one of a spectrophotometer and a patient physiology monitoring system to follow and/or adjust the treatment. This can help determine a minimum effective dose of irradiating light for a therapeutic process in a particular patient. One can identify an internal target area of a patient affected by a pathology, and irradiate an externally accessible area of the patient proximate to the internal target area with light at a given wavelength, flux and fluence. One can then receive feedback from one of a spectrophotometer and a patient physiology monitoring system, and adjusting the amount of light that is administered until the desired effect is obtained.

Certain metabolites are associated with specific CNS disorders, and a patient can be evaluated for the presence of those metabolites both before and after treatment. This can be particularly valuable for monitoring the progress of brain dysfunction. For example, various metabolites are known to be associated with Alzheimer's disease (Greenberg et al., "A proposed metabolic strategy for monitoring disease progression in Alzheimer's disease," Electrophoresis. 2009 Apr.; 30(7):1235-9 and Palmqvist et al, "Discriminative Accuracy of Plasma Phospho-tau217 for Alzheimer Disease vs Other Neurodegenerative Disorders" JAMA. Published online Jul. 28, 2020. doi:10.1001/jama.2020.12134), and the concentration of one or more of these metabolites can be followed over time.

The inventive subject matter may be more fully understood with reference to the accompanying drawings and the following detailed description of the inventive subject matter.

10

Figure 6:
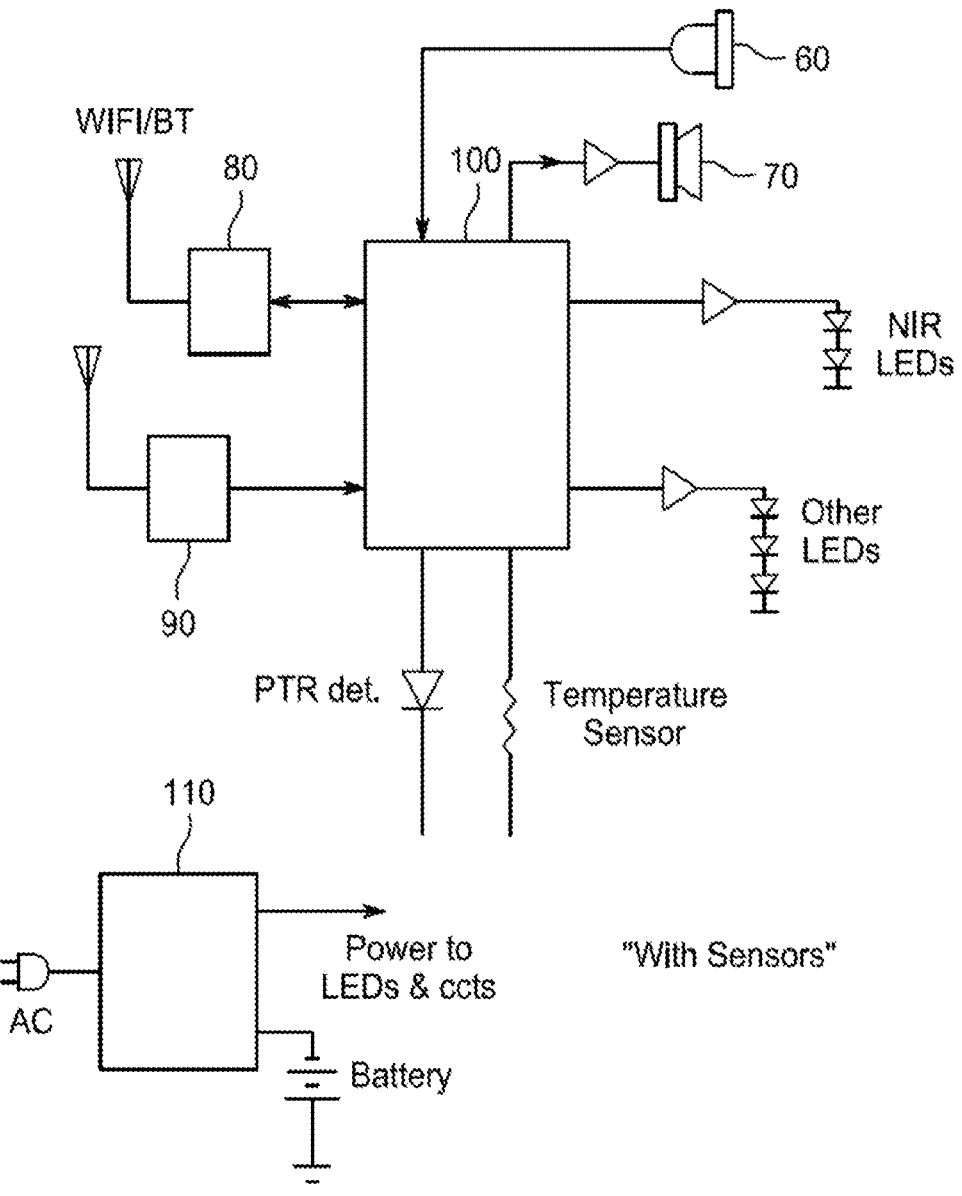

FIG. 6 schematically depicts (as a block diagram) circuitry for an embodiment of an electromagnetic radiation-emitting device in accordance with the present inventive subject matter.

Figure 7:
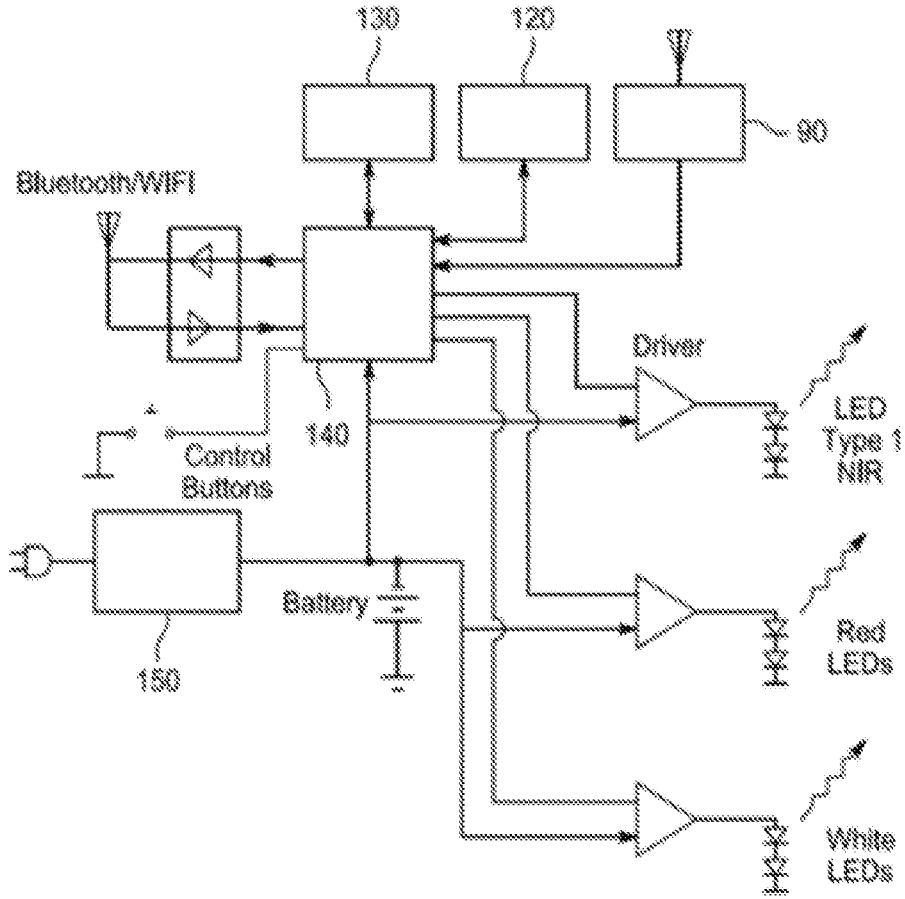

FIG. 7 schematically depicts (as a block diagram) additional circuitry for an embodiment of an electromagnetic radiation-emitting device in accordance with the present inventive subject matter.

Figure 8:
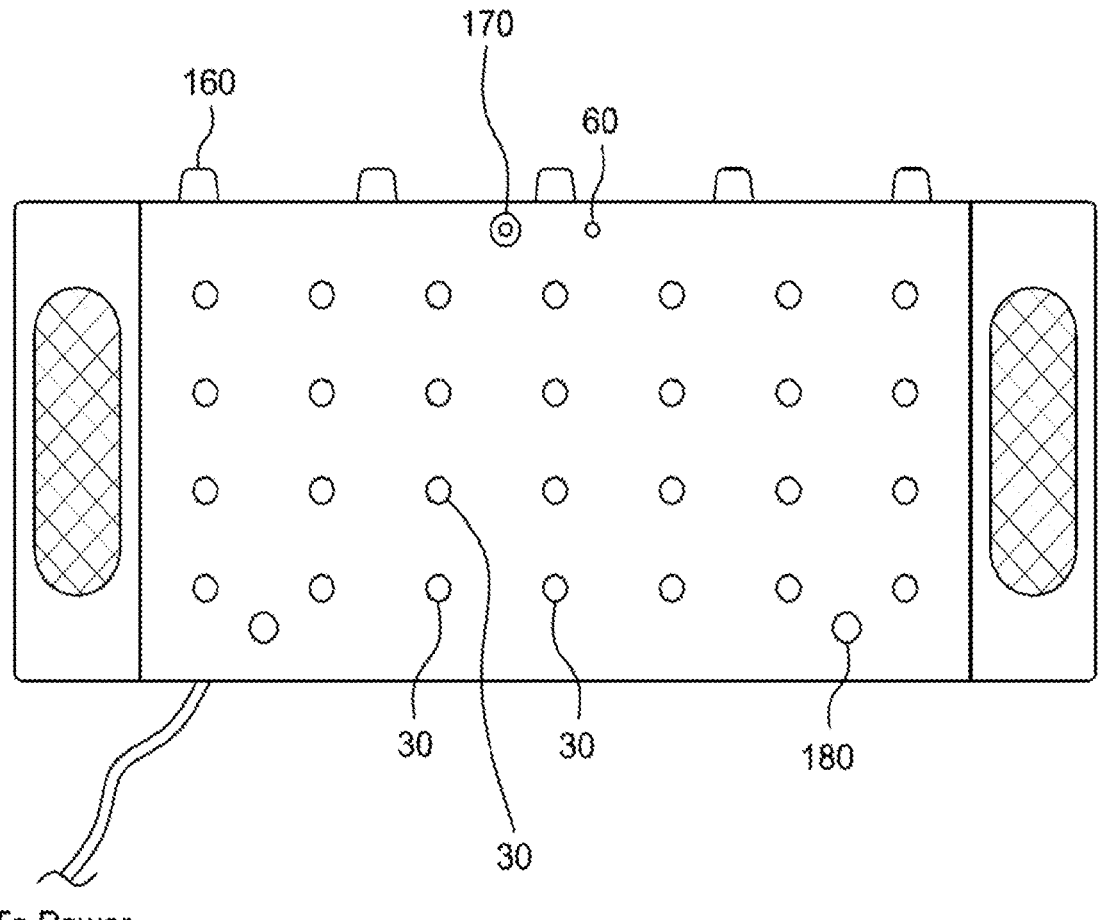

FIG. 8 schematically depicts another embodiment of an electromagnetic radiation-emitting device in accordance with the present inventive subject matter.

Figure 9:
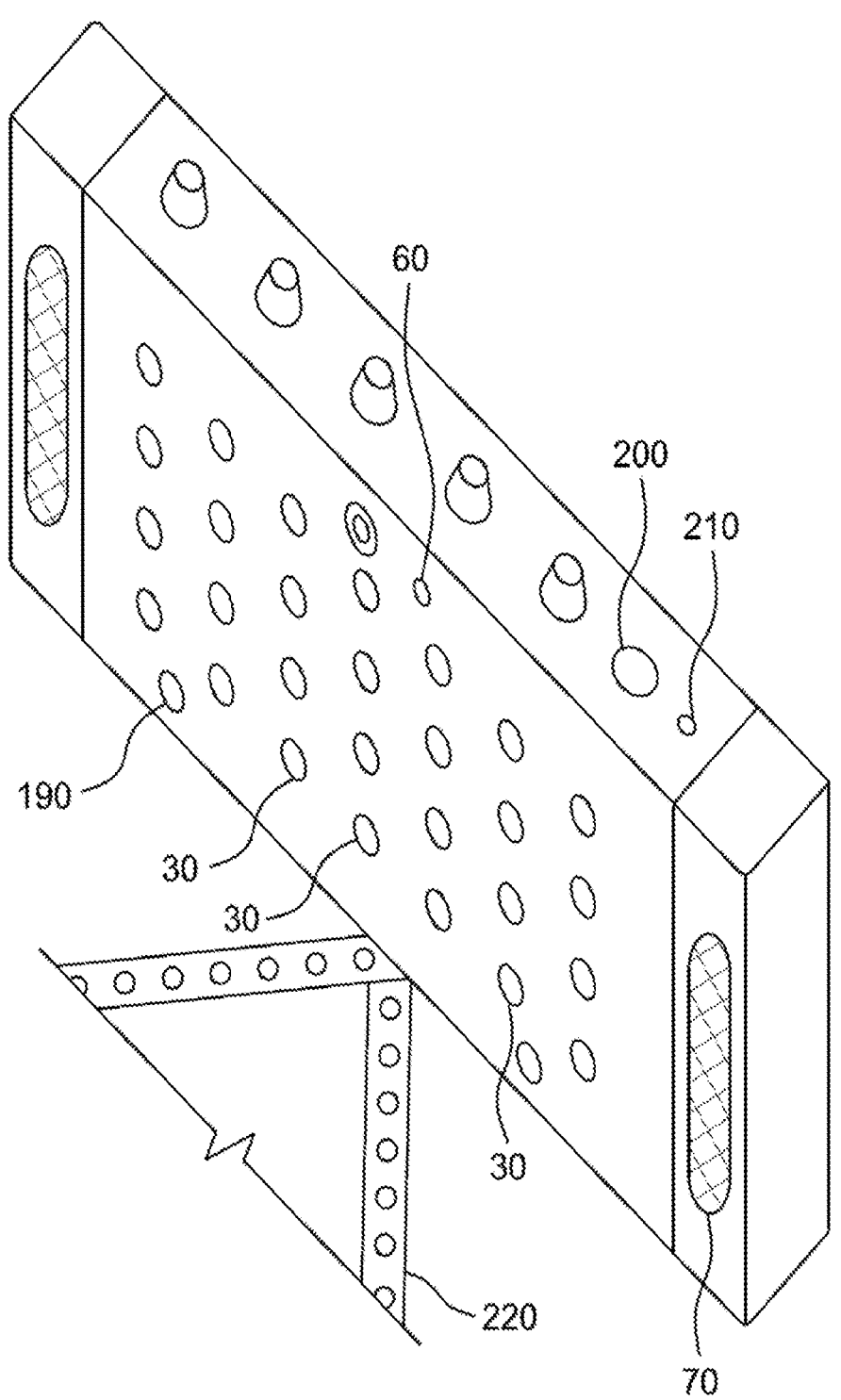

FIG. 9 schematically depicts another embodiment of an electromagnetic radiation-emitting device in accordance with the present inventive subject matter.

Figure 10:
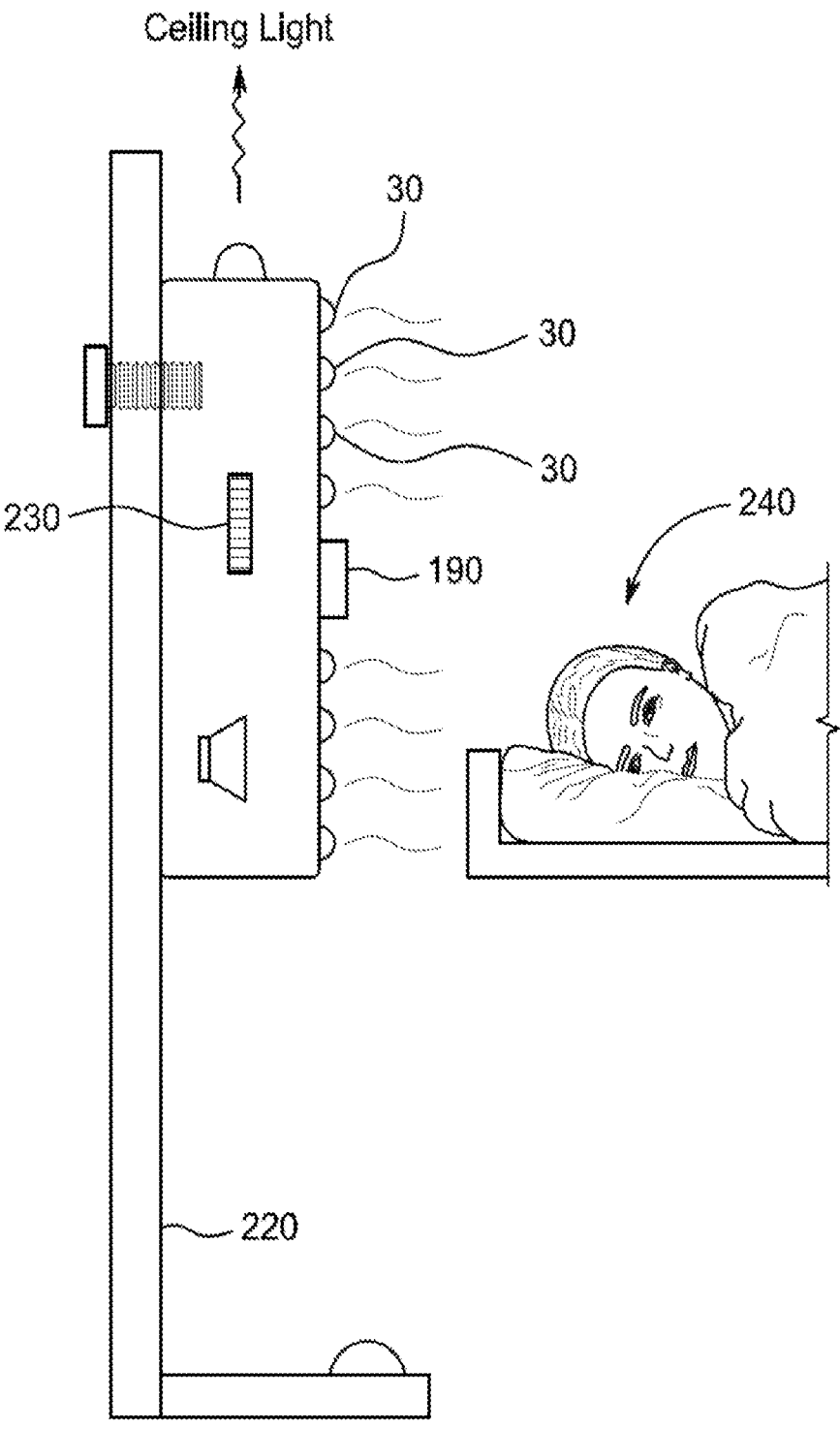

FIG. 10 schematically depicts an embodiment of an electromagnetic radiation-emitting device (which includes a bracket) in accordance with the present inventive subject matter, with a person's head near the electromagnetic radiation-emitting device.

Figure 11:
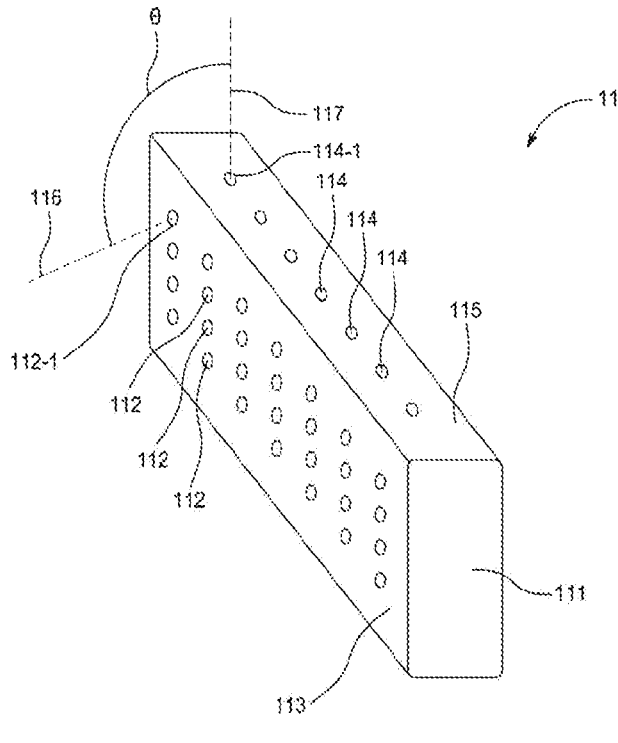

FIG. 11 depicts an embodiment of a device 110 that is within the scope of this twelfth aspect. The device 110 comprises a plurality of electromagnetic radiation emitters and a mounting structure 111.

Figure 12:
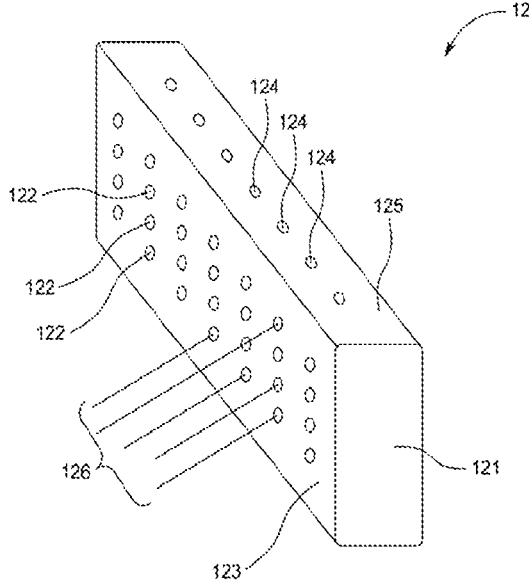

FIG. 12 schematically depicts an embodiment of a device described herein, which comprises a plurality of electromagnetic radiation emitters and a mounting structure 121.

DETAILED DESCRIPTION

Apparatuses and methods for use in treating central nervous system disorders with light at various wavelengths are disclosed. Representative central nervous system disorders include cognitive, motor, and behavioral/mood disorders. In some embodiments, combinations of wavelengths of light are used. In some aspects of these embodiments, light at a first wavelength is administered at a wavelength that provides anti-inflammatory effects, and light at a second wavelength is administered at a wavelength that provides increased vascularization, by promoting endogenous NO production and/or release within the brain.

The present invention will be better understood with reference to the following definitions.

Definitions

The expression "electromagnetic radiation-emitting device incapable of emitting near infrared light having a radiosity of greater than 50 mW/cm$^2$," means that no matter what electrical energy (voltage and current) is supplied to the electromagnetic radiation-emitting device, the electromagnetic radiation-emitting device does not emit near infrared light having a radiosity of greater than 50 mW/cm$^2$ (and the expression does not mean that the electromagnetic radiation-emitting device cannot emit other electromagnetic radiation, i.e., electromagnetic radiation other than near infrared radiation at any radiosity, i.e., "electromagnetic radiation-emitting device incapable of emitting near infrared light having a radiosity of greater than 50 mW/cm$^2$" encompasses (1) devices (and components) that emit only near infrared light, as well as (2) devices (and components) that are capable of emitting near infrared light and radiation of wavelength that is outside the wavelength range of near infrared light.

The expression "electromagnetic radiation-emitting device configured to emit electromagnetic radiation comprising near infrared light having a radiosity of at least 1 mW/cm$^2$," means that there is a magnitude of electrical energy (voltage and current) that can be supplied to the electromagnetic radiation-emitting device at which the electromagnetic radiation-emitting device would emit near infrared light having a radiosity of at least 1 $mW/cm^2$ (and the expression does not mean that electromagnetic radiation-emitting device cannot emit other electromagnetic radiation, i.e., electromagnetic radiation other than near infrared radiation at any radiosity, i.e., electromagnetic radiation-emitting device configured to emit electromagnetic radiation comprising near infrared light having a radiosity of at least 1 $mW/cm^2$" encompasses (1) devices (and components) that emit only near infrared light and devices (and components) that emit near infrared light, as well as (2) devices (and components) that are capable of emitting near infrared light and radiation of wavelength that is outside the wavelength range of near infrared light.

The expression "emitter," means any component or device (e.g., an LED) that is configured to emit electromagnetic radiation.

The expression "on," as used herein (e.g., in the expression "the first electromagnetic radiation emitter (1) is on . . . the first furnishing"), means that the first structure which is "on" a second structure can be in contact with the second structure, or can be separated from the second structure by one or more intervening structures (each side, or opposite sides, of which is/are in contact with the first structure, the second structure or one of the intervening structures).

The expression "partially in," as used herein (e.g., in the expression "the first electromagnetic radiation emitter . . . (2) is partially in . . . the first furnishing") means that part of the first structure (which is "partially in" a second structure) is in an indented region (i.e., a recess, a concave space, a groove, etc.) of the second structure.

The expression "entirely in," as used herein (e.g., in the expression the first electromagnetic radiation emitter . . . (3) is entirely in the first furnishing") means that the entirety of the first structure (which is "entirely in" a second structure) is in an indented region (i.e., a recess, a concave space, a groove, etc.) of the second structure.

The expression "sensor," means any sensor or detector (which can be a device or a component), including but not limited to identity sensors, human sensors, characteristics sensors, head sensors, head orientation sensors, face sensors, brain wave sensors, pulse sensors, respiration sensors, body temperature sensors, blood pressure sensors, oxygenation sensors, skin resistance sensors, skin temperature sensors, movement sensors, eye status sensors, body movement sensors, apparel detectors, ambient temperature sensors, ambient humidity sensors, ambient noise sensors, global positioning sensors, ambient light sensors, motion detectors, cameras, and microphones. Persons of skill in the art are familiar with such sensors, and such sensors are available, and any such sensor can be used as a sensor in accordance with the present inventive subject matter.

The expression "detection range," means a distance that a person or item can be spaced from a sensor or detector and the detector can sense or detect the phenomenon, characteristic or parameter (that the sensor or detector is configured to sense or detect) for the person or item.

The expression "identity sensor," means a device or component that [i] detects whether a particular human is within a detection range of the identity sensor, and/or [ii] determines the identity of a person who is within the detection range of the identity sensor.

The expression "human sensor," means a device or component that detects whether any human is within a detection range of the human sensor.

The expression "characteristics sensor," means a device or component that detects whether a human in a detection range of the characteristics sensor has a characteristic or set of characteristics (e.g., facial characteristics or size characteristics) that match a stored characteristic or stored set of characteristics.

The expression "head sensor," means a device or component that detects whether a human head is within a detection range of the identity sensor.

The expression "head orientation sensor," means a device or component that detects an orientation of a human head relative to the head orientation sensor.

The expression "face sensor," means a device or component that detects whether a human face is within a detection range of the identity sensor.

The expression "weight sensor," means a device or component that detects the weight of an object or a person on a surface or a structure (and/or whether or not an object equal to or exceeding a particular weight is on a surface or a structure).

The expression "brain wave sensor," means a device or component that detects brain waves of a person in a defined space relative to the brain wave sensor.

The expression "pulse sensor," means a device or component that detects the pulse of a person in a defined space relative to the pulse sensor.

The expression "respiration sensor," means a device or component that detects the respiration of a person in a defined space relative to the respiration sensor.

The expression "body temperature sensor," means a device or component that detects the body temperature of a person in a defined space relative to the respiration sensor.

The expression "blood pressure sensor," means a device or component that detects the blood pressure of a person in a defined space relative to the blood pressure sensor.

The expression "oxygenation sensor," means a device or component that detects the oxygenation of a person in a defined space relative to the respiration sensor.

The expression "skin resistance sensor," means a device or component that detects skin resistance of a person in a defined space relative to the skin resistance sensor.

The expression "skin temperature sensor," means a device or component that detects skin temperature of a person in a defined space relative to the skin temperature sensor.

The expression "movement sensor," means a device or component that detects movement of a person in a defined space relative to the movement sensor.

The expression "vibration sensor," means a device or component that detects vibration, e.g., vibration of at least a particular magnitude (e.g., which can be selected).

The expression "impact sensor," means a device or component that senses impact (e.g., first pounding, hand slapping, foot kicking, etc.).

The expression "eye status sensor," means a device or component that detects the eye status of a person in a defined space relative to the eye status sensor, e.g., whether either of the person's eyes is open, closed, blinking, frequency of blinking, duration of an eye being closed during a sequence, duration of an eye being open during a sequence.

The expression "body movement sensor," means a device or component that detects specific body movements of a person in a defined space relative to the body movement sensor, e.g., rolling over, arm moving, leg moving, chest movement, flinching, finger rubbing an eye, gesture (e.g., hand-waving, head nodding, etc.), repetitive motion (e.g., restlessness), etc.

The expression "apparel detector," means a device or component that detects whether a person in a defined space relative to the apparel detector is wearing a particular garment or piece of apparel, e.g., a hat, eyeglasses, eye covers, earplugs, etc.

The expression "ambient temperature sensor," means a device or component that detects temperature in a defined ambient space relative to the ambient temperature sensor.

The expression "ambient humidity sensor," means a device or component that detects humidity in a defined ambient space relative to the ambient humidity sensor.

The expression "ambient light sensor," means a device or component that detects light (e.g., whether there is light of a particular wavelength or in a particular wavelength range, radiosity of light, radiosity of a specific wavelength or wavelength range) incident on the ambient light sensor.

The expression "ambient noise sensor," means a device or component that detects noise (e.g., whether there is noise of a particular wavelength or in a particular wavelength range, amplitude of noise, amplitude of a specific wavelength or wavelength range) at the ambient noise sensor.

The expression "GPS" (or "global positioning sensor"), means a device or component that detects the position of the sensor relative to the earth. Persons of skill in the art are familiar with such sensors, and such sensors are available, and any such sensor can be used as a GPS in accordance with the present inventive subject matter.

The expression "motion detector," means a device or component that detects motion of a person in a defined space relative to the motion detector. Persons of skill in the art are familiar with such detectors, and such detectors are available, and any such detector can be used as a motion detector in accordance with the present inventive subject matter.

The expression "camera," means a device or component that detects (and optionally also records, e.g., digitally) visual images as they appear from the vantage point of the camera. Persons of skill in the art are familiar with cameras, and such cameras are available, and any such device or component can be used as a camera in accordance with the present inventive subject matter.

The expression "microphone," means a device or component that detects (and optionally also records, e.g., digitally) sounds as they are received at the location of the microphone. Persons of skill in the art are familiar with microphones, and such microphones are available, and any such device or component can be used as a microphone in accordance with the present inventive subject matter.

The expression "plane that is tangential to the first point" with regard to a surface (and similar expressions) refers to a plane that is the most tangential to the particular point. That is, even if a point does not have a perfectly tangential plane (and perhaps no plane that is even close to being perfectly tangential), a tangential plane can be defined by an imaginary segment of a plane that is circular and that has a diameter of 1 cm, and that is touching the surface at the center of the circle, and where the circle is divided into six equally sized (60 degree) slices, and for each slice, the sum of the distances between the slice and the surface at locations that are 0.25 cm, 0.50 cm, 0.75 cm and 1 cm from the center of the circle along line segments defined by the edges of the slice and along three line segments that divide the slice into four equal sub-slices (i.e., at 15 degrees, 30 degrees and 45 degrees) is equal to a total value for the slice, and the sum of: the total value for the first slice divided by the total value for the second slice, the total value for the second slice divided by the total value for the third slice, the total value for the third slice divided by the total value for the fourth slice, the total value for the fourth slice divided by the total value for the fifth slice, the total value for the fifth slice divided by the total value for the sixth slice, and the total value for the sixth slice divided by the total value for the first slice, is minimized.

The expression "actuator," means a device or structure that is configured to be actuated by being pressed (e.g., a pushbutton or a lever), or by receiving an electronic signal.

The expression "attachment feature," refers to any structure, attribute or material (or combination of one or more structures, and/or one or more attributes, and/or one or more materials) that is/are capable of holding an electromagnetic radiation-emitting device in place relative to a structure on which the attachment feature is located (or to which the attachment feature is attached). Representative examples of attachment features include suction cups, adhesives, magnets, screw holes and bolt holes.

The expression "direction," as used herein (e.g., in the expression "the first ray axis of emission extending in a first direction") refers to an orientation of a line (or line segment or ray) and any other line (or line segment or ray) that is parallel therewith, i.e., for any two directions, there is a single value for an acute angle defined by the two directions (except where the two directions are the same or define right angles with respect to each other).

The expression "determine an identity of a person who is in a detection range for the first sensor" (or the like) means that a device can determine identity of at least one person, not necessarily of every person.

The expression "configured to emit" (e.g., in the expression "the first electromagnetic radiation emitter configured to emit electromagnetic radiation comprising NIR having a radiosity of at least 1 mW/cm$^2$" means the device that is "configured to emit" has a power line (to which power can be supplied to supply power to the device), and when line voltage is supplied to the power line, characteristics that are described as characteristics for which the device is configured will occur (e.g., radiosity at the first location will be in the range of 0.5 mW/cm$^2$ to 5 mW/cm$^2$). (The expression "line voltage" is used herein in accordance with its well-known usage to refer to standard electricity (120 V) supplied by an energy source, e.g., electricity supplied from a grid, including AC and DC.)

The expression "ray axis of emission", as used herein in connection with light output from one or more electromagnetic radiation emitters, means a ray originating at the electromagnetic radiation emitter and extending in a direction of maximum brightness of light emission, or a mean direction of light emission (in other words, in the case of mean direction of light emission, (1) if there is provided a light emitter in which the distribution of the brightness of emitted light is non-Lambertian, e.g., if the distribution of the brightness of emitted light is doughnut-shaped (e.g., the light emitter might itself be toroidal or annular, or a plurality of light emitters might be arranged in a toroidal or annular pattern), e.g., with directions of maximum brightness extending around the doughnut shape in the form of a circle extending about a polar axis, e.g., at about 120 vertical degrees (and extending around the entire 360 lateral degrees, i.e., to define a circle) in a Type C coordinate system, i.e., in which the polar axis is vertical, vertical angles range from 0 degrees (nadir) to 180 degrees (zenith) (90 vertical degrees being equatorial), and lateral angles range from 0 degrees to 360 degrees, the ray axis of emission might coincide with the vertical axis (e.g., because the mean direction of the maxima lies on the vertical axis), even though the maximum directions of brightness do not themselves lie on the vertical axis, or (2) if the maximum brightness is in a first direction, but a brightness in a second direction ten (or fifty) degrees to one side of the first direction is larger than a brightness in a third direction ten (or fifty) degrees to an opposite side of the first direction, the mean direction of light emission would be moved somewhat toward the second direction as a result of the brightnesses in the second direction and the third direction).

The expression "independently" (e.g., in the expression "one or more of the electromagnetic radiation emitters to emit electromagnetic radiation, independently of whether any other of the electromagnetic radiation emitters is emitting electromagnetic radiation"), means that a device can be operated in such a way that one or more of the electromagnetic radiation emitters can emit electromagnetic radiation while one or more others of the electromagnetic radiation emitters are not emitting electromagnetic radiation, and/or that whether one or more electromagnetic radiation emitters is emitting electromagnetic radiation (and/or is changing with regard to whether it is emitting electromagnetic radiation) is not affected by (or restricted by) whether one or more other electromagnetic radiation emitters is emitting electromagnetic radiation.

The expression "cognitive activity," refers to activity that requires some level of thinking, e.g., a higher level of thinking, e.g., meeting with people, carrying out chores, solving mathematical questions, working puzzles, playing games, etc.

The expression "radius of curvature," means (e.g., at a point of a surface where a cross-section of the surface corresponds precisely to a portion of a circle) the radius of a circle that touches the cross-section of the surface at such point and has the same tangent and curvature at that point. In situations where a cross-section of a region of a surface between a first substantially flat portion and a second substantially flat portion (e.g., a cross-section of an edge between two substantially flat portions of a protrusion) is not precisely circular and/or is not continuously curved:

the radius of curvature of such region of such surface means the radius of a circle that has a first point (having a first tangent) and a second point (having a second tangent), where [1] the first tangent defines an angle with respect to the second tangent that equals an angle that the first substantially flat region makes relative to the second substantially flat region, and [2] respective points on the first substantially flat portion and the second substantially flat portion that are closest to each other are spaced from each other by a distance that is substantially equal to the distance that the first point on the circle is spaced from the second point on the circle, and/or the radius of curvature of a portion of such cross-section of a region of such surface, such portion extending from a first location on the surface to a second location on the surface, means the radius of a circle that has a first point (having a first tangent) and a second point (having a second tangent), where [3] the first tangent defines an angle with respect to the second tangent that is substantially equal to an angle defined by a tangent of the first location relative to a tangent of the second location, and [4] the first location is spaced from the second location by a distance that is substantially equal to the distance that the first point on the circle is spaced from the second point on the circle.

The present inventive subject matter encompasses many combinations of elements and features. The expression "In some embodiments, which can include or not include, as suitable, any of the other features described herein," or the like, is used in the present specification to introduce elements and/or features of the present inventive subject matter that can be included or not included in any particular embodiment, i.e., elements and/or features that can be combined in any suitable way. In other words, the present inventive subject matter encompasses all combinations of elements and/or features that are introduced with the expression "In some embodiments in accordance with the present inventive subject matter, which can include or not include, as suitable, any of the other features described herein," or the like.

A light emitting diode ("LED") is a combination of one or more LED components including, but not limited to, an electroluminescent semiconductor material, a substantially translucent package, an electric current conductor, an electric voltage insulator, a photon emission path, a power supply, a LED heat sink, an array of electroluminescent semiconductor material, an addressable array of electroluminescent semiconductor material, a bonding material, a wire-bonding material, an LED component fastener, and a LED integrated circuit. The photon emission path is comprised of one or more combinations of photon emission path components including, but not limited to, a translucent optical lens, and a wavelength dependent photonic filter. LEDs are selected from one or more LED types including, but not limited to, laser diode, organic light emitting devices, periodic table of the elements group IV based semiconductor LED type, periodic table of the elements group III-V based semiconductor LED type, periodic table of the elements group II-VI based semiconductor LED type, optically pumped LED type, electrically pumped LED type, and organic light emitting device type. Group IV element based LED types include, but are not limited to, germanium, silicon, carbon nanotube, silicon carbide ("SiC"), and diamond-based LED types. Group III-V LED types includes, but are not limited to, aluminum nitride ("AlN"), gallium nitride ("GaN"), aluminum phosphide ("AlP"), gallium phosphide ("GaP"), aluminum selenide ("AlSe"), gallium selenide ("GaSe"), and aluminum indium gallium nitride ("AlInGaN") based LED types. Group II-VI LED types include, but are not limited to, zinc oxide, zinc sulfide, zinc selenide, zinc telluride, cadmium oxide, cadmium sulfide, cadmium selenide, and cadmium telluride based LED types. The exact stochastic ratios of elements and doping processes are well-known in the literature and do not need to be re-iterated herein.

The devices and methods are described in more detail below.

I. Passive Therapy

In one embodiment of the devices described herein, light is administered to a subject in need of treatment without the device physically coming into contact with the subject. Such therapy is passive as it can occur without an intentional treatment effort by the user. Such passive approaches have many benefits, but especially is beneficial in therapy compliance. Various embodiments of devices which emit electromagnetic radiation are discussed below. These devices are particularly advantageous as they can inure therapeutic benefit without relying on therapeutic compliance.

In each embodiment, the device can comprise any suitable component or feature (including any combination thereof) described in connection with any aspect of the present inventive subject matter. For example, the device can be configured to be mounted on, partially in, or completely within, a furnishing (e.g., a bed a chair, a mattress, a pillow, etc.).

The devices are useful in a variety of ways, one of which is to provide treatments, such as NIR treatments, and/or light at other wavelengths, that are tailored to specific characteristics of the user and/or the environment, in a way that is not intrusive or annoying to the user/patient (thereby increasing the likelihood of compliance). Because the devices are not attached to the user/patient, this can allow the user/patient to engage in other activities, which is one way the devices can increase the likelihood of compliance.

Where the devices include a sensor, the sensor can be any type of sensor. Representative sensors include an identity sensor, a human sensor, a characteristics sensor, a head sensor, a head orientation sensor, a face sensor, a weight sensor, a brain wave sensor, a pulse sensor, a respiration sensor, a body temperature sensor, a blood pressure sensor, an oxygenation sensor, skin resistance sensor, a skin temperature sensor, a movement sensor, a vibration sensor, an impact sensor, an eye status sensor, a body movement sensor, an apparel detector, an ambient temperature sensor, an ambient humidity sensor, an ambient light sensor, an ambient noise sensor, a GPS (global positioning sensor), a motion detector, a camera, and/or a microphone, each type of sensor as defined herein.

In a first aspect, the device is an electromagnetic radiation-emitting device that does not come into physical contact with a subject, and that comprises: at least a first electromagnetic radiation emitter; and at least a first sensor, the first electromagnetic radiation emitter configured to emit electromagnetic radiation comprising near infrared light (referred to herein as "NIR") having a radiosity of at least 1 mW/cm$^2$ (in some embodiments at least 2 mW/cm$^2$, at least 3 mW/cm$^2$, at least 4 mW/cm$^2$, at least 5 mW/cm$^2$, at least 6 mW/cm$^2$, at least 7 mW/cm$^2$, at least 8 mW/cm$^2$, at least 9 mW/cm$^2$, at least 10 mW/cm$^2$, at least 12 mW/cm$^2$, at least 15 mW/cm$^2$, at least 20 mW/cm$^2$, at least 25 mW/cm$^2$, at least 30 mW/cm$^2$, at least 35 mW/cm$^2$, at least 40 mW/cm$^2$, or at least 45 mW/cm$^2$), said first electromagnetic radiation emitter incapable of emitting NIR having a radiosity of greater than 50 mW/cm$^2$ (in some embodiments, 45 mW/cm$^2$, 40 mW/cm$^2$, 35 mW/cm$^2$, 30 mW/cm$^2$, 25 mW/cm$^2$, 20 mW/cm$^2$, 15 mW/cm$^2$, 12 mW/cm$^2$, 10 mW/cm$^2$, 9 mW/cm$^2$, 8 mW/cm$^2$, 7 mW/cm$^2$, 6 mW/cm$^2$, 5 mW/cm$^2$, 4 mW/cm$^2$, 3 mW/cm$^2$, or 2 mW/cm$^2$).

The treatments can be tailored to specific characteristics of the user and/or the environment, and/or that achieve exceptional user/patient compliance.

In some embodiments, the first sensor is a head orientation sensor, the electromagnetic radiation-emitting device comprises a plurality of electromagnetic radiation emitters, including said first electromagnetic radiation emitter, and the electromagnetic radiation-emitting device adjusts which of the plurality of electromagnetic radiation emitters emits NIR and/or respective luminosities of NIR emitted by the plurality of electromagnetic radiation emitters based on an orientation of a person's head detected by the first sensor.

In some aspects of these embodiments, based on the orientation of the person's head, the electromagnetic radiation-emitting device adjusts which of the plurality of electromagnetic radiation emitters emits NIR and/or respective luminosities of NIR emitted by the plurality of electromagnetic radiation emitters in order to give a substantially uniform dosage around the person's brain (or a specific variance of dosage around the person's brain), or to deliver NIR to a particular part (or parts) of the person's brain.

In a second aspect, the device comprises: at least first, second, third, fourth and fifth electromagnetic radiation emitters, each of the first, second, third, fourth and fifth electromagnetic radiation emitters configured to emit NIR, the electromagnetic radiation-emitting device configured to emit electromagnetic radiation comprising NIR having a radiosity in the range of from about 0.5 mW/cm$^2$ to about 5 mW/cm$^2$ at a first location, the first location spaced from the electromagnetic radiation-emitting device by a distance of 10 cm or more.

In some embodiments, the device comprises not more than 60 electromagnetic radiation emitters.

In a third aspect, the device comprises: at least a first electromagnetic radiation emitter; and at least a first sensor, wherein the first electromagnetic radiation emitter configured to emit electromagnetic radiation comprising NIR.

In some embodiments: the first sensor is an identity sensor, the electromagnetic radiation-emitting device is configured to store treatment information comprising dates and times of NIR treatments administered to respective persons, and dosages of NIR administered to respective persons during NIR treatments, the electromagnetic radiation-emitting device is configured to store regimen information comprising desired agendas for NIR treatments to be administered to respective persons, the electromagnetic radiation-emitting device is configured to determine an identity of a first person who is in a detection range for the first sensor, the electromagnetic radiation-emitting device is configured to determine whether the first person is in need of an NIR treatment, and if so, the NIR treatment that should be administered to the first person, based on the detected identity of the first person, treatment information for the first person stored in the electromagnetic radiation-emitting device and regimen information stored in the electromagnetic radiation-emitting device for the first person, and/or the electromagnetic radiation-emitting device is configured to administer a desired NIR treatment and/or treatment at other wavelengths to the first person, if the electromagnetic radiation-emitting device determines that the first person is in need of an NIR treatment, said desired NIR treatment based on the detected identity of the first person, the treatment information for the first person stored in the electromagnetic radiation-emitting device and the regimen information stored in the electromagnetic radiation-emitting device for the first person.

In some embodiments: the first sensor is an identity sensor, the electromagnetic radiation-emitting device is configured to determine an identity of a first person who is in a detection range for the first sensor, based on information from the identity sensor, the electromagnetic radiation-emitting device is configured to store regimen information comprising desired NIR treatments to be administered to respective persons, the electromagnetic radiation-emitting device is configured to determine whether an NIR treatment should be administered to the first person, based on a determined identity of the first person, and the electromagnetic radiation-emitting device is configured to administer a desired NIR treatment to the first person, based on a determined identity of the first person and stored regimen information for the first person, if the electromagnetic radiation-emitting device determines that an NIR treatment should be administered to the first person.

In some embodiments: the electromagnetic radiation-emitting device is configured to receive input person identification comprising an input identity of a first person, the electromagnetic radiation-emitting device is configured to store treatment information comprising dates and times of NIR treatments administered to respective persons, and dosages of NIR administered to respective persons during NIR treatments, the electromagnetic radiation-emitting device is configured to store regimen information comprising desired agendas for NIR treatments to be administered to respective persons, the electromagnetic radiation-emitting device is configured to determine whether the first person is in need of an NIR treatment, and if so, the NIR treatment that should be administered to the first person, based on the identity of the first person, treatment information for the first person stored in the electromagnetic radiation-emitting device and regimen information stored in the electromagnetic radiation-emitting device for the first person, and the electromagnetic radiation-emitting device is configured to administer a desired NIR treatment to the first person, if the electromagnetic radiation-emitting device determines that the first person is in need of an NIR treatment, said desired NIR treatment based on the input identity of the first person, the treatment information for the first person stored in the electromagnetic radiation-emitting device and the regimen information stored in the electromagnetic radiation-emitting device for the first person.

In some embodiments: the electromagnetic radiation-emitting device is configured to receive input person identification comprising an input identity of a first person, the electromagnetic radiation-emitting device is configured to store regimen information comprising desired NIR treatments to be administered to respective persons, and the electromagnetic radiation-emitting device is configured to administer a desired NIR treatment to the first person, based on the input identity of the first person and stored regimen information for the first person.

In some embodiments according to the third aspect of the present inventive subject matter, which can include or not include, as suitable, any of the other features described herein: the first sensor is configured to detect a first person in a detection range for the first sensor, and the electromagnetic radiation-emitting device is configured to administer an NIR treatment to the first person upon the first sensor detecting that the first person is in the detection range for the first sensor.

In some embodiments, the first sensor is selected from the group of sensors consisting of human sensors, head sensors, head orientation sensors, face sensors, movement sensors, eye status sensors, body movement sensors and weight sensors.

In some embodiments: the electromagnetic radiation-emitting device is configured to store treatment information comprising dates and times of NIR treatments that have been administered, and dosages of NIR administered to respective persons during NIR treatments, the electromagnetic radiation-emitting device is configured to store regimen information, the first sensor is configured to detect a first person in a detection range for the first sensor, the electromagnetic radiation-emitting device is configured to determine whether the first person is in need of an NIR treatment, and if so, the NIR treatment that should be administered to the first person, based on the treatment information stored in the electromagnetic radiation-emitting device and the regimen information, and the electromagnetic radiation-emitting device is configured to administer a desired NIR treatment to the first person, if the electromagnetic radiation-emitting device determines that the first person is in need of an NIR treatment, said desired NIR treatment based on the treatment information stored in the electromagnetic radiation-emitting device and the regimen information. In some of such embodiments, the first sensor is selected from the group of sensors consisting of human sensors, head sensors, head orientation sensors, face sensors, movement sensors, eye status sensors, body movement sensors and weight sensors.

In a fourth aspect, the device comprises: at least a first electromagnetic radiation emitter; and at least a first sensor, the first electromagnetic radiation emitter configured to emit electromagnetic radiation comprising at least one type of radiation selected from the group of radiation types consisting of (1) visible light comprising at least one wavelength in the range of from 490 nm to 500 nm and (2) near ultraviolet light (referred to herein as "near UV light").

The devices are useful in a variety of ways, one of which is to provide specific electromagnetic radiation treatments that provide useful effects on persons.

In a fifth aspect, the device comprises: at least a first mounting structure; and at least a first electromagnetic radiation emitter, the first electromagnetic radiation emitter configured to emit electromagnetic radiation comprising red visible light, every electromagnetic radiation emitter that emits red visible light is mounted on at least one of the at least a first mounting structure, respective ray axes of emission of every electromagnetic radiation emitter that emits red visible light not passing through any of the at least a first mounting structure.

The devices are useful in a variety of ways, one of which is to provide red light treatments in a way that is not intrusive or annoying to the user/patient (thereby increasing the likelihood of compliance).

In some, the electromagnetic radiation-emitting device further comprises at least a first sensor. In some of such embodiments, the sensor is at least 50 mm from an object (e.g., a person) being irradiated with the red visible light.

In a sixth aspect, the device comprises: at least a first electromagnetic radiation emitter; and at least a first actuator, the first electromagnetic radiation emitter configured to emit electromagnetic radiation comprising red visible light upon the first actuator being actuated. In some embodiments, the first actuator is a pushbutton, and in other embodiments, is a timer.

In a seventh aspect, the device comprises: at least a first electromagnetic radiation emitter; and at least a first attachment feature, the first electromagnetic radiation emitter configured to emit electromagnetic radiation comprising NIR, the at least a first attachment feature configured to hold the electromagnetic radiation-emitting device relative to a first structure that comprises first and second surfaces, the second surface parallel to the first surface, the second surface spaced from the first surface by a first distance, the first distance in the range of from 1 cm to 8 cm.

In some embodiments, the first and second surfaces are on a furnishing selected from the group of furnishings consisting of bed headboards and chair backs.

In some embodiments, the first distance is in a range of from 2 cm to 8 cm, from 3 cm to 8 cm, from 4 cm to 8 cm, from 5 cm to 8 cm, from 6 cm to 8 cm, from 7 cm to 8 cm, from 1 cm to 7 cm, from 2 cm to 7 cm, from 3 cm to 7 cm, from 4 cm to 7 cm, from 5 cm to 7 cm, from 6 cm to 7 cm, from 1 cm to 6 cm, from 2 cm to 6 cm, from 3 cm to 6 cm, from 4 cm to 6 cm, from 5 cm to 6 cm, from 1 cm to 5 cm, from 2 cm to 5 cm, from 3 cm to 5 cm, from 4 cm to 5 cm, from 1 cm to 4 cm, from 2 cm to 4 cm, from 3 cm to 4 cm, from 1 cm to 3 cm, from 2 cm to 3 cm, or from 1 cm to 2 cm.

In an eighth aspect, the device comprises: at least a first electromagnetic radiation emitter; and at least a first attachment feature, the first electromagnetic radiation emitter configured to emit electromagnetic radiation comprising NIR, the first attachment feature selected from the group of attachment features consisting of suction cups, adhesives, magnets, screw holes and bolt holes.

In a ninth aspect, the device comprises a plurality of electromagnetic radiation emitters, said plurality of electromagnetic radiation emitters comprising: at least a first NIR emitter, the first NIR emitter configured to emit electromagnetic radiation comprising NIR, at least a first infrared light (referred to herein as "IR light") emitter, the first IR light emitter configured to emit electromagnetic radiation comprising IR light; and at least a first UV light emitter, the first UV light emitter configured to emit electromagnetic radiation comprising UV light.

The devices can provide specific electromagnetic radiation treatments (involving different types of radiation, e.g., which can include NIR and IR, NIR and UV, IR and UV, or NIR, IR and UV, and optionally also visible light, simultaneously, sequentially or a combination of simultaneous and sequential) that provide useful effects on persons.

In some embodiments the device further comprises at least a first visible light emitter.

In some embodiments, the devices can include any of the other features described herein:

said electromagnetic radiation-emitting device further comprises a light-type selection element; and said light-type selection element is configured to enable a user to select one or more of the electromagnetic radiation emitters to emit electromagnetic radiation, independently of whether any other of the electromagnetic radiation emitters is emitting electromagnetic radiation, whereby the light-type selection element can be used to cause the electromagnetic radiation-emitting device to selectively emit any choice from among (1) NIR alone, (2) IR light alone, (3) UV light alone, (4) a combination consisting of NIR and IR light, (5) a combination consisting of NIR and UV light, (6) a combination consisting of IR light and UV light, and (7) a combination consisting of NIR, IR light and UV light.

In some of such embodiments: the electromagnetic radiation-emitting device further comprises at least a first visible light emitter, and said light-type selection element is further configured to enable a user to select one or more of the at least a first visible light emitter to emit visible light, independently of whether any other of the electromagnetic radiation emitters is emitting electromagnetic radiation, whereby the light-type selection element can be used to cause the electromagnetic radiation-emitting device to selectively emit any choice from among (1) NIR alone, (2) IR light alone, (3) UV light alone, (4) a combination consisting of NIR and IR light, (5) a combination consisting of NIR and UV light, (6) a combination consisting of IR light and UV light, (7) a combination consisting of NIR, IR light and UV light, (8) a combination consisting of NIR and visible light, (9) a combination consisting of IR light and visible light, (10) a combination consisting of UV light and visible light, (11) a combination consisting of NIR, IR light and visible light, (12) a combination consisting of NIR, UV light and visible light, (13) a combination consisting of IR light, UV light and visible light, (14) a combination consisting of NIR, IR light, UV light and visible light, and (15) visible light alone.

In a tenth aspect, the device comprises at least a first electromagnetic radiation emitter and at least a first furnishing selected from the group of furnishings consisting of pillows, mattresses, beds and chairs; the first electromagnetic radiation emitter may be configured to emit electromagnetic radiation comprising NIR, and the first electromagnetic radiation emitter (1) is on, (2) is partially in, or (3) is entirely in the first furnishing.

In an eleventh aspect, the device comprises: a plurality of electromagnetic radiation emitters; and a color temperature selection element, the plurality of electromagnetic radiation emitters comprising: at least a first electromagnetic radiation emitter that is configured to emit electromagnetic radiation that comprises NIR; and at least a first variable-color-temperature emission element that comprises one or more variable-color-temperature emission element emitters, said color temperature selection element to enable a user select a desired color temperature from among at least two selectable color temperatures, whereby the color temperature selection element can be used to cause the electromagnetic radiation-emitting device to emit visible light of a color temperature of any of the at least two selectable color temperatures.

The devices can provide specific electromagnetic radiation treatments (including NIR, visible light of one or more color temperature, or a combination of NIR and visible light of one or more color temperature, simultaneously, sequentially or a combination of simultaneous and sequential) that provide useful effects on persons.

In some embodiments, the devices can include or not include, as suitable, any of the following features: the electromagnetic radiation-emitting device further comprises a light-type selection element, and the light-type selection element is configured to enable a user to select one or more of the electromagnetic radiation emitters to emit electromagnetic radiation, independently of whether any other of the electromagnetic radiation emitters is emitting electromagnetic radiation, whereby the color temperature selection element and the light-type selection element can be used to cause the electromagnetic radiation-emitting device to selectively emit any choice from among (1) visible light of at least one desired color temperature selected from among the at least two selectable color temperatures alone, (2) NIR alone, and (3) a combination consisting of visible light of at least one desired color temperature selected from among the at least two selectable color temperatures and NIR.

In some embodiments, the color temperature selection element and the first variable-color-temperature emission element are configured to enable a user to select one or more desired color temperatures from among at least first through ninth color temperatures, the first color temperature in a range of from 1,000 K to 2,000 K, the second color temperature in a range of from 2,000 K to 3,000 K, the third color temperature in a range of from 3,000 K to 4,000 K, the fourth color temperature in a range of from 4,000 K to 5,000 K, the fifth color temperature in a range of from 5,000 K to 6,000 K, the sixth color temperature in a range of from 6,000 K to 7,000 K, the seventh color temperature in a range of from 7,000 K to 8,000 K, the eighth color temperature in a range of from 8,000 K to 9,000 K, and the ninth color temperature in a range of from 9,000 K to 10,000 K.

In a twelfth aspect, the device comprises a plurality of electromagnetic radiation emitters and at least a first mounting structure, said plurality of electromagnetic radiation emitters comprising at least a first NIR emitter and at least a first visible light emitter, the first NIR emitter configured and oriented to have a first ray axis of emission relative to the first mounting structure, the first ray axis of emission extending in a first direction, the first visible light emitter configured and oriented to have a second ray axis of emission relative to the first mounting structure, the second ray axis of emission extending in a second direction, the first direction defining an angle of at least 50 degrees relative to the second direction.

FIG. 11 depicts an embodiment of a device 110 that is within the scope of this twelfth aspect. The device 110 comprises a plurality of electromagnetic radiation emitters and a mounting structure 111. The plurality of electromagnetic radiation emitters comprises a plurality of NIR emitters 112 on a first surface 113 of the mounting structure 111, and a plurality of visible light emitters 114 on a second surface 115 of the mounting structure 111. A first of the NIR emitters 112-1 emits light that has a ray axis of emission 116, and a first of the visible light emitters 114-1 has emits light that has a ray axis of emission 117. The ray axis of emission 116 extends in a first direction, the ray axis of emission 117 extends in a second direction, and (in this embodiment) the first direction defines an angle of 90 degrees relative to the second direction.

In some embodiments, the devices can include or not include, as suitable, any of the following: each of a plurality of NIR emitters in the electromagnetic radiation-emitting device has a respective ray axis of emission that has a respective direction that is within 10 degrees of a first direction, each of a plurality of visible light emitters in the electromagnetic radiation-emitting device has a respective ray axis of emission that has a respective direction that is within 10 degrees of a second direction, and the first direction defines an angle of at least 50 degrees with respect to the second direction.

In some embodiments, the first mounting structure may comprise at least a first mounting structure surface and a second mounting structure surface, each of a plurality of NIR emitters in the electromagnetic radiation-emitting device are on the first mounting structure first surface, each of a plurality of visible light emitters in the electromagnetic radiation-emitting device are on the first mounting structure second surface, and the first mounting structure first surface defines an angle of at least 50 degrees with respect to the first mounting structure second surface.

In a thirteenth aspect, the devices comprise at least a first electromagnetic radiation emitter and at least a first person interaction element, the first electromagnetic radiation emitter configured to deliver NIR to a person in a first person treatment location, the first person interaction element configured to prompt a user in the first person treatment location to engage in cognitive activity.

The devices can provide one or a combination of effects that provide useful effects on persons suffering from AD or that provide useful effects on preventing AD or slowing progression of AD, as well as other cognitive disorders. The devices can also be used to treat, prevent, or slow the progression of, one or more of the motor disorders and/or behavioral/mood disorders discussed herein.

In some embodiments, the cognitive activity being enhanced by the treatments is selected from the group of cognitive activities consisting of (1) answering questions, (2) solving puzzles and (3) performing movements in response to visual and/or audible prompts.

In a fourteenth aspect, the device comprises at least a first mounting structure and at least a first electromagnetic radiation emitter, the first electromagnetic radiation emitter configured to emit electromagnetic radiation comprising NIR, the first mounting structure devoid of any region in which a first point is spaced from a second point by not more than 0.1 cm, not more than 0.2 cm, not more than 0.3 cm, not more than 0.4 cm, not more than 0.5 cm, not more than 0.7 cm, or not more than 1.0 cm, and a first line that is perpendicular to a first plane that is tangential to the first point defines an angle of more than 45 degrees, more than 60 degrees, or more than 75 degrees, relative to a second line that is perpendicular to a second plane that is tangential to the second point.

For example, the embodiment depicted in FIG. 11 is an electromagnetic radiation-emitting device 110 that comprises a first mounting structure 111 and a plurality of electromagnetic radiation emitters 112 that are configured to emit electromagnetic radiation comprising NIR, and the first mounting structure 111 is smooth enough that it is devoid of any region (that has a sharp edge or region) in which a first point is spaced from a second point by not more than 0.1 cm, and a first line that is perpendicular to a first plane that is tangential to the first point defines an angle of more than 60 degrees relative to a second line that is perpendicular to a second plane that is tangential to the second point. For example, moving from the first surface 113 to the second surface 115, upon moving from one point to any other point that is within 0.1 cm, the angle defined by a plane that is perpendicular to the first point and a plane that is perpendicular to the second point is, in every case, not more than 60 degrees.

By configuring the first mounting structure such that it is devoid of any region as discussed in any of the options described above, to a desired extent, the first mounting structure does not have any sharp corners or angles (or other regions), such that if a person (e.g., who may be sleeping) bumps into the first mounting structure (or crashes into the first mounting structure), the likelihood of the person being cut or otherwise injured is at a desired level. The devices can therefore minimize or avoid harm to the user/patient.

In a fifteenth aspect, the device comprises at least a first mounting structure; and a plurality of electromagnetic radiation emitters, the plurality of electromagnetic radiation emitters comprising at least a first group of electromagnetic radiation emitters, the first group of electromagnetic radiation emitters comprising at least 20 electromagnetic radiation emitters that are each configured to emit electromagnetic radiation comprising NIR, the first group of electromagnetic radiation emitters each having a respective tangential plane perpendicular to a respective ray axis of emission of the electromagnetic radiation emitter, each of the respective tangential planes defining an angle of not greater than 20 degrees relative to a first plane.

In a sixteenth embodiment, the devices used in the methods are laptops, cell phones, television or movie screens, which are adapted to provide light emissions at desired wavelengths. In some aspects, the light is provided at one or more desired wavelengths for a predetermined period of time. When the light is provided at more than one desired wavelength, the wavelengths can be emitted simultaneously or sequentially. As the user looks at the devices, the user is exposed to the desired irradiation.

In a seventeenth embodiment, the device is a shower or bath equipped with light sources which emit light at one or more desired wavelengths when the user is in the shower or bath. When the light is provided at more than one desired wavelength, the wavelengths can be emitted simultaneously or sequentially. As the user looks at the devices, the user is exposed to the desired irradiation. The light source can include an actuator or a timer to control how long the light is emitted.

In an eighteenth embodiment, the device is a light fixture equipped with light sources which emit light at one or more desired wavelengths when the user is in a room that includes the light fixture. Representative light fixtures include overhead lighting, lamps, and the like. When the light is provided at more than one desired wavelength, the wavelengths can be emitted simultaneously or sequentially. As the user looks at the devices, the user is exposed to the desired irradiation. The light source can include an actuator or a timer to control how long the light is emitted.

In a nineteenth embodiment, the device is an enclosure that the patient/user can sit in, where light is provided inside the disclosure such that it impinges on the patient/user. When the light is provided at more than one desired wavelength, the wavelengths can be emitted simultaneously or sequentially. The light source can include an actuator or a timer to control how long the light is emitted, and the light source can be turned on or off, for example, based on when the door is first opened and then closed, based on when the patient/user sits in a chair inside the enclosure, and the like. In this embodiment, a sensor can be a sensor that senses when the door has been opened, and then closed, or when someone sits in a chair/sofa within the enclosure, where light sources are positioned to impinge light on a patient/user when the patient/user sits in the chair/sofa.

One type of enclosure is the type disclosed in U.S. Pat. No. 9,919,162, which administers light therapy to a user positioned within an enclosure. In addition to light therapy, this type of enclosure allows one to co-administer aromatherapy, and also allows the user to ramp up, ramp down, or plateau the light source, alter the type of light source, type of audio source, type of aroma, amount of aroma, air temperature, air humidity, air ionization, air filtration, and time period while in the enclosure.

The devices can be used in methods which comprise delivering NIR from an NIR emitter to a head of a person, said NIR of a radiosity in the range of from 1 mW/cm² to 50 mW/cm², and sensing at least a first parameter on a first sensor. The devices used in these methods can include any sensor described herein. When used in connection with any of the devices described herein, each of the methods described in this section can further comprise mounting an electromagnetic radiation-emitting device comprising one or more electromagnetic radiation emitters on, partially in, or completely within, a furnishing (e.g., a bed a chair, a mattress, a pillow, etc.).

As with the devices, the methods are useful in a variety of ways, one of which is to provide treatments, such as NIR treatments or treatments with other wavelengths of light, that are tailored to specific characteristics of the user and/or the environment, and/or that achieve exceptional user/patient compliance.

In some embodiments of the methods described herein, the first parameter is selected from a group of parameters consisting of parameters of the person and ambient parameters in a region in which the person is located.

In another embodiment, the methods comprise delivering NIR from at least first, second, third, fourth and fifth electromagnetic radiation emitters to a head of a person, the head of the person spaced within 100 cm of each of the electromagnetic radiation emitters, whereby the radiosity of a combination of NIR incident on the head of the person from the first, second, third, fourth and fifth electromagnetic radiation emitters is in the range of from 0.5 mW/cm² to 5 mW/cm². In some embodiments, the methods comprise delivering NIR from not more than 60 electromagnetic radiation emitters to a head of a person.

In another embodiment, the methods comprise delivering NIR from an NIR emitter to a head of a person and sensing at least one parameter on a sensor selected from the group of sensors consisting of identity sensors, human sensors, characteristics sensors, head sensors, head orientation sensors, face sensors, weight sensors, brain wave sensors, pulse sensors, respiration sensors, body temperature sensors, blood pressure sensors, oxygenation sensors, skin resistance sensors, skin temperature sensors, movement sensors, vibration sensors, impact sensors, eye status sensors, body movement sensors, apparel detectors, ambient temperature sensors, ambient humidity sensors, ambient noise sensors, and global positioning sensors.

In some embodiments, the first sensor is an identity sensor, the electromagnetic radiation-emitting device stores treatment information comprising dates and times of NIR treatments administered to respective persons, and dosages of NIR administered to respective persons during NIR treatments, the electromagnetic radiation-emitting device stores regimen information comprising desired agendas for NIR treatments to be administered to respective persons, the electromagnetic radiation-emitting device determines an identity of a first person who is in a detection range for the first sensor, the electromagnetic radiation-emitting device determines whether the first person is in need of an NIR treatment, and if so, the NIR treatment that should be administered to the first person, based on the detected identity of the first person, treatment information for the first person stored in the electromagnetic radiation-emitting device and regimen information stored in the electromagnetic radiation-emitting device for the first person, and the electromagnetic radiation-emitting device administers a desired NIR treatment to the first person, if the electromagnetic radiation-emitting device determines that the first person is in need of an NIR treatment, said desired NIR treatment based on the detected identity of the first person, the treatment information for the first person stored in the electromagnetic radiation-emitting device and the regimen information stored in the electromagnetic radiation-emitting device for the first person.

In some embodiments, the first sensor is an identity sensor, the electromagnetic radiation-emitting device determines an identity of a first person who is in a detection range for the first sensor, based on information from the identity sensor, the electromagnetic radiation-emitting device stores regimen information comprising desired NIR treatments to be administered to respective persons, the electromagnetic radiation-emitting device determines whether an NIR treatment should be administered to the first person, based on a determined identity of the first person, and the electromagnetic radiation-emitting device administers a desired NIR treatment to the first person, based on the determined identity of the first person and stored regimen information for the first person, if the electromagnetic radiation-emitting device determines that an NIR treatment should be administered to the first person.

In some embodiments, the electromagnetic radiation-emitting device receives input person identification comprising an input identity of a first person, the electromagnetic radiation-emitting device stores treatment information comprising dates and times of NIR treatments administered to respective persons, and dosages of NIR administered to respective persons during NIR treatments, the electromagnetic radiation-emitting device stores regimen information comprising desired agendas for NIR treatments to be administered to respective persons, the electromagnetic radiation-emitting device determines whether the first person is in need of an NIR treatment, and if so, the NIR treatment that should be administered to the first person, based on the identity of the first person, treatment information for the first person stored in the electromagnetic radiation-emitting device and regimen information stored in the electromagnetic radiation-emitting device for the first person, and the electromagnetic radiation-emitting device administers a desired NIR treatment to the first person, if the electromagnetic radiation-emitting device determines that the first person is in need of an NIR treatment, said desired NIR treatment based on the input identity of the first person, the treatment information for the first person stored in the electromagnetic radiation-emitting device and the regimen information stored in the electromagnetic radiation-emitting device for the first person.

In some embodiments, the electromagnetic radiation-emitting device receives input person identification comprising an input identity of a first person, the electromagnetic radiation-emitting device stores regimen information comprising desired NIR treatments to be administered to respective persons, and the electromagnetic radiation-emitting device administers a desired NIR treatment to the first person, based on the input identity of the first person and stored regimen information for the first person.

In some embodiments, the first sensor detects a first person in a detection range for the first sensor and the electromagnetic radiation-emitting device administers an NIR treatment to the first person upon the first sensor detecting that the first person is in the detection range for the first sensor. In some of such embodiments, the first sensor is selected from the group of sensors consisting of human sensors, head sensors, head orientation sensors, face sensors, movement sensors, eye status sensors, body movement sensors and weight sensors.

In some embodiments, the electromagnetic radiation-emitting device stores treatment information comprising dates and times of NIR treatments that have been administered, and dosages of NIR administered to respective persons during NIR treatments, the electromagnetic radiation-emitting device stores regimen information, the first sensor detects a first person in a detection range for the first sensor, the electromagnetic radiation-emitting device determines whether the first person is in need of an NIR treatment, and if so, the NIR treatment that should be administered to the first person, based on the treatment information stored in the electromagnetic radiation-emitting device and the regimen information, and the electromagnetic radiation-emitting device administers a desired NIR treatment to the first person, if the electromagnetic radiation-emitting device determines that the first person is in need of an NIR treatment, said desired NIR treatment based on the treatment information stored in the electromagnetic radiation-emitting device and the regimen information. In some of such embodiments, the first sensor is selected from the group of sensors consisting of human sensors, head sensors, head orientation sensors, face sensors, movement sensors, eye status sensors, body movement sensors and weight sensors.

In another embodiment, the method involves delivering electromagnetic radiation to a person from a device configured to emit (1) visible light comprising at least one wavelength in the range of from 490 nm to 500 nm and (2) near UV light. In some embodiments, the method further comprises sensing at least a first characteristic on a first sensor.

In another embodiment, the methods comprise emitting red visible light to a person from a device that comprises at least a first mounting structure, at least a first electromagnetic radiation emitter, and at least a first sensor; wherein every electromagnetic radiation emitter in the device that emits red visible light is mounted on at least one of the at least a first mounting structure, and wherein respective ray axes of emission of every electromagnetic radiation emitter that emits red visible light not passing through any of the at least a first mounting structure.

FIG. 12 depicts an embodiment of a device 120 within the scope of the fifth aspect discussed above, and that can be used in the method according to the twentieth aspect described herein. The device 120 comprises a plurality of electromagnetic radiation emitters and a mounting structure 121. The plurality of electromagnetic radiation comprises a plurality of emitters 122 that emit red visible light and a plurality of light emitters 124 that emit warm white light (i.e., with the majority of the emitted light being between about 500 nm and about 700 nm). The red emitters 122 are on a first surface 123 of the mounting structure 121, and the warm white emitters 124 are on a second surface 125 of the mounting structure 121. Light emitted from each of the respective red emitters 122 has a respective ray axis of emission 126, and each respective ray axis of emission 126 does not pass through any portion of the mounting structure 121.

In some embodiments, the method further comprises sensing at least a first characteristic on a first sensor. In some aspects of such embodiments, the first sensor is at least 50 mm from the person being irradiated with the red visible light.

In another embodiment, the methods comprise actuating at least a first actuator of an electromagnetic radiation-emitting device that comprises at least the first actuator and at least a first electromagnetic radiation emitter that is configured to emit electromagnetic radiation comprising red visible light, said actuating the first actuator causing the first electromagnetic radiation emitter to emit electromagnetic radiation comprising red visible light of wavelength in the range of 600 nm-640 nm. In some embodiments, the first actuator is a pushbutton, and in others, is a timer. In some embodiments, the NIR emitter is partially in a bed, chair, pillow or mattress, and in others, is completely in a bed, chair, pillow or mattress.

In another embodiment, the method comprises attaching at least a first electromagnetic radiation-emitting device to a bed, a chair, a pillow or a mattress, the electromagnetic radiation-emitting device comprising at least a first electromagnetic radiation emitter and at least a first attachment feature, and the first electromagnetic radiation emitter configured to emit electromagnetic radiation comprising NIR.

The method can further comprise the step of irradiating a patient/user sleeping in the bed, or sitting in the chair, for example, with the irradiation being applied to a position proximate the patients head, or a portion thereof.

In some embodiments, the first electromagnetic radiation-emitting device is attached to the bed, chair, pillow or mattress by at least a first attachment feature selected from the group of attachment features consisting of suction cups, adhesives, magnets, screw holes and bolt holes.

In another aspect, the method comprises emitting light selected from among NIR, IR light and UV light from an electromagnetic radiation-emitting device that comprises a plurality of electromagnetic radiation emitters, said plurality of electromagnetic radiation emitters comprising at least a first NIR emitter, the first NIR emitter configured to emit electromagnetic radiation comprising NIR, at least a first IR light emitter, the first IR light emitter configured to emit electromagnetic radiation comprising IR light; and at least a first UV light emitter, the first UV light emitter configured to emit electromagnetic radiation comprising UV light.

The methods can be used, for example, to provide specific electromagnetic radiation treatments (involving different types of radiation, e.g., which can include NIR and IR, NIR and UV, IR and UV, or NIR, IR and UV, and optionally also visible light, simultaneously, sequentially or a combination of simultaneous and sequential) that provide useful effects on persons.

In some embodiments, the method comprises simultaneously emitting from the electromagnetic radiation-emitting device NIR, IR light and UV light, and in other embodiments, at least one of the NIR, the IR light and the UV light is not emitted during a portion of time that at least one other of the NIR, the IR light and the UV light is emitted. In some embodiments the electromagnetic radiation-emitting device further comprises at least a first visible light emitter.

In accordance with a twenty-fifth aspect of the present inventive subject matter, there is provided a method, comprising positioning a first electromagnetic radiation emitter (1) on, (2) partially in, or (3) entirely in the first furnishing, the first furnishing selected from the group of furnishings consisting of pillows, mattresses, beds and chairs, the first electromagnetic radiation emitter configured to emit electromagnetic radiation comprising NIR.

In another aspect, the methods comprise emitting light selected from among NIR and visible light of at least a first color temperature, from an electromagnetic radiation-emitting device that comprises a plurality of electromagnetic radiation emitters, and a color temperature selection element, said plurality of electromagnetic radiation emitters comprising: at least a first electromagnetic radiation emitter that is configured to emit electromagnetic radiation that comprises NIR; and at least a first variable-color-temperature emission element that comprises one or more variable-color-temperature emission element emitters, actuating said color temperature selection element to select a first color temperature from among at least two selectable color temperatures, thereby causing the electromagnetic radiation-emitting device to emit visible light of said first color temperature.

The methods can provide specific electromagnetic radiation treatments (including NIR, visible light of one or more color temperature, or a combination of NIR and visible light of one or more color temperature, simultaneously, sequentially or a combination of simultaneous and sequential) that provide useful effects on persons.

In some embodiments, the NIR and the visible light of the first color temperature are emitted simultaneously, and in other embodiments, the visible light of the first color temperature and the visible light of the second color temperature are not emitted simultaneously.

In another aspect, the methods comprise emitting NIR from at least a first NIR emitter; and emitting visible light from at least a first visible light emitter, the first NIR emitter and the first visible light emitter on a first mounting structure, the NIR having a first ray axis of emission relative to the first mounting structure, the first ray axis of emission extending in a first direction, the visible light having a second ray axis of emission relative to the first mounting structure, the second ray axis of emission extending in a second direction, the first direction defining an angle of at least 50 degrees relative to the second direction.

In another aspect, the methods comprise delivering NIR to a head of a person; and prompting the person to engage in cognitive activity while the head of the person is receiving said NIR.

These methods can be carried out using any of the devices described herein. The methods can provide specific NIR treatments that provide useful effects on persons, in particular, to provide a combination of effects that provide useful effects on persons suffering from AD or that provide useful effects on preventing AD or slowing progression of AD or other cognitive disorders.

In some embodiments, the cognitive activity is selected from the group of cognitive activities consisting of (1) answering questions, (2) solving puzzles and (3) performing movements in response to visual and/or audible prompts.

In another aspect, the methods comprise emitting NIR from a first electromagnetic radiation emitter in an electromagnetic radiation-emitting device, the electromagnetic radiation-emitting device, comprising at least a first mounting structure and the first electromagnetic radiation emitter, wherein the first mounting structure is devoid of any region in which a first point is spaced from a second point by not more than 0.1 cm, and a first line that is perpendicular to a first plane that is tangential to the first point defines an angle of more than 60 degrees relative to a second line that is perpendicular to a second plane that is tangential to the second point.

In another aspect, the methods comprise emitting NIR from at least 20 electromagnetic radiation emitters that each have a respective tangential plane that is perpendicular to a respective ray axis of emission of the electromagnetic radiation emitter, each of the respective tangential planes defining an angle of not greater than 20 degrees relative to a first plane.

As indicated above, various embodiments in accordance with the present inventive subject matter involve a variety of electromagnetic radiation emitters. In general, any suitable emitter can be used to provide the respective types of electromagnetic radiation, and persons of skill in the art are familiar with a wide variety of electromagnetic radiation emitters. For example, electromagnetic radiation emitters that emit light of IR and NIR wavelengths (e.g., 700 nm-1400 nm) can be found at https://en.wikipedia.org/wiki/Infrared; electromagnetic radiation emitters that emit red light or other visible light (e.g., 380 nm-780 nm) can be found at https://en.wikipedia.org/wiki/Visible_spectrum; other wavelength lights can also be used, such as mixtures of light wavelengths or light wavelengths used individually, e.g. NIR for AD, NIR/Red for sleep aid, red or amber for night light, white light for reading, bright blue/white light for wakeup and/or alertness, blue or UVA for bacterial/fungal control.

Representative examples of types of electromagnetic radiation emitters include light emitting diodes (LEDs), laser diodes, incandescent lights, fluorescent lamps, luminescent materials (up-converting or down-converting, pumped with any suitable light source), thin film electroluminescent devices, light emitting polymers (LEPs), halogen lamps, high intensity discharge lamps, electron-stimulated luminescence lamps, etc., with or without filters. An electromagnetic radiation emitter can in general be used by itself, with other similar electromagnetic radiations, and/or with different types of electromagnetic radiations (i.e., in some cases, there are a combination of one or more light sources of each of a plurality of types).

Representative examples of specific characteristics that can be employed in the methods and devices described herein include: electromagnetic radiation emitters being modulated NIR or red LED based products that illuminate/radiate and penetrate the human body; combining light treatments with feedback sensing; use of lightweight materials; thermally cool construction; powering by low voltage; using red LEDs (630 nm, 660 nm), NIR LEDs (810 nm, 830 nm, 870 nm); using light modulation (pulses at 10 Hz, and/or pulse shaping); using sensor feedback (ultrasonic doppler, skin resistance, pulse, pulse velocity, camera, skin temperature); using links to wearable tech, e.g., fitbit, apple watch, etc. for sensor feedback or other purposes; combining light treatments with magnetic treatment, sound treatment, ultrasound treatment, heat therapy, massage therapy; use of devices and methods disclosed herein for cosmetic treatments and/or interventions (e.g., red light for hair, yellow light for skin, blue light for fungus).

In some aspects, the devices detect the presence of a living thing and activate treatment or therapy. In some aspects, the devices recognize that a "head" is present, and activate treatment or therapy on that basis (and in some instances, recognize the positioning and/or orientation of the head and tailor the treatment or therapy based on the positioning and/or orientation of the head). In some aspects, the devices measure biological data (e.g., surface temperature, oxygenation, pulse velocity, pulse before, during and/or after treatment or therapy), and in some instances tailor the treatment or therapy (or the next treatment or therapy) based on such data. In some aspects, the devices detect whose head is in the treatment region (i.e., the person's identity), and in some instances personalize data storage and/or treatment/therapy.

In very specific aspects, persons are treated with NIR having the parameters selected based on criteria as described in this paragraph: wavelength (e.g., 810 nm) based on (1) effectiveness for light penetration of living tissue due to minimization of absorption by three major tissue components, i.e., chromophores, hemoglobin and melanin, along with water, and on (2) effectiveness of absorption by mitochondria that are believed to be responsible for the biological effects of photobiomodulation; energy density (e.g., 60 $J/cm^2$) with reference to data indicating that transcranial laser for stroke in humans and knowledge about the optical properties of human tissue; power density (e.g., 250 $mW/cm^2$) to be safe and to avoid heating of the skin.

In some aspects of these embodiments, because the source of light is relatively far from the user, in contrast to devices which are in direct contact with a user, or are positioned very close to a user, it may be advantageous to use a more high-powered light source. U.S. Publication No. 20150112411 discloses devices with high-powered LEDs that can be used in connection with the treatments described herein. The devices are portable high-powered light emitting diode photobiology devices that include a plurality of light emitting diodes, including a first one having a first predetermined wavelength with a first emission axis, as well as a second one having a second predetermined wavelength with a second emission axis. The device can further include a plurality of optics including a first optic corresponding to the first one of the plurality of light emitting diodes that defines a first dispersion pattern of enhanced light intensity centered on the first emission axis, and a second optic corresponding to the second one of the plurality of light emitting diodes that defines a second dispersion pattern of enhanced light intensity centered on the second emission axis.

The device may further include an optical face defined by a flat planar surface. The first one of the plurality of light emitting diodes can be positioned in a first tilted angular relationship relative to the flat planar surface of the optical face. The second one of the plurality of light emitting The devices can also include a "user control area" providing indicators and switches by which a user can select and confirm desired treatment parameters. The device may also include a housing substantially enclosing and retaining the light emitting diodes, optics and user control area. The device can also optionally include an optical face substantially integrated with the housing to provide a smooth surface toward the area of treatment, and/or an optical face including a diffuser for uniform dispersion of light.

In contrast to LED phototherapy devices that come into contact with a user, these devices can be used at a distance from the user. While conventional phototherapy devices may lose more than 50% of their emitted power at a distance of as little as ½", these high-power LEDs, with reflector optics having dispersion angles of approximately 45-90 degrees, can deliver desired light output with uniform intensity diffused across a large area in contact or non-contact methods of treatment.

These devices can eliminate the need for direct contact by employing reflector optics and high-power LEDs having predetermined frequency outputs. Non-contact treatment further addresses treating sensitive, painful, or difficult to reach areas of the body. In turn, by incorporating the emitting surface of the optics into the surface of the housing, some embodiments of the device can be configured to be quickly and easily cleaned and sterilized between uses.

The device can include a sealed light-emitting surface that enables cleaning and sterilization prior to use. The device can also include optics associated with LEDs for controlling diffusion and intensity of emitted light over a larger area to improve treatment efficacy. The device can also provide combinations of predetermined light frequencies for use over a range of treatment durations.

In another embodiment, an enclosure analogous to a tanning bed, but with light sources that emit light at the wavelengths, power levels, and the like as described herein, are used. Such tanning beds are commercially available, and the light sources can be modified to provide light at the wavelengths described herein. The tanning beds typically include timers and/or actuators that control the time period that the light is applied.

Specific devices described above are discussed in more detail below. Various embodiments of the devices described herein are shown in FIGS. 1-10. Each of these devices can be configured to emit NIR light, or, alternatively, can be configured to emit a combination of wavelengths, which combination of wavelengths may or may not include NIR light. For example, light can be administered at a first anti-inflammatory wavelength, a second wavelength that promotes the production and/or release of endogenous nitric oxide, a wavelength that promotes the production and/or release of endogenous neurotransmitters, and/or which repairs the blood-brain barrier. In some embodiments of each of these devices, the light is emitted at a combination of wavelengths, which combination includes at least a first anti-inflammatory wavelength, and a second wavelength that promotes the production and/or release of endogenous nitric oxide. These wavelengths can be emitted simultaneously or sequentially, according to pre-determined emission schedules, or can be emitted with overlapping emission schedules. These wavelengths can also be emitted, directly and/or indirectly, to all, or one or more portions, of the brain. Depending on the indication to be treated or prevented, it may be desirable to expose one portion of the brain to one wavelength, or range of wavelengths, and another portion of the brain to another wavelength, or range of wavelengths.

Figure 1:
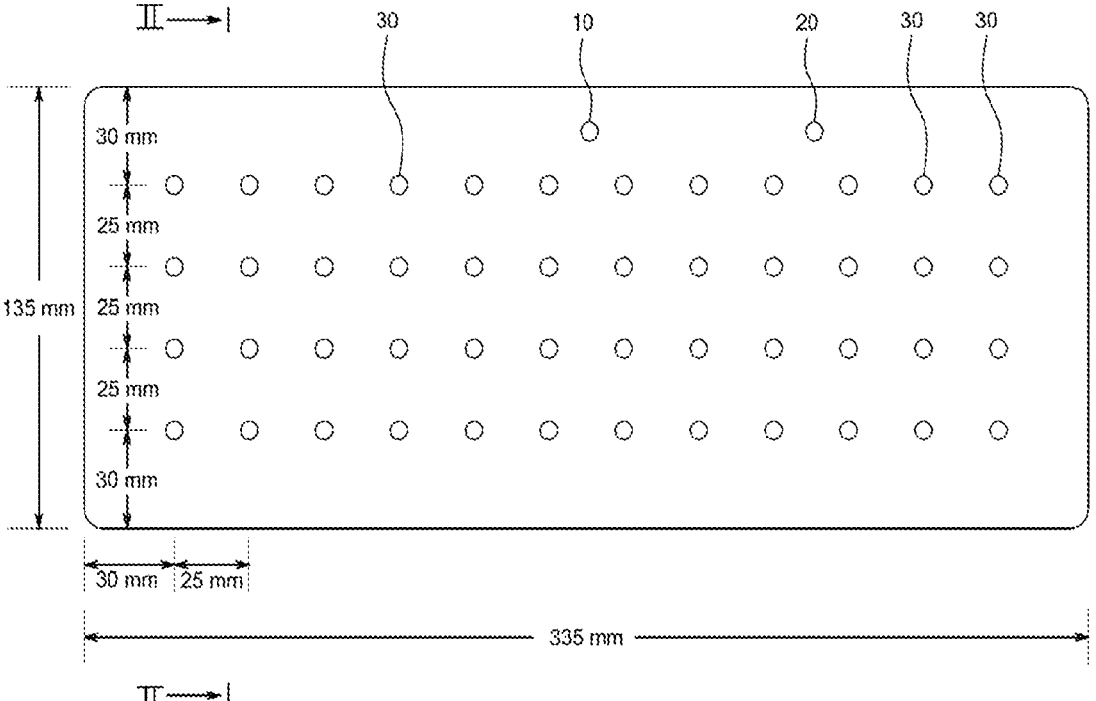
FIG. 1 schematically depicts a first embodiment of an electromagnetic radiation-emitting device in accordance with the present inventive subject matter.

FIG. 1 schematically depicts a front face of an embodiment of an electromagnetic radiation-emitting device as described herein. The device comprises a plurality of emitters 30 arranged in an array, a human sensor 10 and a light sensor 20. The array of emitters 30 defines a pattern that has a 30 mm border around its perimeter, four rows, and 12 columns. Each row is spaced from its neighbor (or neighbors) by 25 mm. Each column is spaced from its neighbor (or neighbors) by 25 mm. Each of the emitters 30 can be configured to emit light of any wavelength (or within a range of wavelengths), e.g., in some embodiments, each of the emitters 30 is configured to emit NIR light. The human sensor 10 is configured to detect whether any human is within a detection range of the device. The light sensor can be any desired light sensor, e.g., a sensor that detects whether light of a particular wavelength (or light in a particular wavelength range) is incident on the device, a sensor that detects radiosity of light incident on the device, radiosity of light of a specific wavelength or wavelength range that is incident on the device, etc.

Figure 2:
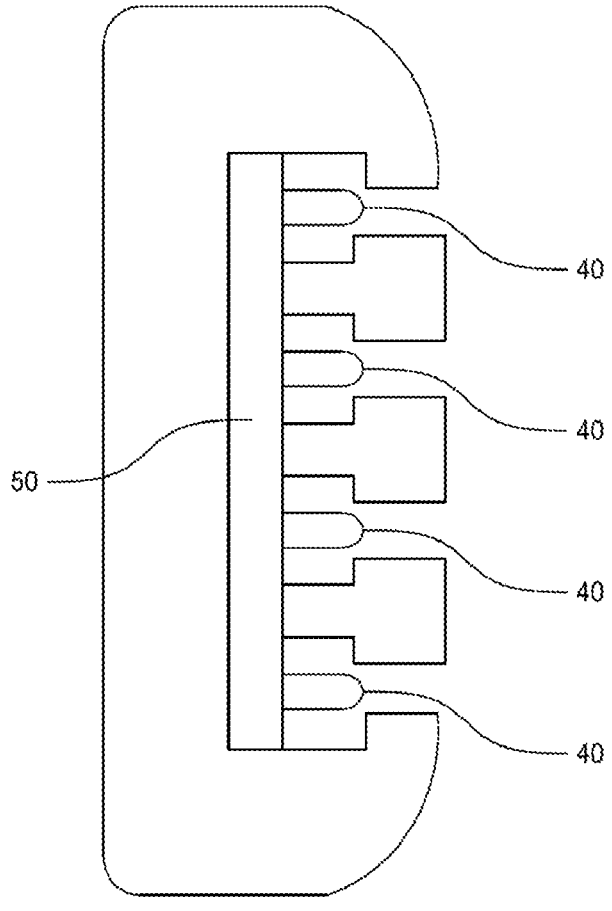
FIG. 2 is a sectional view taken along II-II in FIG. 1.

FIG. 2 is a sectional view of an electromagnetic radiation-emitting device similar to the device depicted in FIG. 1, the section taken along a line that is analogous to II-II in FIG. 1. FIG. 2 shows a plurality of emitters 40 attached to a printed circuit board 50. Each of the emitters 40 can be configured to emit light of any wavelength (or within a range of wavelengths, or in a combination of wavelengths). In some embodiments, each of the emitters 40 is configured to emit NIR light, and in other embodiments, the emitters are configured to emit a combination of wavelengths, where light is administered at a first anti-inflammatory wavelength, and a second wavelength that promotes the production and/or release of endogenous nitric oxide. As shown in FIG. 2, each of the emitters 40 is recessed somewhat from the face of the device (i.e., the surface along the right edge of the device, in the orientation depicted in FIG. 2).

Figure 3:
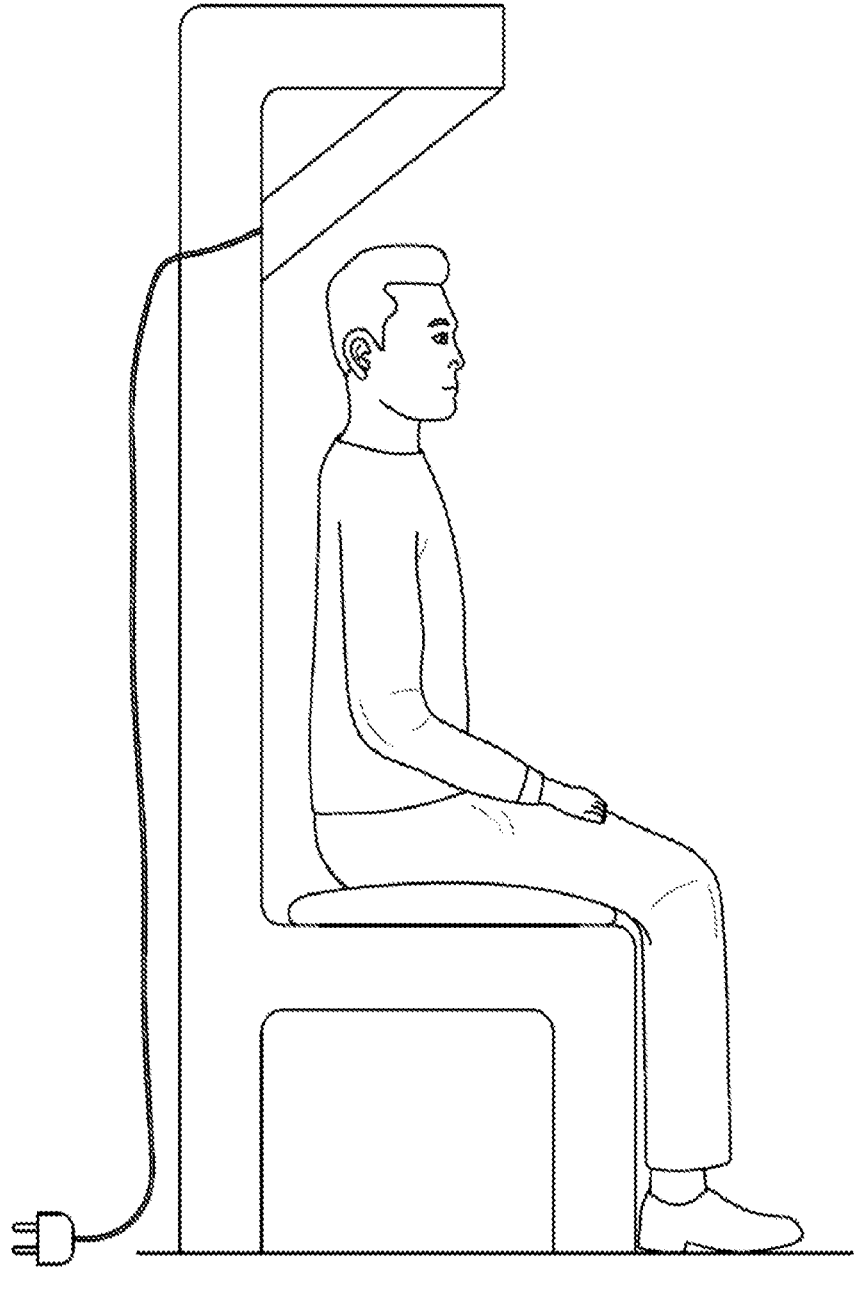
FIG. 3 schematically depicts an embodiment of an electromagnetic radiation-emitting device in accordance with the present inventive subject matter, attached to a chair, with a patient in the chair.

FIG. 3 schematically depicts an embodiment of an electromagnetic radiation-emitting device as described herein, attached to a chair, with a patient in the chair. The device is configured to deliver light of desired wavelength (or range and/or combination of wavelengths) to each of one or more region of the patient's body. For example, in some embodiments, the device is configured to deliver NIR light to the patient's head, and in other embodiments, a is configured to deliver a combination of wavelengths, where light is administered at a first anti-inflammatory wavelength, and a second wavelength that promotes the production and/or release of endogenous nitric oxide.

Figure 4:
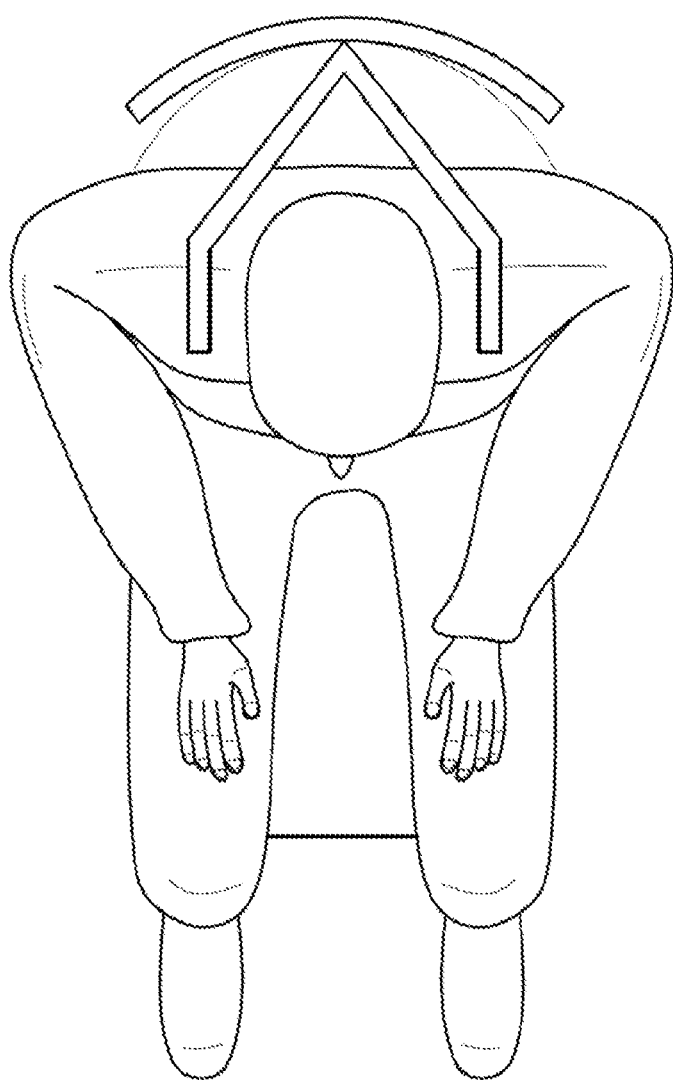
FIG. 4 schematically depicts an embodiment of an electromagnetic radiation-emitting device in accordance with the present inventive subject matter, and a person's head positioned close thereto.

FIG. 4 schematically depicts an embodiment of an electromagnetic radiation-emitting device as described herein, and a person's head positioned close thereto. The device is configured to deliver light of desired wavelength (or range and/or combination of wavelengths) to each of one or more region of the patient's head. For example, in some embodiments, the device is configured to deliver NIR light to the patient's head, and in other embodiments is configured to emit a combination of wavelengths, where light is administered at a first anti-inflammatory wavelength, and a second wavelength that promotes the production and/or release of endogenous nitric oxide.

Figure 5:
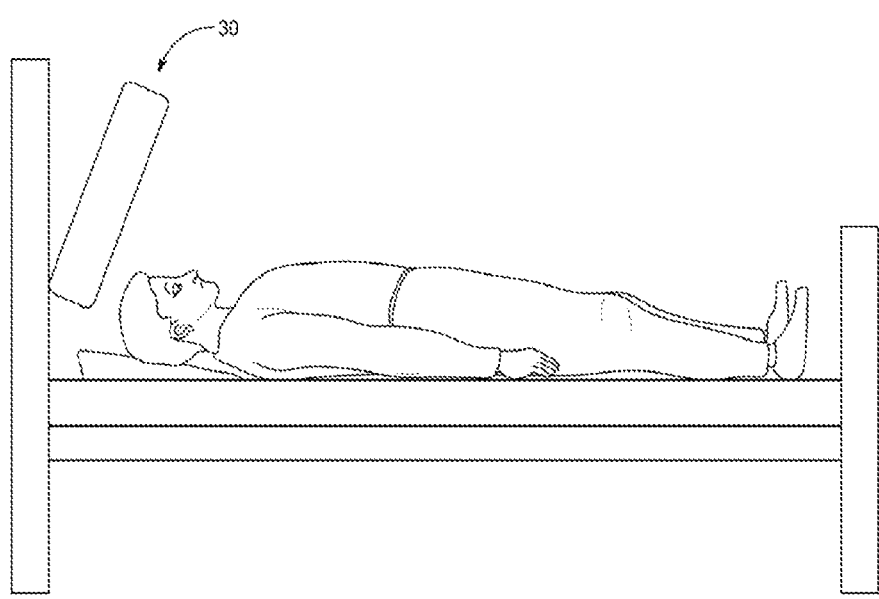
FIG. 5 schematically depicts an embodiment of an electromagnetic radiation-emitting device in accordance with the present inventive subject matter, attached to a bed, with a patient in the bed.

FIG. 5 schematically depicts an embodiment of an electromagnetic radiation-emitting device 30 as described herein, attached to a bed, with a patient in the bed. The device is configured to deliver light of desired wavelength (or range of wavelengths) to each of one or more region of the patient's head. For example, in some embodiments, the device is configured to deliver NIR light to the patient's head, and in other embodiments, the emitters are configured to emit a combination of wavelengths, where light is administered at a first anti-inflammatory wavelength, and a second wavelength that promotes the production and/or release of endogenous nitric oxide.

FIG. 6 schematically depicts (as a block diagram) circuitry for an embodiment of an electromagnetic radiation-emitting device as described herein. The circuitry comprises a CPU and memory 100. The CPU sends and receives signals (e.g., WiFi or Bluetooth®) via serial communication through a device 80 with at least a transmitting pin and a receiving pin. The CPU receives signals from a GPS 90. The CPU receives signals from a microphone 60. The CPU sends signals to a speaker 70. The CPU is configured to drive NIR LEDs as well as other LEDs (e.g., visible light). The CPU receives signals from a temperature sensor. The CPU is also connected to a PTR diode. A power supply 110 provides power to the LEDs and the circuitry from a battery and/or a wall plug.

FIG. 7 schematically depicts (as a block diagram) additional circuitry for an embodiment of an electromagnetic radiation-emitting device as described herein. The circuitry comprises a controller CPU 140. The CPU 140 sends and receives signals to and from a memory 130. The CPU 140 also sends and receives signals to and from a timer 120. The CPU 140 receives signals from a GPS 90. The CPU also sends and receives signals via WiFi and/or Bluetooth®. The circuitry also comprises control buttons. The circuitry further comprises a power connector and a battery to supply current to the CPU 140 and to NIR LEDs, red LEDs and white LEDs based on signals supplied from the CPU 140.

FIG. 8 schematically depicts a front face of another embodiment of an electromagnetic radiation-emitting device as described herein. The device comprises a plurality of emitters 30 arranged in an array, a plurality of ambient light LEDs (along the top side of the device), a microphone 60, a camera 170 and a proximity detector 180. The front face can be directed toward the head of a patient. Each of the emitters 30 can be configured to emit light of any wavelength (or within a range of wavelengths, or combination of wavelengths). In some embodiments, each of the emitters 30 is configured to emit NIR light, and in other embodiments, the emitters are configured to emit a combination of wavelengths, where light is administered at a first anti-inflammatory wavelength, and a second wavelength that promotes the production and/or release of endogenous nitric oxide. In some embodiments, the proximity detector 180 controls when the device operates and for how long, by detecting if a person is present and/or detecting movement).

FIG. 9 is a perspective schematic view of another embodiment of an electromagnetic radiation-emitting device as described herein. The device comprises a plurality of emitters 30 arranged in an array, a plurality of ceiling/wall wash emitters 200 (along the top side of the device), an ambient light detector 210, a microphone 60, speakers 70, and a sensor 190. The device is secured in place by a bracket 220. Each of the emitters 30 can be configured to emit light of any wavelength (or within a range of wavelengths, or a combination of wavelengths). In some embodiments, each of the emitters 30 is configured to emit NIR light, and in other embodiments, the emitters are configured to emit a combination of wavelengths, where light is administered at a first anti-inflammatory wavelength, and a second wavelength that promotes the production and/or release of endogenous nitric oxide.

FIG. 10 schematically depicts an embodiment of an electromagnetic radiation-emitting device as described herein, with a person's head near the electromagnetic radiation-emitting device. Referring to FIG. 10, the device comprises a plurality of emitters 30, a sensor 190, and a ceiling light emitter (on the top surface of the device). The device is secured in place by being attached to a bracket 220, and the height of the device can be adjusted (relative to a patient's head 240).

II. Devices Which Come Into Direct Contact With a User

In addition to devices that do not come into contact with the user, devices can also be used which do come into contact with the user. The light can be administered in any way that allows the light to pass through the skin and into the brain.

Each of the devices includes, or can include, common components. These include one or more light sources, a power supply, which can include a rechargeable battery, a controller for controlling the light source, a switch and/or actuator for turning the device on or off, and optionally a sensor, as described elsewhere herein. Since these devices come into contact with a user, proximity sensors can be used to determine how close the light is to the patient's skin. Temperature sensors can determine how much the light has heated the skin. The devices can also include a means, such as a fan or heat sink, for removing heat from the user's skin. The devices can also include a diffuser to diffuse the light, so that it is more evenly distributed, or a photomask, to preclude light from impinging on certain portions of the user's skin.

The devices can also include an alarm for alerting an individual to a time to commence or cease treatment, safety or cut-off means for cutting the power supply, and/or timing means to measure the length of a treatment period.

In various embodiments, the devices can deliver light via intra-cranial administration, delivery through the scalp, such as by using a therapeutic helmet, delivery to the eyes, such as by using eyeglasses that shine light through the eyelids, or by shining light on a screen, intranasal delivery, such as by light sources inserted in the nostrils, delivery to the ears, delivery to sites remote from the brain, such as through skin overlying a bone, delivery to the blood, delivery to the skin, delivery to a body cavity, such as the throat, a "wearable" device for irradiating the skin, a probe designed to penetrate the skin and deliver light underneath the skin, a biocompatible implant that is implanted underneath the scalp, a trans-cutaneous irradiation module, and combinations thereof. These various devices are discussed in more detail below.

A number of these types of devices are known in the art, though not for administering light in a combination of wavelengths as described herein, or for treating various disorders described herein.

In one embodiment, light is delivered directly to the user's cranium. U.S. Publication No. 20160235983 discloses an apparatus for delivering light to the cranium. The apparatus includes a light source positionable proximate to a surface of the user's cranium, and can optionally include multiple energy portals in communication with any of a variety of suitable sources of light energy. The multiple energy portals are capable of emitting light energy directed towards the subject's cranium.

The device also includes a controller to control light emissions for a predetermined period of time with a predetermined energy level. The controller includes a processor and a digital data storage, as well as a biometric measurement device capable of quantifying one or more biological aspects of the user. The biometric measurement device can constantly or intermittently provide digital data to the controller indicative of the one or more measurements quantifying biological aspects of the user before, during, and/or after administration of the predetermined light therapy.

The device can include a neurofeedback system in logical communication with the controller, including external stimulation administered to the mammalian subject in the form of at least one of visual stimulation, audio stimulation, trans-cranial electrical stimulation, trans-cranial magnetic stimulation, trans-tongue electronical stimulation, and trans-dermal electrical stimulation. A biofeedback system can be in logical communication with the light source to continue or modify at least one of the predetermined light therapy and neurofeedback administered to the user based on one or more measurements quantifying biological aspects of user.

The device can also include a data storage device for storing the one or more biological measurements before, during, and/or after the light therapy and/or neurofeedback therapy. The device can also include a source of electrical logic signals in logical communication with the controller. These signals can cause the controller to receive input from the biometric measurement device and cause the light source to continue delivering the predetermined light energy therapy, or selectively modify the predetermined light therapy to the user based on the input from the biometric measurement device. Modification of the predetermined light therapy can include modifying a selection of the light portals, and wavelengths, energy level, duration, and/or frequency of the emitted light.

In one embodiment, the light is administered using an intracranial, light-emitting implant, such as the implant disclosed U.S. Pat. No. 8,821,559, though equipped with light sources that emit one or more wavelengths not disclosed in the '559 patent and/or used to treat CNS disorders other than those taught in the '559 patent.

The implant includes a light source, an antenna in electrical connection with the light source, and, optionally but preferably, a controller. In use, a surgeon implants the device into the brain of the patient. To protect the active elements of the device from the cerebrospinal fluid (CSF) and/or minimize the foreign body response, in some embodiments, the light source is encased in a casing. This casing is ideally made of a material transparent to the wavelengths being emitted. Representative casing materials include ceramics and polymers. Suitable ceramics include alumina, silica, CaF, titanic and single crystal-sapphire, and suitable polymers include polypropylene and polyesters.

In some embodiments, the light emitting portion of the implant is located separate from the LED. This can be accomplished using a light communication means, such as a fiber optic cable, a wave guide, a hollow tube, a liquid filled tube, or a light pipe.

Light can also be administered using a probe. In some embodiments, the probe is inserted into the brain. In one embodiment, the probe includes a probe body configured to penetrate biological tissue, and a plurality of light sources, which can be high-efficiency LEDs, disposed within the probe body. The light intensity is sufficient to trigger a light-sensitive reaction in neighboring tissues, but not sufficient to provide a combined heat that would cause a disruptive temperature increase in the neighboring tissues. Exemplary probes are disclosed, for example, in U.S. Pat. No. 10,874,876.

In other embodiments, the probe is used to introduce light into the throat, so that it penetrates into specific areas of the brain and spinal column that are more accessible in this manner than by applying light to the scalp. For example, PCT WO 2019165302 discloses systems and methods for administering phototherapy to the throat, and, ultimately, to the pharynx, using a transpharyngeal probe.

The devices include a hollow structure having at least a first open end. The hollow structure includes a rotatable member, one or more coherent light generators, and, for each coherent light generator, one or more lenses or mirrors optically connected to the coherent light generator and configured to alter at least one aspect of a beam of coherent light. The device further includes a processing circuit including a processor and a memory storing instructions. The instructions, when executed by the processor, cause the processor to accept an input from an operator and generate one or more beams of coherent light according to a plurality of settings configured to produce a therapeutic effect at a targeted treatment site. Additionally, the rotatable member is configured to be rotated to direct the one or more beams of coherent light to the targeted treatment site.

In some embodiments, the light is administered such that it is directed posteriorly and upward, or directly to the back of the pharynx or pharyngeal pharynx, and onto the upper brainstem, the mid brainstem, and the lower brainstem and the upper spinal column. Delivering phototherapy via a transpharyngeal probe to the brainstem's sleep center or into a brainstem that has suffered a contusion or concussion injury can be a better approach for delivering light to these tissues than delivering phototherapy trans-cranially or topically through the forehead's skin and frontal bone's skull bone areas.

Light can also be administered using catheters. For example, U.S. Publication No. 20100121420 discloses providing phototherapy to the brain region using catheters. The catheters can include any combination of LEDs, OLEDs, lasers or other light emitting devices on tips, either individually or in arrays, or any other form of light via fiber optic conduits. The light can be introduced within the vasculature, by direct percutaneous or intraoperative penetration, or by accessing hollow cavities, such as the nasal passages, mouth, and ears, or fluid filled areas or cavities. One can use various sized catheters and/or fiberoptic conduits to deliver light in one or multiple branches of blood supply to areas of the brain by following the larger blood vessels (arteries or veins or any other type of blood vessel) to access smaller vessels. This allows for a combination of various sized catheters and/or fiber optic conduits to be used to create and envelopment of light around a given brain region and/or the watershed area of the blood vessels being used to access the area. Arteries and/or veins can be used for access. Alternatively, one can access the ventricular system of the brain by entering through the skull into the central sulcus or through the skull to apply the phototherapy described herein to areas of the subdural or epidural locations and the blood supplies within those regions.

In some embodiments, light is administered using an implant that is positioned between the skull and the scalp. PCT WO 2012024243 discloses minimally invasive devices that can be adapted for use to treat neurological disorders with low level light therapy, using the wavelengths described herein. The devices include a substantially flat, biocompatible base sheet configured to be implanted between the subject's scalp and the subject's skull, and configured to be anchored to an outer surface of the subject's skull and one or more light sources mechanically coupled to the base sheet.

In other embodiments, light is delivered directly to the scalp, for example, using a light-emitting helmet. Numerous laser and LED helmets are commercially available for use in treating hair loss, and they can be modified to treat central nervous system disorders by providing light at the wavelengths, or combinations of wavelengths, described herein. A representative light-emitting helmet is disclosed in U.S. Pat. No. 10,688,315. A common feature of these helmets is that they include a plurality of light sources, whether lasers or LED light sources, on or near the surface of the helmet in contact with the user's scalp. Controllers can control how long the light is applied, what intensity of light is applied, and, if desired, to what desired locations of the scalp the light is administered.

Another suitable device for administering light to the scalp is disclosed in U.S. Pat. No. 10,188,872. The device can irradiate at least a portion of a patient's brain with light, and includes a light source, an output optical element including a rigid and substantially thermally conductive material, and a surface configured to be in thermal communication with the patient's body. A second surface can be configured to face away from the patient's scalp during treatment. The device can include a cooler thermally coupled to the second surface of the output optical element to remove heat from the output optical element through the second surface; and a heat sink thermally coupled to the cooler. The heat sink can be positioned so that the light propagates through the heat sink and through the output optical element.

U.S. Publication No. 20120046716 discloses a customized transcranial phototherapy device that follows the contours of a patient's head. The device includes a ring assembly and light emitting modules positioned between an upper and lower ring of the ring assembly. A first substantially circular ring and a second substantially circular ring that is of a smaller diameter than the first ring are used. Each ring is sized and shaped so as to be approximately commensurate with the circumference of an individual's head. In use, the rings fit over the individual's head, and each ring is provided with a plurality of engaging means, such as complementary interlocking male and female projections, and receiving units for receiving and securing a plurality of light emitting modules. The light, which can be LED, OLED, laser, or other light sources, can be pulsed, or provided in the form of a continuous wave.

The devices can further include one or more light emitting modules directed to the base of the skull, the eye area, or the occipital region, EEG electrodes and associated monitoring means, shoulder supports, and additional securing means for securing the apparatus about an individual's head. The device can include a transducer capable of measuring intracranial oxygenation.

Light can also be targeted to the basal ganglia. U.S. Publication No. 20150360049 discloses systems that include a light delivery element configured to direct radiation to at least a portion of a targeted tissue structure, a light source configured to provide light to the light delivery element, and a controller. The targeted tissue structure is a portion of the basal ganglia of the patient. The controller can be configured to be automatically operated to illuminate the targeted tissue structure with radiation at wavelengths, power levels, and the like as described herein. The device can also include a power supply connected to micro-controller unit (MCU), as well as LED drivers, fan drivers and/or a temperature sensor, each connected to power supply as necessary.

U.S. Publication No. 20150360049 also discloses modifying tissue to include a light sensitive protein, and exposing tissue expressing the light sensitive protein to radiation. The light sensitive protein can be an opsin protein, such as a depolarizing opsin, a hyperpolarizing opsin, a stimulatory opsin, an inhibitory opsin, a chimeric opsin, or a step-function opsin. Representative opsin proteins are selected from the group consisting of: NpHR, eNpHR 1.0, eNpHR 2.0, eNpHR 3.0, SwiChR, SwiChR 2.0, SwiChR 3.0, Mac, Mac 3.0, Arch, ArchT, Arch 3.0, ArchT 3.0, iChR, ChR2, C1V1-T, C1V1-TT, Chronos, Chrimson, ChrimsonR, CatCh, VChR1-SFO, ChR2-SFO, ChR2-SSFO, ChEF, ChIEF, Jaws, ChloC, Slow ChloC, iC1C2, iC1C2 2.0, and iC1C2 3.0.

Rather than specifically targeting the light to one location, it is possible to broadly expose the user to light. U.S. Publication No. 20160129279 discloses a wearable device for irradiating skin, and this device can be modified to emit light at the wavelengths described herein. The device can emit light at different frequencies, as desired. The device includes a light source, a light spreading sheet optically coupled to the light source, a controller electrically coupled to the light source, configured to control the intensity and duration of emitted light, a proximity sensor for detecting proximity of the light spreading sheet to skin, where the proximity sensor is electrically coupled to the controller, and a power source. The controller can be further configured to turn on the light source, and keep it turned on for the duration of a therapeutic session.

U.S. Publication No. 20180169434 discloses a device for applying light energy, externally, to a patient's head. The light is applied near the area of the brain that is malfunctioning or that is associated with the source of the disease to be treated. The treatment can be enhanced by activating the cranial nerves while the light is applied.

Light can be administered directly to the face, for example, by using a light mask. Light masks that emit LED or laser light to the face at wavelengths that treat wrinkles, acne, or other skin disorders are commercially available. These masks can be modified to emit light at one or more of the wavelengths described herein. As with the helmets, controllers can control how long the light is applied, what intensity of light is applied, and, if desired, to what desired locations of the scalp the light is administered.

Rather than delivering light to the skull or the face, light can be administered to bone marrow. This can cause stimulated mesenchymal stem cells to form, and travel to the brain, where they can have beneficial effects on a number of central nervous system disorders. The energy can be incoherent and/or coherent light, and can be administered transcutaneously, subcutaneously, or via an intramedullary probe. Suitable devices are disclosed in U.S. Pat. No. 9,403,030.

In some embodiments, light is administered through the ears. One device for delivering light through the ears is described in U.S. Pat. No. 10,471,276. The device was disclosed as using laser light, but can be modified to use other forms of light, such as LED light, and deliver the light to the outer ear. The device can allow for various variables, including the wavelength, power, area of illumination, area of stimulation, distance to skin surface, angle relative to skin surface, and frequency and duration of stimulation.

The device in the '276 patent comprises a housing adapted to be positioned over at least one target point, and at least one light source positioned on the housing whereby light from the light source is focusable onto the at least one target point. The device includes at least one sensor in sensory communication with the subject. The sensor is adapted to sense at least one physiological or neurological status of the subject and can be adapted to output at least one physiological or neurological status. The device also includes a driver operably connected to the at least one light source, capable of powering and controlling the at least one light source. Further, the device includes a command module operably connected to the driver and operably connected to the sensor. The command module can control at least one performance variable of the at least one light source, such as the wavelength, power, power density, voltage, current, pulse pattern, pulse frequency, beam spot diameter, angle of incidence, and combinations thereof. The controller can also receive at least one status output from the sensor, adjust at least one performance variable of at least one light source, and evaluate any change in the status output. If the status output is not optimized, it can adjust one or more performance variables.

In some embodiments, it is desirable to introduce light into a body cavity, such as the nose or mouth, in order to get light into the brain. U.S. Publication No. 20100121420 discloses providing ultraviolet light to at least one of: (a) below a skin of a mammal; or (b) to a body cavity, lumen, organ, tissue or tissue within the cavity of the mammal; or (c) within a blood or to the blood or to a specific type of cell of the mammal; to provide a phototherapeutic effect thereto. The devices can be altered to emit light at the wavelengths described herein, and used in the methods described herein.

Light can further be administered through the nose. Fiber optic cables or waveguides can be used to penetrate deep into the nasal cavity, or LEDs or other light sources can be passed into the nasal cavity. Light can be provided at one or multiple wavelengths.

Combinations of these approaches can be used, so that light is provided in more than one way to more than one site on a user. For example, PCT WO2019053625 discloses a photobiomodulation (PBM) system and method that directs therapeutic light energy into the brain from a combination of transcranial (through the skull) and intranasal (via the nasal channels) locations.

Transcranial administration directs light energy to dorsal/upper areas of the neocortical areas of the brain, and intranasal administration directs light energy to the ventral or underside of the brain, which can provide more comprehensive coverage than current transcranial methods alone and current intranasal methods alone.

The light energy can be directed to one or more specific areas of the brain, including the ventral medial prefrontal cortex (vmPFC), the dorsal medial prefrontal cortex (dmPFC), the posterior cingulate cortex (PCC), the precuneus (PCu), the lateral parietal cortex (LPC), the entorhinal cortex (EC), right dorsal-lateral prefrontal cortex (DLPC), left dorsal-lateral prefrontal cortex (DLPC), cerebellum and brain stem. Also, when administered to the nasal cavity, light energy is directed to the ventral prefrontal cortex, entorhinal cortex and/or parahippocampal area.

The light can also be administered to the external auditory canal, and also trans-cranially through one or more of the followings cranial bones: the temporal bone, squama temporalis of the temporal bone, mastoid portion of the temporal bone, petrous portion of the temporal bone, tympanic part of the temporal bone, the zygomatic bone, the sphenoid bone, the frontal bone, and the parietal bone.

In some embodiments, it is desirable to introduce light to the eye. It is possible to administer light through the eyelids, without damaging the eyes, and without interfering with the patient's ability to see, by using eyeglasses equipped with a light source that can be aimed at the upper eyelids.

IV. Wavelengths That Increase Vascularization, Provide Anti-Inflammatory Effects and/or Anti-Microbial Effects, and Promote NO Stimulation and/or Release The term "phototherapy" relates to the therapeutic use of light. The term "phototherapy" relates to the therapeutic use of light. As used herein, phototherapy is used to treat or prevent central nervous system disorders, lessen their severity, or slow their progression.

Phototherapy is used to treat or prevent microbial infections, including viral, bacterial and fungal infections, in brain tissue. The mechanisms by which light is antimicrobial can vary. In some embodiments, the light is administered at UVA (320-400 nm), UVB (280-320 nm), and/or UVC (200-280 nm) wavelengths. Of these, it is believed that UVC (wavelengths of 200-280 nm) is most germicidal.

UVC is absorbed by RNA and DNA bases in the microbes, and can cause the photochemical fusion of two adjacent pyrimidines into covalently linked dimers, which then become non-pairing bases (Perdiz et al., J. Biol. Chem., 275 (2000), pp. 26732-26742). UVB can also cause the induction of pyrimidine dimers, but less efficiently than UVC (id). UVA is weakly absorbed by DNA and RNA, and is much less effective than UVC and UVB in inducing pyrimidine dimers, but is believed to cause additional genetic damage through the production of reactive oxygen species, which cause oxidization of bases and strand breaks (Tyrrell et al., J. Photochem. Photobiol. B, 63 (2001), pp. 88-102).

Nitric oxide is also known to be antimicrobial and enhancing nitric oxide levels within the brain can be useful in inhibiting microbial infections in the brain. The precise mechanisms by which nitric oxide (NO) kills or inhibits the replication of a variety of intracellular pathogens is not completely understood. However, it appears that the cysteine proteases are targeted (Saura et al., Immunity, Volume 10, Issue 1, 1 Jan. 1999, Pages 21-28). NO S-nitrosylates the cysteine residue in the active site of certain viral proteases, inhibiting protease activity and interrupting the viral life cycle. Since cysteine proteases are critical for virulence or replication of many viruses, bacteria, and parasites, NO production and release can be used to treat microbial infections. Accordingly, in some embodiments, light is administered at wavelengths effective for enhancing endogenous NO production and/or release. These wavelengths are discussed in more detail below.

The photoinitiated release of endogenous stores of nitric oxide ("NO") effectively regenerates "gaseous" (or unbound) nitric oxide that was autooxidized into nitrosative intermediates and were bound covalently in the body in an "bound" state. By stimulating release of nitric oxide from endogenous stores, nitric oxide may be maintained in a gaseous state for an extended duration and/or a spatial zone of nitric oxide release may be expanded.

Nitric oxide is endogenously stored on a variety of nitrosated biochemical structures. Upon receiving the required excitation energy, both nitroso and nitrosyl compounds undergo hemolytic cleavage of S—N, N—N, or M-N bonds to yield free radical nitric oxide. Nitrosothiols and nitrosamines are photoactive and can be phototriggered to release nitric oxide by wavelength specific excitation.

The effect of light at certain wavelengths in the production and/or release of nitric oxide is described in U.S. Pat. No. 10,525,275, the contents of which are hereby incorporated by reference.

It has been reported that NO may diffuse in mammalian tissue by a distance of up to about 500 microns. In certain embodiments, photons of a first energy $h\upsilon 1$ may be supplied to the tissue to stimulate enzymatic generation of NO to increase endogenous stores of NO in a first diffusion zone 1. Photons of a second energy $h\upsilon 2$ may be supplied to the tissue in a region within or overlapping the first diffusion zone 1 to trigger release of NO from endogenous stores, thereby creating a second diffusion zone 2. Alternatively, or additionally, photons of a second energy $h\upsilon 2$ may be supplied to stimulate enzymatic generation of NO to increase endogenous stores of NO in the second diffusion zone 2. Photons of a third energy $h\upsilon 3$ may be supplied to the tissue in a region within or overlapping the second diffusion zone 2 to trigger release of endogenous stores, thereby creating a third diffusion zone 3. Alternatively, or additionally, photons of a third energy $h\upsilon 3$ may be supplied to stimulate enzymatic generation of NO to increase endogenous stores of NO in the third diffusion zone 3. In certain embodiments, the first, second, and third diffusion zones 1-3 may have different average depths relative to an outer epidermal surface. In certain embodiments, the first photon energy $h\upsilon 1$, the second photon energy $h\upsilon 2$, and the third photon energy $h\upsilon 3$ may be supplied at different peak wavelengths, wherein different peak wavelengths may penetrate mammalian skin to different depths—since longer wavelengths typically provide greater penetration depth. In certain embodiments, sequential or simultaneous impingement of increasing wavelengths of light may serve to "push" a nitric oxide diffusion zone deeper within mammalian tissue than might otherwise be obtained by using a single (e.g., long) wavelength of light.

In addition to the effect on vascularization brought about by increased NO production and/or release, blue light can also modulate microglial gene expression in the absence of optogenetic protein expression. Blue light, for example, at a wavelength of around 450 nm, repetitively delivered in both long-duration boluses and rapid optogenetic bursts, can alter basal expression of inflammatory and neurotrophic genes in a gene-specific manner. The biggest increases are seen in COX-2 and VEGF-1 expression. For this reason, blue light can both gene expression relevant to revascularizing brain tissue.

Light having a first peak wavelength and a first radiant flux that stimulates enzymatic generation of nitric oxide to increase endogenous stores of nitric oxide may be referred to herein as "endogenous store increasing light" or "ES increasing light." Light having a first peak wavelength and a first radiant flux to release nitric oxide from the endogenous stores may be referred to herein as "endogenous store releasing light" or "ES releasing light." Light having anti-inflammatory effects may be referred to herein as anti-inflammatory light.

In certain embodiments, light at two or three peak wavelengths is used, including one peak wavelength to provide an anti-inflammatory effect, in combination with a peak wavelength of ES releasing light and/or a peak wavelength of ES increasing light. In other embodiments, in place of, or in addition to, ES increasing or ES releasing light, light at one or more wavelengths in the UVA, UVB, or UVC ranges are used.

In other embodiments, the light is administered at wavelengths that reduce inflammation. As discussed above, inflammation is associated with a number of central nervous system disorders, so inhibition of inflammation can treat, prevent, or slow the progression of central nervous system disorders associated with inflammation. Anti-inflammatory wavelengths include, for example, wavelengths of between around 640 and around 680 nm. The wavelength at 850 nm is both anti-inflammatory, by decreasing inflammatory cytokines, and releases NO.

In addition, blue light can reduce pro-inflammatory gene expression in microglia, a type of neuroglia (glial cell) located throughout the brain and spinal cord, and, as such, blue light can mitigate the cytokine storm associated with various neuroinflammatory disorders, such as traumatic brain injury and microbial brain infections.

Photobiomodulation (PBM) at wavelengths of around 660 and around 780 nm can also have an effect on M1 inflammatory markers, such as by lowering the mRNA expression and secretion by microglia and astrocytes of TNF-$\alpha$, iNOS and IL-1$\beta$, with a stronger effect generally observed when light at around 780 nm is used, relative to light at 660 nm. PBM can also significantly reduce the expression and phosphorylation of NF-$\kappa$B p65, and inhibit the generation of reactive oxygen species. This decrease in inflammatory cytokine expression and secretion is observed with light at other wavelengths, but the greatest effects are observed with blue light, which allows for the ability to regulate inflammation in the brain through gene expression.

In certain embodiments, each of the anti-inflammatory light, ES increasing light and/or ES releasing light, and/or UVA/UVB/UVC light has a radiant flux in a range of at least 5 mW/cm², or at least 10 mW/cm², or at least 15 mW/cm², or at least 20 mW/cm², or at least 30 mW/cm², or at least 40 mW/cm², or at least 50 mW/cm², or in a range of from 5 mW/cm² to 60 mW/cm², or in a range of from 5 mW/cm² to 30 mW/cm², or in a range of from 5 mW/cm² to 20 mW/cm², or in a range of from 5 mW/cm² to 10 mW/cm², or in a range of from 10 mW/cm² to 60 mW/cm², or in a range of from 20 mW/cm² to 60 mW/cm², or in a range of from 30 mW/cm² to 60 mW/cm², or in a range of from 40 mW/cm² to 60 mW/cm², or in another range specified herein. Higher fluxes can be used to increase penetration, and effect microbial decontamination, if need be.

In certain embodiments, the ES increasing light has a greater radiant flux than the ES releasing light. In certain embodiments, the ES releasing light has a greater radiant flux than the ES increasing light. In certain embodiments, the anti-inflammatory light has a greater radiant flux than the ES increasing and/or ES releasing light. In certain other embodiments, the anti-inflammatory light has a lesser radiant flux than the ES increasing and/or ES releasing light.

In certain embodiments, where combinations of wavelengths are used, one or both of the anti-inflammatory light and ES increasing and/or ES releasing light has a radiant flux profile that is substantially constant during a treatment window. In certain embodiments, at least one of the anti-inflammatory light and ES increasing and/or ES releasing light has a radiant flux profile that increases with time during a treatment window. In certain embodiments, at least one of the anti-inflammatory light and ES increasing and/or ES releasing light has a radiant flux profile that decreases with time during a treatment window. In certain embodiments, one of the anti-inflammatory light and ES increasing and/or ES releasing light has a radiant flux profile that decreases with time during a treatment window, while the other of the anti-inflammatory light and ES increasing and/or ES releasing light has a radiant flux profile that increases with time during a treatment window.

In certain embodiments, ES increasing and/or ES releasing light is administered such that it increases nitric oxide levels in the brain, and, thus, increases vascularization in the brain. The ES increasing and/or ES releasing light can be administered during a first time window, and anti-inflammatory light can be administered during a second time window, where the anti-inflammatory light is administered to desired areas of the brain, wherein the desired area of the brain may be the same or different, and the second time window may or may not overlap with the first time window. In other embodiments, ES increasing and/or ES releasing light is applied to the tissue during a first time window, anti-inflammatory light is applied to the tissue during a second time window, and the second time is non-overlapping with the first time window. In certain embodiments, the second time window is initiated more than one minute, more than 5 minutes, more than 10 minutes, more than 30 minutes, or more than one hour after conclusion of the first time window. In certain embodiments, ES increasing and/or releasing light is applied to tissue during a first time window, anti-inflammatory light is applied to the tissue during a second time window, and the first time window and the second time window are substantially the same. In other embodiments, the second time window is longer than the first time window.

Aspects of these embodiments where UVA/UVB/UVC light is administered in the same or different time windows, or to the same or different tissue, are also contemplated.

In certain embodiments where combinations of wavelengths are used, one or both of the anti-inflammatory light and ES increasing light and/or ES releasing light may be provided by a steady state source providing a radiant flux that is substantially constant over a prolonged period without being pulsed.

In certain embodiments where combinations of wavelengths are used, one or both of anti-inflammatory light and ES increasing light and/or ES releasing light may include more than one discrete pulse of light. In certain embodiments, more than one discrete pulse of ES increasing and/or ES releasing light is impinged on tissue during a first time window, and/or more than one discrete pulse of anti-inflammatory light is impinged on tissue during a second time window. In certain embodiments, the first time window and the second time window may be coextensive, may be overlapping but not coextensive, or may be non-overlapping.

In certain embodiments where combinations of wavelengths are used, at least one of radiant flux and pulse duration of ES increasing and/or ES releasing light may be reduced from a maximum value to a non-zero reduced value during a portion of a first time window. In certain embodiments, at least one of radiant flux and pulse duration of ES increasing and/or ES releasing light may be increased from a non-zero value to a higher value during a portion of a first time window. In certain embodiments, at least one of radiant flux and pulse duration of anti-inflammatory light may be reduced from a maximum value to a non-zero reduced value during a portion of a second time window. In certain embodiments, at least one of radiant flux and pulse duration of anti-inflammatory light may be increased from a non-zero value to a higher value during a portion of a second time window.

In certain embodiments where combinations of wavelengths are used, each of ES increasing and/or releasing light and the anti-inflammatory light consist of non-coherent light. In certain embodiments, each of the anti-inflammatory light and the ES increasing light and/or ES releasing light consist of coherent light. In certain embodiments, one of the anti-inflammatory light and the ES increasing light and/or the ES releasing light consists of non-coherent light, and the other consists of coherent light.

In certain embodiments where combinations of wavelengths are used, the ES increasing and/or ES releasing light is provided by at least one first light emitting device and the anti-inflammatory light is provided by at least one second light emitting device. In certain embodiments, the ES increasing and/or ES releasing light is provided by a first array of light emitting devices and the anti-inflammatory light is provided by a second array of light emitting devices.

In certain embodiments where combinations of wavelengths are used, at least one of the ES increasing and/or ES releasing light and the anti-inflammatory light is provided by at least one solid state light emitting device. Examples of solid state light emitting devices include (but are not limited to) light emitting diodes, lasers, thin film electroluminescent devices, powdered electroluminescent devices, field induced polymer electroluminescent devices, and polymer light-emitting electrochemical cells. In certain embodiments, the ES increasing and/or ES releasing light is provided by at least one first solid state light emitting device and the anti-inflammatory light is provided by at least one second solid state light emitting device. In certain embodiments, the anti-inflammatory and the ES increasing light and/or ES releasing light may be generated by different emitters contained in a single solid state emitter package, wherein close spacing between adjacent emitters may provide integral color mixing. In certain embodiments, the anti-inflammatory light may be provided by a first array of solid state light emitting devices and the ES increasing and/or ES releasing light may be provided by a second array of solid state light emitting devices.

In certain embodiments where combinations of wavelengths are used, an array of solid state emitter packages each including at least one first emitter and at least one second emitter may be provided, wherein the array of solid state emitter packages embodies a first array of solid state emitters arranged to generate ES increasing and/or ES releasing light and embodies a second array of solid state emitters arranged to generate anti-inflammatory light. In certain embodiments, an array of solid state emitter packages may embody packages further including third, fourth, and/or fifth solid state emitters, such that a single array of solid state emitter packages may embody three, four, or five arrays of solid state emitters, wherein each array is arranged to generate a emissions with a different peak wavelength.

In certain embodiments where combinations of wavelengths are used, at least one of anti-inflammatory and the ES increasing light and/or the ES releasing light is provided by at least one light emitting device devoid of a wavelength conversion material.

In certain embodiments where combinations of wavelengths are used, the anti-inflammatory light consists of substantially monochromatic light and the ES increasing light and/or ES releasing light consists of substantially monochromatic light. In certain embodiments, the ES increasing light includes a first spectral output having a first full width at half maximum value of less than 25 nm (or less than 20 nm, or less than 15 nm, or in a range of from 5 nm to 25 nm, or in a range of from 10 nm to 25 nm, or in a range of from 15 nm to 25 nm), and/or the ES releasing light includes a second spectral output having a second full width at half maximum value of less than 25 nm (or less than 20 nm, or less than 15 nm, or in a range of from 5 nm to 25 nm, or in a range of from 10 nm to 25 nm, or in a range of from 15 nm to 25 nm).

In certain embodiments where combinations of wavelengths are used, the anti-inflammatory light is produced by one or more first light emitters having a single first peak wavelength, and the ES increasing light and/or ES releasing light is produced by one or more second light emitters having a single second peak wavelength. In other embodiments, the anti-inflammatory light may be produced by at least two light emitters having different peak wavelengths (e.g., differing by at least 5 nm, at least 10 nm, at least 15 nm, at least 20 nm, or at least 25 nm), and/or the ES increasing and/or the ES releasing light may be produced by at least two light emitters having different peak wavelengths (e.g., differing by at least 5 nm, at least 10 nm, at least 15 nm, at least 20 nm, or at least 25 nm).

Ultraviolet light (e.g., UV-A light having a peak wavelength in a range of from 350 nm to 395 nm, and UV-B light having a peak wavelength in a range of from 320 nm to 350 nm) may be effective as ES increasing light; however, overexposure to ultraviolet light may not be preferred, as it can lead to tissue damage. That said, UVC light can also be particularly effective at treating or preventing microbial infections. While damage to the tissue being exposed to these wavelengths should be minimal, it may cause some detrimental effects on long-term exposure. It may therefore be desirable to use shorter cycles of UV light than non-UV light.

In certain embodiments, UV light (e.g., having peak wavelengths in a range of from 320 nm to 399 nm) may be used as ES increasing light; however, in other embodiments, UV light may be avoided.

The combination of light at these (UVA, UVB, and/or UVC) wavelengths with the anti-inflammatory light can minimize these effects.

In certain embodiments, ES increasing light and ES releasing light are substantially free of UV light. In certain embodiments, less than 5% of the ES increasing light is in a wavelength range of less than 400 nm, and less than 1% of the ES releasing light output is in a wavelength range of less than 400 nm. In certain embodiments, ES increasing light includes a peak wavelength in a range of from 400 nm to 490 nm, or from 400 nm to 450 nm, from 400 nm to 435 nm, or from 400 nm to 420 nm.

In certain embodiments, ES increasing light may include a wavelength range and flux that may alter the presence, concentration, or growth of bacteria or other microbes in or on the tissue receiving the light. UV light and near-UV light (e.g., having peak wavelengths from 400 nm to 435 nm, or more preferably from 400 nm to 420 nm) in particular may affect microbial growth.

Effects on microbial growth may depend on the wavelength range and dose. In certain embodiments, ES increasing light may include near-UV light having a peak wavelength in a range of from 400 nm to 420 nm to provide a microbicidal/bacteriostatic effect (e.g., with pulsed light having a radiant flux of <9 mW/cm$^2$), provide a bactericidal effect (e.g., with substantially steady state light having a radiant flux in a range of from 9 mW/cm$^2$ to 17 mW/cm$^2$), or provide an antimicrobial effect (e.g., with substantially steady state light having a radiant flux in a range of greater than 17 mW/cm$^2$, such as in a range of from 18 mW/cm$^2$ to 60 mW/cm$^2$).

In certain embodiments, ES increasing light in a near-UV range (e.g., from 400 nm to 420 nm) may also affect microbial growth in the brain (whether in a microbicidal/bacteriostatic range, bactericidal range, or an antimicrobial range), in addition to increasing vascularization in the brain. Such light can therefore be used for inhibiting infections in the brain tissue, in addition to increasing vascularization.

In certain embodiments, ES releasing light may include a peak wavelength in a range of from 500 nm to 900 nm, or in a range of from 490 nm to 570 nm, or in a range of from 510 nm to 550 nm, or in a range of from 520 nm to 540 nm, or in a range of from 525 nm to 535 nm, or in a range of from 528 nm to 532 nm, or in a range of about 530 nm.

The wavelength at 660 nm is both anti-inflammatory, and releases NO.

A combination of equal parts of 410 nm light and 530 nm light is equally as effective as 530 nm light alone. Such a combination may be beneficial since a 410 nm blue LED is significantly more efficient than a 530 nm green LED, such that a combination of equal parts of 410 nm LED emissions and 530 nm LED emissions may use 26% less electric power than emissions of a 530 nm LED alone, when operated to provide the same radiant flux.

Light at 660 nm is significantly less effective than the 530 nm green light at releasing NO from Hb-NO. The release of NO from Hb-NO appears to be the same for 530 nm green light, 660 nm red light, and a combination of 530 nm green and 660 nm light for the time window of from 0 seconds to about 2000 seconds, but the effectiveness of the different sources diverges thereafter. Without intending to be bound by any particular theory or explanation of this phenomenon, it is suggested that NO binds to Hb-NO at multiple sites, and that removal of a second or subsequent NO molecule from Hb-NO may require more energy than removal of a first NO molecule, perhaps due to a change in shape of the Hb-NO after removal of a first NO molecule.

In certain embodiments, anti-inflammatory light having a first peak wavelength is impinged on the tissue surrounding the injected biosensor, and ES increasing or ES releasing light that includes light having a second peak wavelength is also impinged on this tissue, and furthermore a light having a third peak wavelength (i.e., ES releasing or ES increasing light) may be impinged on this tissue. In certain embodiments, the light having a third peak wavelength may be provided at substantially the same time as (or during a time window overlapping at least one time window of) one or both of the anti-inflammatory and the ES increasing and/or ES releasing light.

In certain embodiments, the light having a third peak wavelength differs from each of the first peak wavelength and the second peak wavelength by at least 10 nm. In certain embodiments, the light having a third peak wavelength exceeds the second peak wavelength by at least 20 nm. In certain embodiments, the light having a third peak wavelength is provided with a radiant flux in a range of from 5 mW/cm$^2$ to 60 mW/cm$^2$. In certain embodiments, the third peak wavelength is in a range of from 600 nm to 900 nm, or in a range of from 600 nm to 700 nm. In certain embodiments, the third peak wavelength is in a range of from 320 nm to 399 nm.

In certain embodiments, the anti-inflammatory light is in a range of from about 630 nm to 670 nm (e.g., including specific wavelengths of about 630 nm and about 660 nm) may be useful to provide anti-inflammatory effects and/or to promote vasodilation. Anti-inflammatory effects may be useful in treating, preventing, or slowing the progression of various central nervous system disorders.

In some embodiments, when light at one or more wavelengths are used, the light can be coherent or incoherent, or mixtures thereof.

In some embodiments where different wavelengths are administered, light can be administered at different power densities/durations, for example, to provide shorter exposure to UVC to avoid damaging tissue, and longer exposure to anti-inflammatory wavelengths.

Neurotransmitter Production Via Exposure to Specific Wavelengths

Several CNS disorders are associated with decreased levels of various neurotransmitters. As discussed below, specific wavelengths of light can be used to enhance production of various neurotransmitters. Serotonin is a neurotransmitter that affects memory and learning, regulates anger and aggression, and is a component of anxiety disorders, such as depression, obsessive-compulsive disorder. When present in excessive levels, it can cause Alzheimer's disease. Dopamine is a neurotransmitter that is associated with ADHD, hyperactive adults, bi-polar disorder, and social anxiety, and also regulates pain. If dopamine levels are too high, it can result in psychosis or schizophrenia. Norepinephrine is associated with increased alertness, arousal, and the reward system. Acetycholine deficiencies are associated with Alzheimer's disease and loss of memory and learning.

According to some embodiments, light in the range of 260-400 nm may be used to penetrate the orbit, eye, and eventually into the deep brain structures of the frontal lobes to regulate dopamine levels because of the tyrosinase enzyme.

A pigment in human eyes called melanopsin acts as a receptor that can signal the production or suppression of melatonin, the hormone that regulates sleep and wakefulness. Melanopsin is triggered by specific wavelengths of light and is most sensitive to wavelengths at and around 480 nm.

ipRGCs (intrinsically photosensitive retinal ganglion cells) contain melanopsin, and shining light at the right wavelength to the optic nerve, and, indirectly, to the pineal gland, can spark neurotransmitter, hormone and enzyme production, which can help with certain behavioral and mood disorders. These cells are particularly sensitive to blue light, specifically blue light with a peak at around 470 nm. By exposing the patient to blue light, such that the light enters and falls on the lower back portion of the retina, the ipRGCs can cause increased neurotransmitter levels.

The melanocortin receptor (MC4R) in the eye, when exposed to light at appropriate wavelengths, can reverse memory impairment caused by fibrous amyloid protein plague build up. Amyloid protein is stimulated by light, particularly blue light. Blue light triggers the MC4R receptor in the eye and hypothalmus and keeps the protein energized to not form amyloid plaques.

Blue light reduces nocturnal melatonin, and both blue and red lights affect cortisol and alpha amylase levels (see, for example, Figueiro M G, Rea M S. The effects of red and blue lights on circadian variations in cortisol, alpha amylase, and melatonin. Int J Endocrinol. 2010; 2010:829351).

Blue light can increase neuronal activity-regulated gene expression in the absence of optogenetic proteins. One hour of exposure to blue light, but not red or green light, results in an increase in the expression of neuronal activity-regulated genes.

The frequency at which the light is pulsed can also have an effect. For example, when blue light is pulsed from 10 Hz to 100 Hz, one can obtain a 3 fold increase in expression with the same duration of exposure, at the same wavelength, when the light is emitted at a frequency outside of this range.

Location of the Light Irradiation

Some diseases are not area-specific. That is, some diseases are not necessarily due to a specific damaged area of the brain, instead occurring throughout the brain, or at a different location for each patient, such as Creutzfeldt-Jakob disease, hypothyroidism, Lewy body dementia, normal pressure hydrocephalus, tauopathies, and vascular dementia.

For example, with vascular dementia, blood vessels throughout the brain may be affected, some more than others. When treating these disorders, light can be applied all over the head. For an inflammation-based disease such as Parkinson's, the more areas of the brain that can be treated the more effective treatment is. For some diseases, the treatment can be applied to acupuncture points on the brain.

In some embodiments, the treatment is applied to a specific hemisphere of the brain, though this level of specificity need not be used. For example, Alzheimer's can be treated by targeting the frontal cortex, temporal lobe, and base. Amyotrophic lateral sclerosis (ALS) can be treated by targeting the motor cortex. Autism spectrum disorder can be treated by targeting the frontal cortex, temporal lobe, and/or the base of the skull. Epileptic seizures can be treated by targeting the cortex. Huntington's disease can be treated by targeting the basal ganglia. Parkinson's disease can be treated by targeting the midbrain. Pick's disease, and other fronto-temporal dementias, can be treated by targeting the frontal lobe.

The Use of Pulse Frequencies

Regardless of the device that is used, the applied light energy can be applied with pulse frequencies that mimic healthy brain function of alpha, beta, delta, and theta waves. The pulse frequencies can be applied in series, alternately, or simultaneously. The light can be emitted from the same light emitter or from multiple emitters. Delta waves have an approximate frequency range of 0.5 to 3 Hz, and their main source location in the human brain is the thalamus or cortex. Theta waves have an appropriate frequency range of 3 to 8 Hz, and their main source location in the human brain is the hippocampus. Alpha waves have an approximate frequency range of 8 to 12.5 Hz, and their main source location in the human brain is the occipital lobe. Mu waves have an approximate frequency range of 7.5 to 12.5 Hz, primarily between 9 and 11 Hz, and their main source location in the human brain is the motor cortex. Beta waves have an approximate frequency range of 12.5 to 38 Hz, and their main source location in the human brain is the posterior brain. Gamma waves have an approximate frequency range of 38 to 100 Hz, and are located in all areas of the brain.

In some embodiments, the light energy is applied with a pulse frequency of around 40 Hz, which can be used to treat Alzheimer's disease by reducing amyloid plaques. In some embodiments, light energy having a frequency of about 30 Hz to about 50 Hz, and more specifically about 40 Hz, is non-invasively delivered to the subject to entrain gamma oscillations in multiple brain regions of the subject. These regions include the prefrontal cortex (PFC) and the hippocampus, and can further include the visual cortex, the somatosensory cortex, the hippocampus and the prefrontal cortex of the subject. This light energy can be administered alone or in combination with chronic visual stimuli having a frequency of about 30 Hz to about 50 Hz, and more specifically about 40 Hz. The entrained gamma oscillations modulate neuronal activity across multiple brain regions (e.g., facilitate functional binding of neural networks at low gamma frequencies) to induce various neuroprotective effects (e.g., amelioration of amyloid plaques and tau hyperphosphorylation) and reduce neurodegeneration.

Neuronal activity reduces an immune response in microglia and ameliorates aberrantly modified genes and proteins involved in membrane trafficking, intracellular transport, synaptic function, neuroinflammation and DNA damage response. Behavior modification, including enhanced learning and memory, can be achieved.

In other embodiments, the light energy is applied with a pulse frequency in the range of alpha, beta, delta, and/or theta waves, and this can help with treating Parkinson's disease.

Pulsed electromagnetic field therapy, including at pulse frequencies in the same ranges, can be used in combination with the light therapies described herein, even in embodiments where the light is not pulsed. Pulsed electromagnetic field therapy (PEMFT, or PEMF therapy), also known as low field magnetic stimulation (LFMS) treats patients by using electromagnetic fields. The majority of PEMF wellness devices resemble a typical yoga mat in dimensions but are slightly thicker to house several flat spiral coils to produce an even electromagnetic field. A frequency generator energizes the coils to create a pulsed electromagnetic field.

V. Methods of Treatment

The methods described herein can be used to treat a variety of CNS disorders, particularly those with an inflammatory component, and/or those associated with poor vascularization in one or more regions of the brain. These disorders include cognitive disorders, motor disorders, and behavioral/mood disorders.

Additionally, passage of light at appropriate wavelengths can heal damage to the blood-brain barrier, and assist with the passage of drugs through the blood-brain barrier. Accordingly, the methods can be used to assist with the treatment of brain cancer and other brain disorders.

The methods involve applying light to the brain of a patient in need of treatment of a cognitive disorder, at an appropriate wavelength or combination of wavelengths, at a suitable power and for a suitable period of time, to treat the disorder.

In disorders with an inflammatory component, the light can be administered at anti-inflammatory wavelengths. In disorders with a vascular component, the light can be administered at wavelengths which promote increased vascularization, for example, by promoting endogenous NO production and/or release.

In some embodiments, light is applied generally to the brain. In other embodiments, light is applied near the area of the brain that is malfunctioning or that is associated with the source of the disease to be treated.

In still other embodiments, the treatment is enhanced by activating the cranial nerves while the light is applied.

On information and belief, it will take at least one week, and in some cases, approximately 2-4 weeks of therapy to see beneficial effects, and the effectiveness of the therapy will decline within two weeks to a month after therapy is terminated.

Types of Disorders that can be Treated

The treatments described herein can be used to treat a number of different disorders, including neurocognitive disorders, movement disorders, and emotional/behavioral/mood disorders.

The treatments can also increase the flow of drugs across the blood brain barrier, so can be used to treat disorders of the brain, such as cancer, or disorders associated with an impaired blood brain barrier.

Disorders Associated with an Impaired Blood Brain Barrier

Disorders associated with an impaired blood brain barrier include Alzheimer's disease (van de Haar H J, et al., "Blood-Brain Barrier Leakage in Patients with Early Alzheimer Disease". Radiology. 282 (2): 615 (February 2017)), anxiety and depression (Gal Z, Huse R J, Gonda X, Kumar S, Juhasz G, Bagdy G, Petschner P (March 2019). "[Anxiety and depression—the role of blood-brain barrier integrity]". Neuropsychopharmacologia Hungarica. 21 (1): 19-25), brain abscesses (caused by inflammation and collection of lymphatic cells and infected material originating from a local or remote infection), De Vivo disease (also known as GLUT1 deficiency syndrome, resulting from inadequate transportation of the sugar glucose across the blood-brain barrier, typically caused by genetic defects in glucose transporter type 1 (GLUT1), HIV encephalitis (Ivey N S, MacLean A G, Lackner A A (April 2009). "Acquired immunodeficiency syndrome and the blood-brain barrier". Journal of Neurovirology. 15 (2): 111-22), Meningitis (associated with inflammation of the membranes that surround the brain and spinal cord, i.e., meninges), multiple sclerosis (Waubant E (2006). "Biomarkers indicative of blood-brain barrier disruption in multiple sclerosis". Disease Markers. 22 (4): 235-44), and neuromyelitis optica, also known as Devic's disease, which is similar to multiple sclerosis.

Types of Brain Cancer

Representative types of brain cancers that can be treated include astrocytomas, including gliomas, glioblastoma multiforme, and meningiomas, ependymomas, pituitary tumors, such as pituitary adenomas and pituitary carcinomas, craniopharyngiomas, germ cell tumors, such as germinomas, pineal region tumors, including slow growing (pineocytoma) and fast growing (pineoblastoma) tumors, medulloblastomas, and primary CNS lymphomas.

When used to treat brain cancers, conventional anticancer drugs can be used, and their passage across the blood brain barrier can be enhanced, thus maximizing treatment efficiency. Representative anticancer drugs include 5FC, Accutane, AEE788 (Novartis), AMG-102, Anti Neoplaston, AQ4N (Banoxantrone), AVANDIA (Rosiglitazone Maleate), Avastin (Bevacizumab) BCNU, BiCNU, Carmustine, Carboplatin, CC-223, CC223, CCI-779, CCNU, CCNU Lomustine, Celecoxib (Systemic), Chloroquine, Cilengitide (EMD 121974), Cisplatin, CPT-11 (CAMPTOSAR, Irinotecan), Cytoxan, Dasatinib (BMS-354825, Sprycel), Etoposide (Eposin, Etopophos, Vepesid), GDC-0449, Gleevec (imatinib mesylate), GLIADEL Wafer, Hydroxychloroquine, Hydroxyurea, IL-13, IMC-3G3, Immune Therapy, Iressa (ZD-1839), Lapatinib (GW572016), Methotrexate, Novocure, OSI-774, PCV, Procarbazine, RAD001 Novartis (mTOR inhibitor), Rapamycin (Rapamune, Sirolimus), RMP-7, RTA 744, Simvastatin, Sirolimus, Sorafenib, SU-101, SU5416 Sugen, Sulfasalazine (Azulfidine), Sutent (Pfizer), Tamoxifen, TARCEVA (erlotinib HCl), Taxol, TEMODAR, TEMODAR Schering-Plough Thalomid (thalidomide), Toca 511, Topotecan (Systemic), VEGF Trap, VEGF-Trap, Velcade, Vincristine, Vorinostat (SAHA), XL 765, XL-184, XL184, XL765, Zarnestra (tipifarnib), and Zocor (simvastatin). Dexamethasone and furosemide can be used to decrease swelling.

Brain infections can also be treated adjuvantly, using conventional antimicrobial agents.

CNS Disorders Associated with Inflammation

Central nervous system (CNS) vasculitis is inflammation of blood vessel walls in the brain or spine, which make up the central nervous system. CNS vasculitis is often accompanied by other autoimmune diseases such as systemic lupus erythematosus, dermatomyositis, and, rarely, rheumatoid arthritis. It is often caused by a viral or bacterial infection and can be systemic. When the vasculitis is only confined to the brain or the spinal cord, it is referred to as primary angiitis of the CNS (PACNS).

Neurocognitive Disorders

There are a number of neurocognitive disorders (also known as cognitive disorders) that can be treated using the treatments described herein. Examples include Alzheimer's disease, amnesia, Binswanger's disease, cerebellar cognitive affective syndrome, clinical dementia rating, clouding of consciousness, cognitive deficit, cognitive slippage, cognitive vulnerability, corticobasal degeneration, corticobasal syndrome, delirium, dementia, disabilities affecting intellectual abilities, frontal assessment Battery, frontotemporal dementia, frontotemporal dementia and parkinsonism linked to chromosome 17, frontotemporal lobar degeneration, HIV-associated neurocognitive disorders, learning problems in childhood cancer, Lewy body dementia association, Lewy body dementia, logopenic progressive aphasia, mild cognitive impairment, paratonia, Pick's disease, post-chemotherapy cognitive impairment, postoperative cognitive dysfunction, primary progressive aphasia, progressive nonfluent aphasia, progressive supranuclear palsy, pseudosenility, REM sleep behavior disorder, semantic dementia, severe cognitive impairment, subcortical dementia, and vascular dementia.

Neurocognitive disorders can have numerous causes, including genetics, brain trauma, stroke, and heart issues. The main causes are neurodegenerative diseases such as Alzheimer's disease, Parkinson's disease, and Huntington's disease because they affect or deteriorate brain functions. Other diseases and conditions that cause NDCs include vascular dementia, frontotemporal degeneration, Lewy body disease, prion disease, normal pressure hydrocephalus, and dementia/neurocognitive issues due to HIV infection. They may also include dementia due to substance abuse or exposure to toxins.

Neurocognitive disorders also include brain trauma, including concussions and traumatic brain injuries, as well as post-traumatic stress and alcoholism. This is referred to as amnesia, and is characterized by damage to major memory encoding parts of the brain such as the hippocampus. Difficulty creating recent term memories is called anterograde amnesia and is caused by damage to the hippocampus part of the brain. Retrograde amnesia is also caused by damage to the hippocampus, but the memories that were encoded or in the process of being encoded in long-term memory are erased.

Movement Disorders

Movement disorders are clinical syndromes with either an excess of movement or a paucity of voluntary and involuntary movements, unrelated to weakness or spasticity, and are typically divided into two major categories—hyperkinetic and hypokinetic. Hyperkinetic movement disorders refer to dyskinesia, or excessive, often repetitive, involuntary movements that intrude upon the normal flow of motor activity. Hypokinetic movement disorders refer to akinesia (lack of movement), hypokinesia (reduced amplitude of movements), bradykinesia (slow movement), and rigidity. In primary movement disorders, the abnormal movement is the primary manifestation of the disorder. In secondary movement disorders, the abnormal movement is a manifestation of another systemic or neurological disorder.

Representative movement disorders include hypokinetic movement disorders, Parkinson's disease (Primary or Idiopathic Parkinsonism), secondary Parkinsonism, Parkinson plus syndromes, Hallevorden-Spatz Disease, progressive supranuclear ophthalmoplegia, striatonigral deneneration, hyperkinetic movement disorders, dystonia, including drug-induced dystonia, idiopathic familial dystonia, idiopathic non-familial dystonia, ideopathic orofacial dystonia, spasmodic torticollis, blepharospasm, and other other dystonias, extrapyramidal movement disorders, essential tremors, drug induced tremors, myoclonus, opsoclonus, chorea (rapid, involuntary movement), including drug-induced chorea, rheumatic chorea (Sydenham's chorea), and Huntington's Chorea, ballismus (violent involuntary rapid and irregular movements), hemiballismus (affecting only one side of the body), athetosis (contorted torsion or twisting), dyskinesia (abnormal, involuntary movement), tardive dyskinesia, tic disorders (involuntary, compulsive, repetitive, stereotyped), including Tourette's syndrome and drug-induced tics and tics of organic origin, stereotypic movement disorder, paroxysmal nocturnal limb movement, painful legs (or arms), moving toes (or fingers) syndrome, sporadic restless leg syndrome, familial restless leg syndrome, stiff-person syndrome, abnormal head movements, cramp and spasm, and fasciculation.

53

54

Emotional/Behavioral/Mood Disorders

Emotional and behavioral disorders (EBD; also known as behavioral and emotional disorders (ICD-10)) refer to a disability classification used in educational settings that allows educational institutions to provide special education and related services to students who have displayed poor social and/or academic progress.

Disruptive behavior disorders include attention-deficit hyperactivity disorder (ADHD), oppositional defiant disorder (ODD), and conduct disorders (CD). Schizophrenia is also included in this definition.

Anxiety disorders are also included. Representative anxiety disorders include generalized anxiety disorder, specific phobia, social anxiety disorder, separation anxiety disorder, agoraphobia, panic disorder, and selective mutism. Anxiety disorders often occur with other mental disorders, particularly major depressive disorder, personality disorder, and substance use disorder.

Depressive disorders include major depressive disorder (MDD, also known as major depression, unipolar depression, or clinical depression), and there are several subtypes or course specifiers, including atypical depression (AD), melancholic depression, psychotic major depression (PMD, or simply psychotic depression), catatonic depression, postpartum depression, premenstrual dysphoric disorder (PMDD), seasonal affective disorder (SAD), dysthymia, double depression, depressive personality disorder (DPD), recurrent brief depression (RBD), minor depressive disorder (minor depression), and depressive disorder not otherwise specified (DD-NOS), which encompasses "any depressive disorder that does not meet the criteria for a specific disorder."

Bipolar disorders (BD, also called manic depression or manic-depressive disorder), including bipolar I, bipolar II, cyclothymia, and bipolar disorder not otherwise specified (BD-NOS, or "sub-threshold" bipolar).

Certain mood disorders are substance-induced, including alcohol-induced and benzodiazepine-induced.

Medications, such as antidepressants, benzodiazepines, or beta blockers, may be used in combination with the treatments described herein.

Specific pharmaceutical treatment regimens for various disorders discussed herein are outlined below.

Combination Treatment for Parkinson's Disease

While there is no cure for Parkinson's disease, a number of different types of medications provide some relief. The main families of drugs useful for treating motor symptoms are levodopa (typically combined with a dopa decarboxylase inhibitor and sometimes also with a COMT inhibitor), dopamine agonists and MAO-B inhibitors. Representative dopamine agonists include bromocriptine, pergolide, pramipexole, ropinirole, piribedil, cabergoline, apomorphine and lisuride. Representative MAO-B inhibitors include safinamide, selegiline and rasagiline.

Those of skill in the art appreciate that the stage of the disease and the age at disease onset determine which group is most useful. Braak staging of Parkinson's disease gives six stages that can be used to identify early stages, later stages, and late stages. The initial stage in which some disability has already developed and requires pharmacological treatment is followed by later stages associated with the development of complications related to levodopa usage, and a third stage when symptoms unrelated to dopamine deficiency or levodopa treatment may predominate.

Typically, only 5-10% of levodopa crosses the blood-brain barrier. Much of the remainder is metabolized to dopamine elsewhere in the body, causing a variety of side effects including nausea, vomiting and orthostatic hypotension.

Carbidopa and benserazide are dopa decarboxylase inhibitors which do not cross the blood-brain barrier and inhibit the conversion of levodopa to dopamine outside the brain, reducing side effects and improving the availability of levodopa for passage into the brain. One of these drugs is usually taken along with levodopa, often combined with levodopa in the same pill.

Because the treatments described herein can increase the passage of drugs through the blood-brain barrier, it is possible to lower the dosage of levodopa while still achieving the same degree of efficacy, and, therefore, reducing side effects, including dyskinesias.

Intestinal infusions of levodopa (Duodopa) can also be used, and can reduce dosage fluctuations relative to oral levodopa.

Catechol-O-methyltransferase (COMT) inhibitors such as opicapone, entacapone and tolcaponecan be used in combination with levodopa and dopamine dearecarboxylase (DDC) inhibitors to inhibit peripheral levodopa metabolism, increasing the amount of levodopa delivered to the brain. Other drugs such as amantadine, anticholinergics, quetiapine, cholinesterase inhibitors, modafinil, pimavanserin, doxepin and rasagline can also be used.

Combination Treatment for Alzheimer's Disease and Other Cognitive Disorders

In addition to the treatments described herein, various drugs have been developed for use with Alzheimer's patients, and these can be used in combination with the treatments. Representative compounds that can be administered include memantine, Solanezumab, aducanumab, compounds which reduce beta-amyloid levels, such as apomorphine and aducanumab, vaccines that train the immune system to recognize, attack, and reverse deposition of amyloid, such as ACC-001 and bapineuzumab, and antisense therapies, neuroprotective agents, such as AL-108, metal-protein interaction attenuation agents, such as PBT2, TNFα receptor-blocking compounds, such as the fusion protein, etanercept, tau aggregation inhibitors, such as methylthioninium chloride and its prodrug LMTX, antihistamines, such as dimebon, and beta-secretase protein inhibitors, such as verubecestat, which reduced amyloid beta concentrations. Medications that reduce oxidative stress can improve memory, and can therefore be co-administered. Treatments that reduce amyloid-β not only improve memory but also reduce oxidative stress.

As discussed elsewhere herein, in animal models, such as the senescence accelerated mouse (SAMP8) model, amyloid precursor protein (APP) is overproduced. The blood-brain barrier is damaged, causing a decreased expulsion of amyloid-β protein from the brain, and causing an increase in oxidative stress in the brain.

The use of the treatments described herein can increase the ability of agents to cross the blood brain barrier, so can enhance the effectiveness of these agents, as well as accelerate expulsion of amyloid-β protein from the brain.

Additional Combination Treatments

In addition to light, and the pharmaceutical adjunct therapies discussed herein, additional treatments that can be used in combination with light include PEMF or other magnetic field treatments, traditional Chinese medicine/color-puncture, stimulation of acupuncture/trigger points (1-40 mm), Bonghan channel hyaluronic acid/stem cell treatments, behavioral healthcare/psychiatric treatments (cognitive-behavioral, biofeedback, EMDR, and/or deep relaxation).

VI. Methods for Following the Course of Treatment

There are several ways to monitor the course of treatment, and these will vary depending on whether the CNS disorder being treated is a cognitive, motor, or behavioral disorder, or a brain tumor.

For many of these disorders, treatment can be followed, for example, by following changes in blood pressure, blood flow, pulse, heart rate variability, blood oxygen saturation, electromyocardiographic response, respiration rate, respiration pattern, galvanic skin response, pupil dilation, trabecular-ciliary process distance, magnetic resonance imaging, brain waves, physical movements, muscle tension, self-reporting, and combinations thereof.

A therapy session can begin by explaining to the patient the proposed treatments, along with a discussion of the risks and benefits of different approaches, in the usual fashion for any medical procedure. The patient can be placed in a chair, bed, enclosure, or the like, and an appropriate light-emitting device, as described herein, can be applied to the patient.

Power can then be applied to the light source, and other components of the phototherapy system. In some embodiments, an operator, which can be the patient, can enter a desired wavelength, duration, intensity and/or treatment time. Using these settings, light is emitted onto the patient, in some embodiments such that it can pass through the cranium and/or brain, for the given length of time.

One approach to monitoring the success of the treatment is to measure various indicators at the time the therapy is administered. For example, detectors (e.g. photodiodes, phototransistors, photoresistors, etc.) can record transmitted and scattered light, whether for information purposes, or to control one or more system functions. After the therapy session is completed, the light and any detection means can be deactivated, and the patient can be informed that therapy has concluded. Following the therapy session, the results of the phototherapy can be evaluated through an examination procedure.

Additionally or alternatively, a patient physiology monitor may be used as a feedback source that is connected to feedback/control lines to provide feedback that can be used to perform active control (e.g., amplitude control, etc.) of the dose (e.g., intensity, duration, wavelength, etc.) delivered by the light sources. A patient physiology monitor may monitor one or more aspects of the patent for signs of the effective dose and amount of energy delivered to the internal target area. For example, the monitor may analyze air exhaled by the patient to identify an increased concentration of nitric oxide in the exhaled air, which is an indication that the brain is being stimulated to produce more endogenous nitric oxide. Similarly, the patient's blood pressure can be evaluated, since nitric oxide has a role in the control of blood flow and blood pressure via activation of the heme enzyme, soluble guanylate cyclase.

The system can optionally include look for levels of optical absorbers/scatterers, such as cytochrome c oxidase or hemoglobin (in its oxygenated and deoxygenated states). One can use one or more wavelengths to perform spectrophotometric measurements, and thus perform noninvasive measurement of various biochemical processes. The information thus obtained can help identify and maintain a proper dose of light during a therapy session, and determine a desired and/or minimum effective dose.

Similarly, one can identify other parameters for a suitable therapy session, for example, by varying the wavelength, intensity and/or time and looking for appropriate physiological responses. For example, instead of starting at a minimum dose and incrementally increasing the dose, a base wavelength may be initially used and incrementally adjusted to identify an optimum wavelength. To this end, the feedback systems can be used to non-invasively identify desirable operational parameters of near-IR light entering the target area, such as identifying a minimum dose of light needed to perform the desired therapy on the target area.

These approaches can provide nearly immediate feedback as to whether the therapy is working. However, it can also be important to follow the course of therapy over time, to determine whether a disease state has been eliminated, its progression has been reversed, or its progression appears to have been slowed down. The steps for long-term monitoring will vary depending on the disorder being treated.

Long-Term Monitoring of Cognitive Disorders

When treating cognitive disorders, such as Alzheimer's Disease (AD), mild cognitive impairment (MCI), traumatic brain injury (TBI), and the like, the success of therapy can be periodically evaluated using mental acuity tests. One such test is the Mini-Mental State Examination (MMSE) or Folstein test, which is a 30-point questionnaire used extensively in clinical and research settings to measure cognitive impairment. It is commonly used to screen for dementia, and to estimate the severity and progression of cognitive impairment and to follow the course of cognitive changes in an individual over time. As such, it is an effective way to document an individual's response to treatment.

Administration of the test (a standard MMSE form which is currently published by Psychological Assessment Resources) takes between 5 and 10 minutes and examines functions including registration (repeating named prompts), attention and calculation, recall, language, ability to follow simple commands and orientation.

The MMSE has validity and reliability for diagnosing and assessing Alzheimer's disease and other cognitive disorders. Other tests can also be used, such as the Hodkinson Abbreviated Mental Test score, the Geriatric Mental State Examination (GMS), or the General Practitioner Assessment of Cognition, bedside tests such as the 4AT (which also assesses for delirium), and computerized tests such as CoPs and Mental Attributes Profiling System, as well as longer formal tests for deeper analysis of specific deficits.

In addition to these tests, one can also perform brain scans, for example, using SPECT, PET, or MRI imaging techniques. Additional devices can be used include functional Near-Infrared Spectroscopy (fNIRS) devices, Magnetoencephalography (MEG) devices and Electroencephalography (EEG) devices.

If these brain scans are carried out while therapy is being administered, based on an analysis of the subject's brain activity, one or more operational parameters of the light energy, such as wavelength, flux, fluence, and/or treatment time, can be adjusted.

As disclosed in U.S. Pat. No. 9,950,189, one can target treatment using SPECT functional neuroimaging followed by quantitative analysis, and target treatment of spinal cord or nerve-related disorders using neurophysiological testing followed by quantitative analysis. Serial SPECT neuroimaging, coupled with quantitative analysis and/or using serial neurophysiological testing followed by quantitative analysis can elucidate changes in response to treatment.

In one embodiment, a first SPECT neuroimaging scan of a patient is obtained, and analyzed to identify one or more areas of the patient's brain to be treated. The light is targeted to those areas. A second SPECT scan can be performed, and analyzed in conjunction with the first SPECT scan to evaluate and characterize changes in the neurological disorder. In addition to SPECT scans, PET and MRI scans can also be used.

Those of skill in the art know how to perform perfusion single photon emission computed tomography (SPECT) scans (see, for example, Raji C A, et al. Clinical utility of SPECT neuroimaging in the diagnosis and treatment of traumatic brain injury: a systematic review. PLoS One. 2014; 9(3):e91088, 2014).

Particularly with respect to cognitive disorders such as mild cognitive impairment (MCI) neuroimaging, particularly SPECT neuroimaging with quantitative analysis, can diagnose these disorders with an accuracy typically in the high 80% range (see, for example, Henderson, T A. The diagnosis and evaluation of dementia and mild cognitive impairment with emphasis on SPECT perfusion neuroimaging. CNS Spectrums, 17(4):176-206, 2012). SPECT neuroimaging can be extremely helpful in evaluating CNS disorders with a vascular component, such as vascular dementia.

Perfusion SPECT can also be used to distinguish IPD from other Parkinsonian syndromes, such as MSA or PSP (see, for example, Markus H S, et al., HMPAO SPECT in Parkinson's disease before and after levodopa: correlation with dopaminergic responsiveness. J Neurol Neurosurg Psychiatry, 57:180-185, 1994). A progressive increase in striatal perfusion has been correlated with increasing symptom severity. A correlation between striatal perfusion (or glucose metabolism) changes and progression of the disease symptoms has been recognized (Kuhl D E, et al., Patterns of local cerebral glucose utilization determination in Parkinson's disease by the F18-fluorodeoxyglucose method. Ann Neurol, 1984; 15:419-424, 1984).

Perfusion SPECT can also be used to evaluate PTSD. For example, increased perfusion of the caudate has been associated with PTSD (see, for example, Sachinvala N, et al., Increased regional cerebral perfusion by 99mTc hexamethyl propylene amine oxime single photon emission computed tomography in post-traumatic stress disorder. Mil Med. 165(6):473-9, 2000). Compared to controls, PTSD patients have increased cerebral blood flow in the limbic regions along with decreased perfusion in the superior frontal, parietal, and temporal regions (Chung Y A, et al. Alterations in cerebral perfusion in posttraumatic stress disorder patients without re-exposure to accident-related stimuli. Clinical neurophysiology: official journal of the Int. Fed. Clin Neurophysiol. 117(3):637-42, 2006).

SPECT scans of patients with TBI and/or PTSD, compared to controls, allows for a high level of discrimination between the different states.

Neurological changes following treatment can be evaluated using SPECT, particularly when combined with quantitative analysis, for example, using the techniques disclosed in (Henderson and Monies, SPECT Perfusion Imaging Demonstrates Improvement of Traumatic Brain Injury With Transcranial Near-infrared Laser Phototherapy. Adv Mind Body Med. 29(4):27-33, 2015). SPECT combined with quantitative analysis can detect differences in neurological function in a patient who have undergone the treatments described herein. This can be measured, for example, by evaluating increases in cerebral perfusion.

Long-Term Monitoring of Motor Disorders

Parkinson's Disease is one of the most common motor disorders. There are five recognized stages of Parkinson's disease. In stage one, the symptoms are mild and only seen on one side of the body (unilateral involvement), and there is usually minimal or no functional impairment. Stage two is characterized by symptoms on both sides of the body (bilateral involvement) or at the midline without impairment to balance, and may develop months or years after stage one. Stage three is considered mid-stage, and is characterized by loss of balance and slowness of movement. In stage four, PD has progressed to a severely disabling disease. Patients with stage four PD may be able to walk and stand unassisted, but they are noticeably incapacitated. Stage five is the most advanced and is characterized by an inability to rise from a chair or get out of bed without help, a tendency to fall when standing or turning, and freezing or stumbling when walking.

An initial diagnosis of a motor disorder like Parkinson's Disease can also take place in a doctor's office, particularly when a patient shows signs of tremor or shaking, slow movement (called bradykinesia), stiff or rigid arms, legs, or trunk, and/or balance problems or frequent falls. A neurologist can determine how well a patient's arms and legs move, and check muscle tone and balance. The patient may fill out a medical history questionnaire, asking questions regarding other medical conditions the patient is suffering from, what medications are being taken, whether certain activities (handwriting, buttoning buttons, and the like) are more difficult, whether there are changes in the patient's voice (i.e., the voice is softer and/or the speech is slurred), whether there is a change in the sense of smell, or issues with sleep, memory, and/or mood.

Blood tests and/or brain scans can be used to rule out other conditions. Blood tests can identify dopamine deficiency, in which case a medication called carbidopa-levodopa may be prescribed. Additionally, or alternatively, a brain imaging test called a DaTscan, which uses a small amount of a radioactive drug and a special scanner, called a single photon emission computed tomography (SPECT) scanner, can determine dopamine levels in the brain. This initial data can form a baseline, and patients can be measured against this baseline following the course of the treatments described herein. The ability to improve symptoms, or slow the progression of symptoms, can be confirmed by a treating physician.

The diagnosis and treatment of synucleinopathies such as Parkinson disease and dementia with Lewy bodies can be aided by using assays that identify and quantify the pathogenic disease-associated forms of α-synuclein (αSynD). Two recent αSynD seed amplification tests have provided the first prototypes for ultrasensitive and specific detection of αSynD in patients' cerebrospinal fluid (CSF). Another α-synuclein real time quaking-induced conversion (αSyn RT-QuIC) assay that has similar sensitivity and specificity to these assays is disclosed in Groveman, et al., "Rapid and ultra-sensitive quantitation of disease-associated α-synuclein seeds in brain and cerebrospinal fluid by αSyn RT-QuIC," Acta Neuropathol Commun 6, 7 (2018). These tests involve taking a sample of CSF, and quantifying the relative amounts of αSynD seeding activity in cerebrospinal fluid samples. These assays allow this seeing activity to be quantitated, even in early symptomatic stages of synucleinopathy. One can monitor the progress of treatment by obtaining a baseline measurement, and periodically repeating this measurement over the course of therapy.

Long-Term Monitoring of Motor Disorders

Symptoms vary depending on the type of behavioral disorder, but typically include anxiety, obsessive-compulsive behaviors, unusual behaviors, behaviors which affect ability to function fully in daily life, social problems, and/or panic.

The initial diagnosis of a behavioral disorder can include standardized questionnaires, interviews with the child and his/her parents and teachers, as well as a formal diagnosis by a pediatrician, psychiatrist or child psychologist.

Depending on the results of this evaluation, a patient may be diagnosed as having attention deficit hyperactivity disorder (ADHD), autism, Asperger syndrome, Tourett's syndrome, drug or alcohol abuse, gambling addiction, agoraphobia, anorexia nervosa, binge eating disorder, bipolar disorder, bulimia nervosa, depression, depressive disorders, dysthymia, eating disorders, generalized anxiety disorder, mood disorders, obsessive-compulsive disorder, panic disorder, post-traumatic stress disorder (PTSD), social phobia, or specific phobias.

Many of these disorders are associated with underlying neurological abnormalities (see, for example, Kaye W, et al. Neurobiology of anorexia and bulimia nervosa. Physiol Behav 2008 Apr. 22; 94(1): 121-35). The treatments described herein can address these abnormalities, for example, by reducing inflammation, inducing vascularization, and/or increasing levels of various neurotransmitters.

There are recognized home tests for monitoring a patient over time, at least for disorders such as ADHD and other concentration disorders, overall mental health, and emotional stress. The success of the treatments described herein can be monitored over time using these tests.

Any patents, applications and other references that may be listed in accompanying or subsequent filing papers, as well as those listed above, are incorporated herein by reference in their entirety. Aspects of embodiments can be modified, if necessary, to employ the systems, functions, and concepts of the various references to provide yet further embodiments.

The contents of each reference described herein is incorporated by reference in its entirety, for all purposes.

Embodiments in accordance with the present inventive subject matter are described herein in detail in order to provide exact features of representative embodiments that are within the overall scope of the present inventive subject matter. The present inventive subject matter should not be understood to be limited to such detail.

The invention claimed is:

1. A method for treating central nervous system disorders, comprising administering light to a patient in need of treatment thereof, wherein the light comprises a first wavelength that reduces inflammation in the brain, and a second wavelength that increases vascularization in the brain, and wherein the light is administered in a manner that repairs damage to the blood brain barrier by positioning one or more light sources that generate the first wavelength and the second wavelength at a spaced distance from a scalp of the patient and administering the light to penetrate the scalp.

2. The method of claim 1, wherein the spaced distance is within 100 centimeters of the scalp.

3. The method of claim 1, wherein the central nervous system disorders are cognitive disorders, motor disorders, or behavioral disorders.

4. The method of claim 3, wherein the cognitive disorders are selected from the group consisting of Alzheimer's disease, amnesia, Binswanger's disease, cerebellar cognitive affective syndrome, clinical dementia rating, clouding of consciousness, cognitive deficit, cognitive slippage, cognitive vulnerability, corticobasal degeneration, corticobasal syndrome, delirium, dementia, disabilities affecting intellectual abilities, frontal assessment Battery, frontotemporal dementia, frontotemporal dementia and parkinsonism linked to chromosome 17, frontotemporal lobar degeneration, HIV-associated neurocognitive disorders, learning problems in childhood cancer, Lewy body dementia association, Lewy body dementia, logopenic progressive aphasia, mild cognitive impairment, paratonia, Pick's disease, post-chemotherapy cognitive impairment, postoperative cognitive dysfunction, primary progressive aphasia, progressive nonfluent aphasia, progressive supranuclear palsy, pseudosenility, REM sleep behavior disorder, semantic dementia, severe cognitive impairment, subcortical dementia, and vascular dementia.

5. The method of claim 3, wherein the cognitive disorders are selected from the group consisting of Alzheimer's disease, dementia, and mild cognitive impairment.

6. The method of claim 3, wherein the motor disorders are selected from the group consisting of hypokinetic movement disorders, Parkinson's disease (Primary or Idiopathic Parkinsonism), secondary Parkinsonism, Parkinson plus syndromes, Hallevorden-Spatz Disease, progressive supranuclear ophthalmoplegia, striatonigral degeneration, hyperkinetic movement disorders, dystonia, including drug-induced dystonia, idiopathic familial dystonia, idiopathic non-familial dystonia, idiopathic orofacial dystonia, spasmodic torticollis, blepharospasm, and other dystonias, extrapyramidal movement disorders, essential tremors, drug induced tremors, myoclonus, opsoclonus, chorea (rapid, involuntary movement), including drug-induced chorea, rheumatic chorea (Sydenham's chorea), and Huntington's Chorea, ballismus (violent involuntary rapid and irregular movements), hemiballismus (affecting only one side of the body), athetosis (contorted torsion or twisting), dyskinesia (abnormal, involuntary movement), tardive dyskinesia, tic disorders (involuntary, compulsive, repetitive, stereotyped), including Tourette's syndrome and drug-induced tics and tics of organic origin, stereotypic movement disorder, paroxysmal nocturnal limb movement, painful legs (or arms), moving toes (or fingers) syndrome, sporadic restless leg syndrome, familial restless leg syndrome, stiff-person syndrome, abnormal head movements, cramp and spasm, and fasciculation.

7. The method of claim 3, wherein the motor disorders are selected from the group consisting of Parkinson's disease and tardive dyskinesia.

8. The method of claim 3, wherein the behavioral disorders are selected from the group consisting of attention-deficit hyperactivity disorder (ADHD), oppositional defiant disorder (ODD), conduct disorders, schizophrenia, generalized anxiety disorder, specific phobia, social anxiety disorder, separation anxiety disorder, agoraphobia, panic disorder, selective mutism, major depressive disorder, catatonic depression, postpartum depression, premenstrual dysphoric disorder (PMDD), seasonal affective disorder (SAD), dysthymia, double depression, depressive personality disorder (DPD), recurrent brief depression (RBD), minor depressive disorder (minor depression), depressive disorder not otherwise specified (DD-NOS), and bipolar disorders.

9. The method of claim 3, wherein the behavioral disorders are selected from the group consisting of depression, anxiety, schizophrenia, seasonal affective disorder (SAD), and attention-deficit hyperactivity disorder (ADHD).

10. The method of claim 3, further comprising administering one or more drugs useful for treating cognitive disorders.

11. The method of claim 3, further comprising administering one or more drugs useful for treating motor disorders.

12. The method of claim 3, further comprising administering one or more drugs useful for treating behavioral disorders.

13. The method of claim 1, wherein the first wavelength that reduces inflammation is between 640 nm and 680 nm.

14. The method of claim 1, wherein the second wavelength that increases vascularization is in a range of from 400 nm to 490 nm.

15. The method of claim 1, wherein the light is administered using a device which delivers light to the scalp.

16. The method of claim 1, wherein the light is administered using a device which delivers light to the nose.

17. The method of claim 1, wherein the light is administered using a device which delivers light to the eyes.

18. The method of claim 1, wherein the light is administered using a device which delivers light to the ears.

19. The method of claim 1, wherein the light is administered using a probe or catheter.

20. The method of claim 19, wherein the probe is an intra-pharyngeal probe.

21. The method of claim 1, wherein the light is administered using an implant.

22. The method of claim 21, wherein the implant lies between the skull and the scalp.

23. The method of claim 1, further comprising applying a magnetic field.

24. The method of claim 1, wherein the light is applied at a frequency in the range of alpha waves, beta waves, theta waves, or gamma waves.

25. The method of claim 24, wherein the light is applied at a frequency between 30 and 50 Hz.

26. The method of claim 1, further comprising administering pharmaceutical agents to the patient such that they pass through the blood brain barrier.

27. The method of claim 26, wherein the pharmaceutical agents are anticancer agents, and the method is used to treat brain cancer.

28. The method of claim 27, wherein the anticancer agents are selected from the group consisting of 5FC, Accutane, AEE788, AMG-102, Anti Neoplaston, AQ4N (Banoxantrone), AVANDIA (Rosiglitazone Maleate), Avastin (Bevacizumab) BCNU, BiCNU, Carmustine, Carboplatin, CC-223, CC223, CCI-779, CCNU, CCNU Lomustine, Celecoxib (Systemic), Chloroquine, Cilengitide (EMD 121974), Cisplatin, CPT-11 (CAMPTOSAR, Irinotecan), Cytoxan, Dasatinib (BMS-354825, Sprycel), Etoposide (Eposin, Etopophos, Vepesid), GDC-0449, Gleevec (imatinib mesylate), GLIADEL Wafer, Hydroxychloroquine, Hydroxyurea, IL-13, IMC-3G3, Iressa (ZD-1839), Lapatinib (GW572016), Methotrexate, Novocure, OSI-774, PCV, Procarbazine, RAD001, Rapamycin (Rapamune, Sirolimus), RMP-7, RTA 744, Simvastatin, Sirolimus, Sorafenib, SU-101, SU5416 Sugen, Sulfasalazine (Azulfidine), Sutent, Tamoxifen, TARCEVA (erlotinib HCI), Taxol, TEMODAR, TEMODAR, Thalomid (thalidomide), Toca 511, Topotecan (Systemic), VEGF Trap, VEGF-Trap, Velcade, Vincristine, Vorinostat (SAHA), XL 765, XL-184, XL184, XL765, Zarnestra (tipifarnib), and Zocor (simvastatin).

29. The method of claim 27, wherein the brain cancer is selected from the group consisting of gliomas, glioblastoma multiforme, meningiomas, ependymomas, pituitary tumors, craniopharyngiomas, germ cell tumors, pineal region tumors, medulloblastomas, and primary central nervous system (CNS) lymphomas.

* * * * *